United States Patent
Levin et al.

(10) Patent No.: US 6,358,980 B1
(45) Date of Patent: Mar. 19, 2002

(54) ALKYNYL CONTAINING HYDROXAMIC ACID COMPOUNDS AS MATRIX METALLOPROTEINASE/TACE INHIBITORS

(75) Inventors: Jeremy I. Levin, New City; Aranapakam M. Venkatesan, Rekgo Park, both of NY (US); James M. Chen, Bedminister, NJ (US); Arie Zask, New York, NY (US); Vincent P. Sandanayaka, Wesley Hills, NY (US); Mila T. Du, Suffern, NY (US); Jannie L. Baker, White Plains, NY (US)

(73) Assignee: American Cyanamid Company, Madison, NJ (US)

(*) Notice: Subject to any disclaimer, the term of this patent is extended or adjusted under 35 U.S.C. 154(b) by 0 days.

(21) Appl. No.: 09/492,686

(22) Filed: Jan. 27, 2000

Related U.S. Application Data

(60) Provisional application No. 60/155,184, filed on Jan. 27, 1999, now abandoned.

(51) Int. Cl.[7] ............... A61K 31/445; C07D 211/44
(52) U.S. Cl. ............... 514/330; 514/183; 514/211; 514/218; 514/226.8; 514/227.3; 514/231.2; 514/255; 514/256; 514/258; 514/269; 514/309; 514/311; 514/321; 514/323; 514/326; 514/336; 514/357; 514/362; 514/365; 514/367; 514/372; 514/373; 514/374; 514/375; 514/378; 514/379; 514/383; 514/385; 514/394; 514/396; 514/403; 514/408; 514/412; 514/422; 540/544; 540/575; 544/56; 544/59; 544/88; 544/238; 544/283; 544/335; 544/336; 544/353; 546/139; 546/152; 546/186; 546/192; 546/193; 546/197; 546/198; 546/201; 546/202; 546/205; 546/208; 546/209; 546/212; 546/214; 546/268.1; 546/329; 548/128; 548/131; 548/146; 548/152; 548/206; 548/207; 548/215; 548/217; 548/240; 548/241; 548/255; 548/257; 548/300.1; 548/302.7; 548/356.1; 548/356.5; 548/452; 548/469; 548/517; 548/518; 549/14; 549/23; 549/30; 549/49; 549/357; 549/430; 549/462; 549/426

(58) Field of Search ................. 514/183, 211, 514/218, 226.8, 227.3, 231.2, 255, 256, 258, 269, 309, 311, 316, 318, 320, 321, 323, 326, 330, 336, 357, 362, 365, 367, 372, 373, 374, 375, 378, 379, 383, 385, 394, 396, 403, 408, 412, 422; 540/544, 575; 544/56, 59, 88, 238, 283, 335, 336, 353; 546/139, 152, 186, 192, 193, 197, 198, 201, 202, 205, 208, 209, 212, 214, 268.1, 329; 548/128, 131, 146, 152, 206, 207, 215, 217, 240, 241, 255, 257, 300.1, 302.7, 356.1, 356.5, 452, 469, 517, 518; 549/14, 23, 30, 49, 357, 430, 462, 426

(56) References Cited

U.S. PATENT DOCUMENTS

| | | | | |
|---|---|---|---|---|
| 5,028,629 A | * | 7/1991 | Hite et al. | 514/575 |
| 5,455,258 A | | 10/1995 | MacPherson et al. | 514/357 |
| 5,506,242 A | | 4/1996 | MacPherson et al. | 514/336 |
| 5,552,419 A | | 9/1996 | MacPherson et al. | 514/357 |
| 5,753,653 A | | 5/1998 | Bender et al. | 514/227.5 |
| 5,770,624 A | | 6/1998 | Parker | 514/575 |
| 5,804,593 A | | 9/1998 | Warpechoski et al. | 514/419 |
| 5,817,822 A | | 10/1998 | Nantermet et al. | 546/194 |
| 5,929,097 A | | 7/1999 | Levin et al. | 514/351 |
| 5,932,595 A | * | 8/1999 | Bender | 514/317 |
| 6,150,394 A | * | 11/2000 | Watanabe | 514/415 |

FOREIGN PATENT DOCUMENTS

| DE | 19542189 | 5/1997 |
|---|---|---|
| EP | 606046 | 12/1993 |
| EP | 757037 | 7/1996 |

(List continued on next page.)

OTHER PUBLICATIONS

Lambelin et al. "Relations between structure and four types of pharmacologic acitivity in arylacthydroxamic acids" CA 70:36386 (1968).*
Shire, M.G., Exp. Opin. Ther. Patents 8(5), 531 (1998).
Grossman, J.M., Women's Health, 6(6), 627 (1997).
Isomaki, P.J., Ann. Med., 29, 499 (1997).
Camussi, G., Drugs, 55(5), 613 (1998).
Mathison et al., J. Clin. Invest., 81, 1925, (1988).
Miethke et al., J. Exp. Med., 175, 91 (1992).
Piquet, P. F., J. Exp. Med. 166, 1280 (1987).
Beuther, B., Ann. Rev., Biochem, 57, 505 (1988).
Ksontini, R., Arch, Surg., 133, 558, (1998).
Packer, M., Circulation, 92(6), 1379 (1995).
Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230, 630 (1985).
Rankin, E.C. et al., Br. J. Rheumatol., 34, 334 (1995).
Pharmaprojects, Therapeutic Updates 17 (Oct.) au 197, M2Z (1996).
McGeehan et al, Current Pharmaceutical Design, 2, 662 (1996).

(List continued on next page.)

*Primary Examiner*—Ceila Chang
(74) *Attorney, Agent, or Firm*—John W. Hogan, Jr.

(57) ABSTRACT

Compounds of the formula:

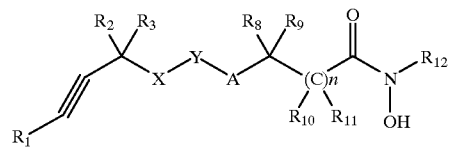

useful in the treatment of arthritis, tumor metastasis, tissue ulceration, abnormal wound healing, periodontal disease, bone disease, diabetes (insulin resistance) and HIV infection.

5 Claims, No Drawings

FOREIGN PATENT DOCUMENTS

| | | |
|---|---|---|
| EP | 757984 | 8/1996 |
| EP | 803505 | 4/1997 |
| WO | WO9535275 | 12/1995 |
| WO | WO9535276 | 12/1995 |
| WO | WO9600214 | 1/1996 |
| WO | WO9627583 | 9/1996 |
| WO | WO9633172 | 10/1996 |
| WO | WO9718194 | 5/1997 |
| WO | WO9719068 | 5/1997 |
| WO | WO9720824 | 6/1997 |
| WO | WO9722587 | 6/1997 |
| WO | WO9727174 | 7/1997 |
| WO | WO9745402 | 12/1997 |
| WO | WO9803166 | 1/1998 |
| WO | WO9807697 | 2/1998 |
| WO | WO9808815 | 3/1998 |
| WO | WO9808822 | 3/1998 |
| WO | WO9808823 | 3/1998 |
| WO | WO9808825 | 3/1998 |
| WO | WO9808827 | 3/1998 |
| WO | WO9808853 | 3/1998 |
| WO | WO9816503 | 4/1998 |
| WO | WO9816506 | 4/1998 |
| WO | WO9816514 | 4/1998 |
| WO | WO9816520 | 4/1998 |
| WO | WO9827069 | 6/1998 |
| WO | WO9831664 | 7/1998 |
| WO | WO9833768 | 8/1998 |
| WO | WO9834918 | 8/1998 |
| WO | WO-98/37877 | * 9/1998 |
| WO | WO9839313 | 9/1998 |
| WO | WO9839329 | 9/1998 |
| WO | WO9842659 | 10/1998 |
| WO | WO9843963 | 10/1998 |
| WO | WO-9925687 | * 5/1999 |

OTHER PUBLICATIONS

Script 20, 2349 (1998).
MacPherson et al., J. Med. Chem., 40, 2525 (1997).
Tamura et al., J. Med. Chem. 41, 640 (1998).
Levin et al., Bioorg. & Med. Chem. Letters, 8, 2657 (1998).
Pikul et al., J. Med. Chem., 41, 3568 (1998).

* cited by examiner

ALKYNYL CONTAINING HYDROXAMIC ACID COMPOUNDS AS MATRIX METALLOPROTEINASE/TACE INHIBITORS

This application claims the benefit of U.S. Provisional Application No. 60/155,184, filed Jan. 27, 1999.

FIELD OF INVENTION

This invention relates to acetylenic hydroxamic acids which act as inhibitors of TNF-α converting enzyme (TACE). The compounds of the present invention are useful in disease conditions mediated by TNF-α, such as rheumatoid arthritis, osteoarthritis, sepsis, AIDS, ulcerative colitis, multiple sclerosis, Crohn's disease and degenerative cartilage loss.

BACKGROUND OF THE INVENTION

Matrix metalloproteinases (MMPs) are a group of enzymes that have been implicated in the pathological destruction of connective tissue and basement membranes. These zinc containing endopeptidases consist of several subsets of enzymes including collagenases, stromelysins and gelatinases. Of these classes, the gelatinases have been shown to be the MMPs most intimately involved with the growth and spread of tumors. It is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology. Furthermore, there is evidence to suggest that gelatinase is involved in plaque rupture associated with atherosclerosis. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neo-vascularization and corneal graft rejection. For recent reviews, see: (1) Recent Advances in Matrix Metalloproteinase Inhibitor Research, R. P. Beckett, A. H. Davidson, A. H. Drummond, P. Huxley and M. Whittaker, Research Focus, Vol. 1, 16–26, (1996), (2) Curr. Opin. Ther. Patents (1994) 4(1): 7–16, (3) Curr. Medicinal Chem. (1995) 2: 743–762, (4) Exp. Opin. Ther. Patents (1995) 5(2): 1087–110, (5) Exp. Opin. Ther. Patents (1995) 5(12): 1287–1196: (6) Exp. Opin. Ther. Patents (1998) 8(3): 281–259.

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. Exp. Opin. Ther. Patents 1998, 8(5), 531; Grossman, J. M.; Brahn, E. J. Women's Health 1997, 6(6), 627; Isomaki, P.; Punnonen, J. Ann. Med. 1997, 29, 499; Camussi, G.; Lupia, E. Drugs, 1998, 55(5), 613.] septic shock [Mathison, et. al. J. Clin. Invest. 1988, 81, 1925; Miethke, et. al. J. Exp. Med. 1992, 175, 91.], graft rejection [Piguet, P. F.; Grau, G. E.; et. al. J. Exp. Med. 1987, 166, 1280.], cachexia [Beutler, B.; Cerami, A. Ann. Rev. Biochem. 1988, 57, 505.], anorexia, inflammation [Ksontini, R,; MacKay, S. L. D.; Moldawer, L. L. Arch. Surg. 1998, 133, 558.], congestive heart failure [Packer, M. Circulation, 1995, 92(6), 1379; Ferrari, R.; Bachetti, T.; et. al. Circulation, 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. Science, 1993, 259, 87.] and HIV infection [Peterson, P. K.; Gekker, G.; et. al. J. Clin. Invest. 1992, 89, 574; Pallares-Trujillo, J.; Lopez-Soriano, F. J. Argiles, J. M. Med. Res. Reviews, 1995, 15(6), 533.]], in addition to its well-documented antitumor properties [Old, L. Science, 1985, 230, 630.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. Br. J. Rheumatol. 1995, 34, 334; Pharmaprojects, 1996, Therapeutic Updates 17 (October), 197-M2Z.]. This observation has recently been extended to humans as well as described in "TNF-α in Human Diseases", Current Pharmaceutical Design, 1996, 2, 662.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [Scrip, 1998, 2349, 20] Long acting, selective, orally bioavailable non-peptide inhibitors of TACE would thus be highly desirable for the treatment of the disease states discussed above.

Sulfone hydroxamic acid inhibitors of MMPs, of general structure I have been disclosed [Burgess, L. E.; Rizzi, J. P.; Rawson, D. J. Eur Patent Appl. 818442. Groneberg, R. D.; Neuenschwander, K. W.; Djuric, S. W.; McGeehan, G. M.; Burns, C. J.; Condon, S. M.; Morrissette, M. M.; Salvino, J. M.; Scotese, A. C.; Ullrich, J. W. PCT Int. Appl. WO 97/24117. Bender, S. L.; Broka, C. A.; Campbell, J. A.; Castelhano, A. L.; Fisher, L. E.; Hendricks, R. T.; Sarma, K. Eur. Patent Appl. 780386. Venkatesan, A. M.; Grosu, G. T.; Davis, J. M.; Hu, B.; O'Dell, M. J. PCT Int. Appl. WO 98/38163.]. An exemplification of this class of MMP inhibitor is RS-130830, shown below.

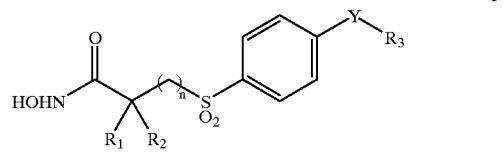

I

-continued

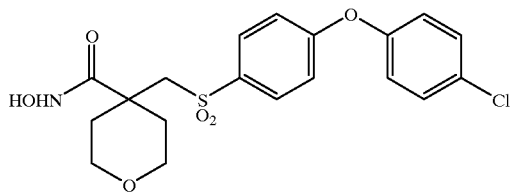

RS-130830

Within the sulfone-hydroxamic acid class of MMP inhibitor, the linker between the sulfone and hydroxamic acid moieties has been extended to three carbons (I, n=2) without significant loss in potency [Barta, T. E.; Becker, D. P.; Villamil, C. I.; Freskos, J. N.; Mischke, B. V.; Mullins, P. B.; Heintz, R. M.; Getman, D. P.; McDonald, J. J. PCT Int. Appl. WO 98/39316. McDonald, J. J.; Barta, T. E.; Becker, D. P.; Bedell, L. J.; Rao, S. N.; Freskos, J. N.; Mischke, B. V. PCT Int. Appl. WO 98/38859.].

Piperidine sulfone hydroxamic acids, II (n=1) have been reported [Becker, D. P.; Villamil, C. I.; Boehm, T. L.; Getman, D. P.; McDonald, J. J.; DeCrescenzo, G. A. PCT Int. Appl. WO 98/39315.]. Similar piperidine derivatives in which the methylene linking the piperidine ring to the sulfone has been deleted (II, n=0) have been reported [Venkatesan, A. M.; Grosu, G. T.; Davis, J. M.; Baker, J. L. PCT Int. Appl. WO 98/37877.].

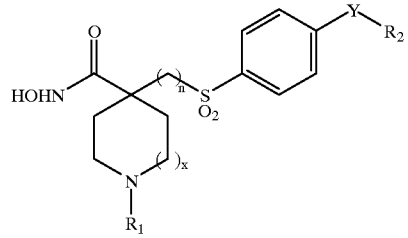

II

Sulfone-hydroxamic acids III, in which a hydroxyl group has been placed alpha to the hydroxamic acid, have been disclosed [Freskos, J. N.; Boehm, T. L.; Mischke, B. V.; Heintz, R. M.; McDonald, J. J.; DeCrescenzo, G. A.; Howard, S. C. PCT Int. Appl. WO 98/39326. Robinson, R. P. PCT Int. Appl. WO 98/34915.].

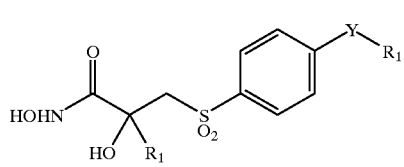

III

Sulfone-based MMP inhibitors of general structure IV, which utilize a thiol as the zinc chelator, have been reported [Freskos, J. N.; Abbas, Z. S.; DeCrescenzo, G. A.; Getman, D. P.; Heintz, R. M.; Mischke, B. V.; McDonald, J. J. PCT Int. Appl. WO 98/03164].

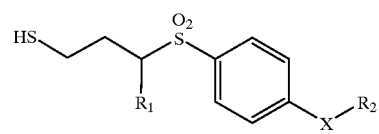

IV

Inhibitors of stromelysin with general structure V have been disclosed [Shuker, S. B.; Hajduk, P. J.; Meadows, R. P.; Fesik, S. W. Science, 1996, 274, 1531–1534. Hajduk, P. J.; Sheppard, G.; Nettesheim, D. G.; Olejniczak, E. T.; Shuker, S. B.; Meadows, R. P.; Steinman, D. H.; Carrera, Jr., G. M.; Marcotte, P. A.; Severin, J.; Walter, K.; Smith, H.; Gubbins, E.; Simmer, R.; Holzman, T. F.; Morgan, D. W.; Davidsen, S. K.; Summers, J. B.; Fesik, S. W. J. Am. Chem. Soc. 1997, 119, 5818–5827. Olejniczak, E. T.; Hajduk, P. J.; Marcotte, P. A.; Nettesheim, D. G.; Meadows, R. P.; Edalji, R.; Holzman, T. F.; Fesik, S. W. J. Am. Chem. Soc. 1997, 119, 5828–5832. Fesik, S. W.; Summers, J. B.; Davidsen, S. K.; Sheppard, G. S.; Steinman, D. H.; Carrera, G. M.; Florjancic, A.; Holms, J. H. PCT Int. Appl. WO 97/18188.].

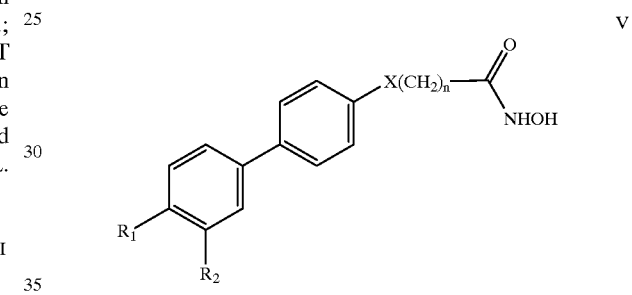

V

Salah et al., Liebigs Ann. Chem. 195, (1973) discloses some aryl substituted thio and aryl substituted sulfonyl acetohydroxamic acid derivatives of general formula 1. These compounds were prepared to study the Mannich reaction. Subsequently, they were tested for their fungicidal activity.

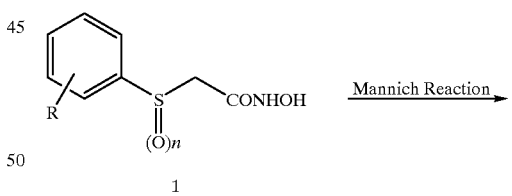

1

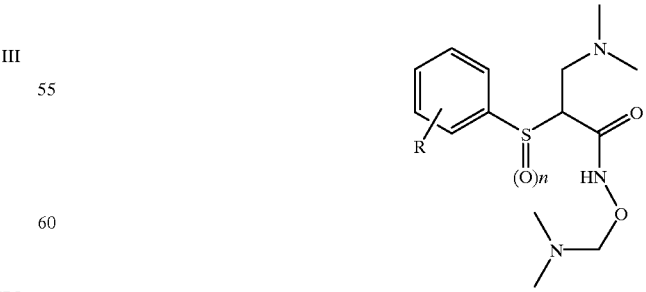

Some sulfone carboxylic acids are disclosed in U.S. Pat. No. 4,933,367. Those compounds were shown to exhibit hypoglycemic activity.

DETAILED DESCRIPTION OF THE INVENTION

The present invention relates to novel, low molecular weight, non-peptide inhibitors of matrix metalloproteinases (MMPs) and TNF-α converting enzyme (TACE) for the treatment of arthritis, tumor metastasis, tissue ulceration, abnormal wound healing, periodontal disease, bone disease, diabetes (insulin resistance) and HIV infection.

In accordance with this invention there is provided a group of compounds of general formula I:

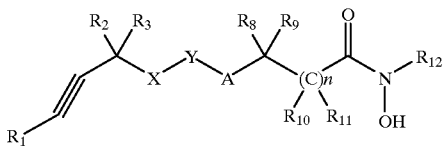

wherein:
- $R_1$ is hydrogen, aryl, heteroaryl, alkyl of 1–8 carbon atoms, alkenyl of 2–6 carbon atoms, alkynyl of 2–6 carbon atoms, cycloalkyl of 3–6 carbon atoms, or —$C_4$–$C_8$-cycloheteroalkyl;
- $R_2$ and $R_3$ are each, independently, hydrogen, alkyl of 1–6 carbon atoms, —CN, or —CCH;
- $R_7$ is hydrogen, aryl, aralkyl, heteroaryl, heteroaralkyl, alkyl of 1–6 carbon atoms, alkenyl of 2–6 carbon atoms, alkynyl of 1–6 carbon atoms, cycloalkyl of 3–6 carbon atoms, —C(O)—$R_1$, —$SO_2$—$R_1$, —C(O)—$NHR_1$, —C(O)$NR_5R_6$, —C(O)$R_1NR_5R_6$, —C(O)—$OR_1$, —C(NH)—$NH_{.2}$.
- $R_8$, $R_9$, $R_{10}$, and $R_{11}$ are each, independently, hydrogen, aryl or heteroaryl, cycloalkyl of 3–6 carbon atoms, —$C_4$–$C_8$-cycloheteroalkyl, alkyl of 1–18 carbon atoms, alkenyl of 2–18 carbon atoms, alkynyl of 2–18 carbon atoms; with the proviso that one of the pairs R8 and R9, R9 and R10 or R10 and R11, together with the carbon atom or atoms to which they are attached, form a cycloalkyl ring of 3–6 carbon atoms, or a —$C_4$–$C_8$-cycloheteroalkyl ring;
- $R_{12}$ is hydrogen, aryl or heteroaryl, cycloalkyl of 3–6 carbon atoms, —$C_4$–$C_8$-cycloheteroalkyl, or alkyl of 1–6 carbon atoms;
- A is O, S, SO, $SO_2$, $NR_7$, or $CH_2$;
- X is O, S, SO, $SO_2$, $NR_7$, or $CH_2$;
- Y is aryl or heteroaryl, with the proviso that A and X are not bonded to adjacent atoms of Y; and
- n is 0–2; or a pharmaceutically acceptable salt thereof.

In some preferred aspects of the invention, Y is phenyl, pyridyl, thienyl, furanyl, imidazolyl, triazolyl or thiadiazolyl, with the proviso that A and X are not bonded to adjacent atoms of Y.

In still other preferred embodiments of the invention Y is phenyl, thienyl or furanyl.

In accordance with certain preferred embodiments of the invention $R_8$ and $R_9$, together with the carbon atom to which they are attached form a $C_4$–$C_8$ cycloheteroalkyl ring and K is $NR_7$.

The most preferred matrix metalloproteinase and TACE inhibiting compounds of this invention are:

1-(4-Bromo-benzyl)-4-(4-but-2-ynyxoy-benzenesulfonyl)-piperdine-4-carboxylic acid hydroxyamide;
4-(4-But-2-ynyloxy-benzenesulfonyl)-1-(4-methoxy-benzyl)-piperdine-4-carboxylic acid hydroxyamide;
4-(4-But-2-ynyloxy-benzenesulfonyl)-1-(4-chloro-benzyl)-piperdine-4-carboxylic acid hydroxyamide;
1-Benzyl-4-(4-but-2-ynyloxy-benzenesulfonyl)-piperdine-4-carboxylic acid hydroxamide;
1-(4-Bromo-benzyl)-4-(4-pent-2-ynyloxy-benzenesulfonyl)-piperdine-4-carboxylic acid hydroxyamide;
1-(4-Bromo-benzyl)-4-(4-oct-2-ynyloxy-benzenesulfonyl)-piperdine-4-carboxylic acid hydroxyamide;
4-(4-But-2-ynyloxy-benzenesulfonyl)-1-(4-fluoro-benzyl)-piperdine-4-carboxylic acid hydroxyamide;
4-(4-But-2-ynyloxy-benzenesulfonyl)-1-(4-cyano-benzyl)-piperidine-4-carboxylic acid hydroxamide;
4-(4-But-2-ynyloxy-benzenesulfonyl)-1-(4-methyl-benzyl)-piperidine-4-carboxylic acid hydroxamide;
4-(4-But-2-ynyloxy-benzenesulfonyl)-1-(3,4-dichloro-benzyl)-piperidine-4-carboxylic acid hydroxamide;
1-(4-Bromo-benzyl)-4-(4-prop-2-ynyloxy-benzenesulfonyl)-piperdine-4-carboxylic acid hydroxyamide;
1-(4-Bromo-benzyl)-4-[4-(4-piperdin-4-yl-but-2-ynyloxy)-benzenesulfonyl]-piperdine-4-carboxylic acid hydroxyamide;
1-(4-Bromo-benzyl)-4-[4-(4-morpholin-4-yl-but-2-ynyloxy)-benzene-sulfonyl]-piperdine-4-carboxylic acid hydroxyamide;
4-(4-But-2-ynyloxy-phenylsulfanyl)-4-hydroxycarbamoyl-piperidine-1-carboxylic acid tert-butyl ester;
4-(4-But-2-ynyloxy-phenylsulfanyl)-piperidine-4-carboxylic acid hydroxyamide
1-(4-Bromo-benzyl)-4-(4-but-2-ynyloxy-phenylsulfanyl)-piperidine-4-carboxylic acid hydroxyamide;
4-(4-But-2-ynyloxy-phenylsulfanylmethyl)-tetrahydro-pyran-4-carboxylic acid hydroxyamide;
4-(4-But-2-ynyloxy-benzenesulfonylmethyl)-tetrahydro-pyran-4-carboxylic acid hydroxyamide;
4-(4-But-2-ynyloxy-benzenesulfinylmethyl)-tetrahydro-pyran-4-carboxylic acid hydroxyamide;
4-{[4-(2-butynyloxy)phenyl]sulfonyl}-N-hydroxytetrahydro-2H-pyran-4-carboxamide;
1-benzyl-4-{[3-(2-butynyloxy)phenyl]sulfonyl}-N-hydroxy-4-piperdine carboxamide;
4-{[4-(2-butynyloxy)phenyl]sulfonyl}-N-hydroxy-1-isopropyl-4-piperidine carboxamide;
4-{[4-(2-butynyloxy)phenyl]sulfonyl}-N-hydroxy-1-(3-pyridinylmethyl)-4-piperidine carboxamide;
3-{[4-(2-Butynyloxy)phenyl]sulfonyl}-1-ethyl-N-hydroxy-3-piperidine-carboxarnide;
3-{[4-(2-butynyloxy)phenyl]sulfonyl}-1-(4-chlorobenzyl)-N-hydroxy-3-piperidinecarboxamide;
4-{[4-(2-Butynyloxy)phenyl]sulfonyl}-1-[4-(2-piperidin-1yl-ethoxy)-benzyl]-piperidine-4-carboxylic acid hydroxyamide;
4-{[4-(2-Butynyloxy)phenyl]sulfonyl}-1-(3-pentanyl)-piperidine-4-carboxylic acid hydroxyamide;
1-(4-Methoxy-benzyl)-4-(4-prop-2-ynyloxy-benzenesulfonyl)-piperidine-4-carboxylic acid hydroxyamide;
1-(4-Chloro-benzyl)-4-(4-prop-2-ynyloxy-benzenesulfonyl)-piperidine-4-carboxylic acid hydroxyamide;
tert-butyl-4-({[4-(2-butynyloxy)phenyl]sulfanyl}methyl)-4-[(hydroxyamino)-carbonyl]-1-piperidinecarboxylate;
4-({[4-(But-2-ynyloxy)phenyl]thio}methyl)-N-hydroxypiperidine-4-carboxamide;
tert-Butyl-4-({[4-(2-butynyloxy)phenyl]sulfinyl}methyl)-4-[(hydroxyamino)-carbonyl]-1-piperidinecarboxylate;

4-[[[4-(2-Butynyloxy)phenyl]sulfinyl]methyl]-N-hydroxy-4-piperidine-carboxamide;
tert-Butyl-4-({[4-(but-2-ynyloxy)phenyl]sulfonyl}methyl)-4-[(hydroxyamino)-carbonyl]piperidine-1-carboxylate;
tert-butyl-4-({[4-(2-butynyloxy)phenyl]sulfonyl}methyl)-4-[(hydroxyamino)-carbonyl]-1-piperidinecarboxyla;
1-Acetyl-4-[[[4-(2-butynyloxy)phenyl]sulfonyl]methyl]-N-hydroxy-4-piperidinecarboxamide;
1-(2-Butynyl)-4-({[4-(2-butynyloxy)phenyl]sulfonyl}methyl)-N-hydroxy-4-piperidinecarboxamide hydrochloride;
N-1-(tert-Butyl)-4-({[4-(2-butynyloxy)phenyl]sulfonyl}methyl)-N-4-hydroxy-1,4-[4-(2-butynyloxy)phenyl]sulfonyl}methyl)-N-4-hydroxy-1,4-1]sulfonyl}-methyl)-N~4~-hydroxy-1,4-piperidinedicarboxamide;
Methyl 4-({[4-(2-butynyloxy)phenyl]sulfonyl}methyl)-4-[(hydroxyamino)-carbonyl]-1-piperidinecarboxylate;
Benzyl 4-({[4-(2-butynyloxy)phenyl]sulfonyl}methyl)-4-[(hydroxyamino)-carbonyl]-1-piperidinecarboxylate;
1-Benzyl-4-({[4-(2-butynyloxy)phenyl]sulfonyl}methyl)-N-hydroxy-4-butynyloxy)phenyl]sulfonyl}methyl)-N-hydroxy-4-piperidinecarboxamide;
4-({[4-(2-Butynyloxy)phenyl]sulfonyl}methyl)-N-hydroxy-1-[(2,2,5-trimethyl-1,3-dioxan-5-yl)carbonyl]-4-piperidinecarboxamide;
4-({[4-(2-Butynyloxy)phenyl]sulfonyl}methyl)-N-hydroxy-1-[3-hydroxy-2-(hydroxymethyl)-2-methylpropanoyl]-4-piperidinecarboxamide;
1-[Amino(imino)methyl]-4-({[4-(2-butynyloxy)phenyl]sulfonyl}methyl)-N-hydroxy-4-1]-4-({[4-(2-butynyloxy)phenyl]sulfonyl}methyl)-N-hydroxy-4-oxy)phenyl]sulfonyl}methyl)-N-hydroxy-4-piperidinecarboxamide;
4-({[4-(2-Butynyloxy)phenyl]sulfonyl}methyl)-N-hydroxy-1-(4-hydroxy-2-butynyl)-henyl]sulfonyl}methyl)-N-hydroxy-1-(4-hydroxy-2-butynyl)-4-piperidinecarboxamide;
4-({[4-(But-2-ynyloxy)phenyl]sulfonyl}methyl)-1-ethyl-N-hydroxypiperidine-4-carboxamide triflouroacetic acid salt;
2-chloro-5-(chloromethyl) thiophene4-({[4-(But-2-ynyloxy)phenyl]-sulfonyl}-methyl)-1-[(5-chlorothien-2-yl)methyl]-N-hydroxypiperidine-4-carboxamide triflouroacetic acid salt;
4-({[4-(But-2-ynyloxy)phenyl]sulfonyl}methyl)-N-hydroxy-1-(pyridin-4-ylmethyl)piperidine-4-carboxamide triflouroacetic acid salt;
4-({[4-(But-2-ynyloxy)phenyl]sulfonyl}methyl)-N-hydroxy-1-(pyridin-3ylcarbonyl)piperidine-4-carboxamide triflouroacetic acid salt;
1-Benzoyl-4-({[4-(but-2-ynyloxy)phenyl]sulfonyl}methyl)-N-hydroxy-piperidine-4-carboxamide;
4-({[4-(But-2-ynyloxy)phenyl]sulfonyl}methyl)-N-hydroxy-1-(thien-2-ylcarbonyl) piperidine-4-carboxamide;
4-({[4-(But-2-ynyloxy)phenyl]sulfonyl}methyl)-N-1-ethyl-N-4-hydroxy-piperidine-1,4-dicarboxamide;
4-({[4-(But-2-ynyloxy)phenyl]sulfonyl}methyl)-N-4-hydroxy-N-1-phenyl-piperidine-1,4-dicarboxamide;
4-({[4-(But-2-ynyloxy)phenyl]sulfonyl}methyl)-N-1-,N-1-diethyl-N-4-hydroxypiperidine-1,4-dicarboxamide;
4-({[4-(But-2-ynyloxy)phenyl]sulfonyl}methyl)-N-hydroxy-1-(morpholin-4-ylcarbonyl)piperidine-4-carboxamide;
4-({[4-(But-2-ynyloxy)phenyl]sulfonyl}methyl)-N-4-hydroxy-N-1-methyl-N-1-phenylpiperidine-1,4-dicarboxamide;
Octyl-4-({[4-(but-2-ynyloxy)phenyl]sulfonyl}methyl)-4-[(hydroxyamino)-carbonyl]piperidine-1-carboxylate;
4-Methoxyphenyl4-({[4-(but-2-ynyloxy)phenyl]sulfonyl}methyl)-4-[(hydroxyamino)carbonyl]piperidine-1-carboxylate;
4-({[4-(But-2-ynyloxy)phenyl]sulfonyl}methyl)-N-hydroxy-1-(phenylsulfonyl)piperidine-4-carboxamide;
4-({[4-(But-2-ynyloxy)phenyl]sulfonyl}methyl)-N-hydroxy-1-[(1-methyl-1H-imidazol-4-yl)sulfonyl]piperidine-4-carboxamide;
1-[2-(Benzylamino)acetyl]-4-({[4-(but-2-ynyloxy)phenyl]-sulfonyl}methyl)-N-hydroxypiperidine-4-carboxamide;
4-({[4-(But-2-ynyloxy)phenyl]sulfonyl}methyl)-N-hydroxy-1-(2-morpholin-4-ylacetyl)piperidine-4-carboxamide;
4-({[4-(But-2-ynyloxy)phenyl]sulfonyl}methyl)-N-hydroxy-1-[2-(4-methyl-piperazin-1-yl)acetyl]piperidine-4-carboxamide;
1-Acetyl-4-(4-but-2-ynyloxybenzenesulfonyl)piperidine-4-carboxylic acid hydroxamide;
1-Benzoyl-4-(4-but-2-ynyloxybenzenesulfonyl)piperidine-4-carboxylic acid hydroxamide;
1-(4-Methoxybenzoyl)-4-(4-but-2-ynyloxybenzenesulfonyl)piperidine-4-carboxylic acid hydroxamide;
4-(4-But-2-ynyloxybenzenesulfonyl)-N-hydroxy-1-(pyrrolidine-1-carbonyl)-4-piperidinecarboxamide;
Ethyl 4-(4-but-2-ynyloxybenzenesulfonyl)-4-[(hydroxyamino)carbonyl]-1-piperidinecarboxylate;
4-(4-But-2-ynyloxybenzenesulfonyl)-N-hydroxy-1-[(trifluoromethyl)sulfonyl]-4-piperidinecarboxamide;
4-(4-But-2-ynyloxybenzenesulfonyl)-N-hydroxy-1-(3-pyridinylcarbonyl)-4-piperidinecarboxamide;
4-(4-but-2-ynyloxybenzenesulfonyl)-N-hydroxy-1-(2-thienylcarbonyl)-4-piperidinecarboxamide;
4-(4-but-2-ynyloxybenzenesulfonyl)-N-hydroxy-1-[(4-methoxyphenyl)-sulfonyl]-4-piperidinecarboxamide;
4-(4-but-2-ynyloxybenzenesulfonyl)-N-hydroxy-1-[(2,2,5-trimethyl-1,3-dioxan-5-yl)carbonyl]-4-piperidinecarboxamide;
Tert-butyl-4-{[4-(2-butynyloxy)phenyl]sulfonyl}-4-[(hydroxyamino)carbonyl]-1-piperidinecarboxalate;
4-{[4-(2-butynyloxy)phenyl]sulfonyl}-N-hydroxy-4-piperidinecarboxamide hydrochloride;
Methyl ({4-{[4-(2-butynyloxy)phenyl]sulfonyl}-4-[(hydroxyamino)carbonyl]-1-piperidinyl}methyl)benzoate hydrochloride;
4-({4-{[4-(2-butynyloxy)phenyl]sulfonyl}-4-[(hydroxyamino)carbonyl]-1-piperidinyl}methyl)benzoic acid hydrochloride;
1-[4-(Aminocarbonyl)benzyl]-4-{[4-(2-butynyloxy)phenyl]sulfonyl}-N-hydroxy-4-piperidinecarboxamide hydrochloride;
Tert-butyl 4-{[4-(but-2-ynyloxy)phenyl]sulfinyl}-4-[(hydroxyamino)-carbonyl]piperidine-1-carboxalate;
4-(4-(But-2-ynyloxy-benzenesulfinyl)-piperidine-4-carboxylic acid hydroxamide hydrochloride; and
1-(4-Bromo-benzyl)-4-(4-But-2-ynyloxy-benzenesulfinyl)-piperidine-4-carboxylic acid hydroxamide hydrochloride;

and pharmaceutical salts thereof.

Heteroaryl, as used throughout, is a 5–10 membered mono- or bicyclic aromatic ring having from 1–3 heteroatoms selected from N, NR7, S and O. Heteroaryl is preferably

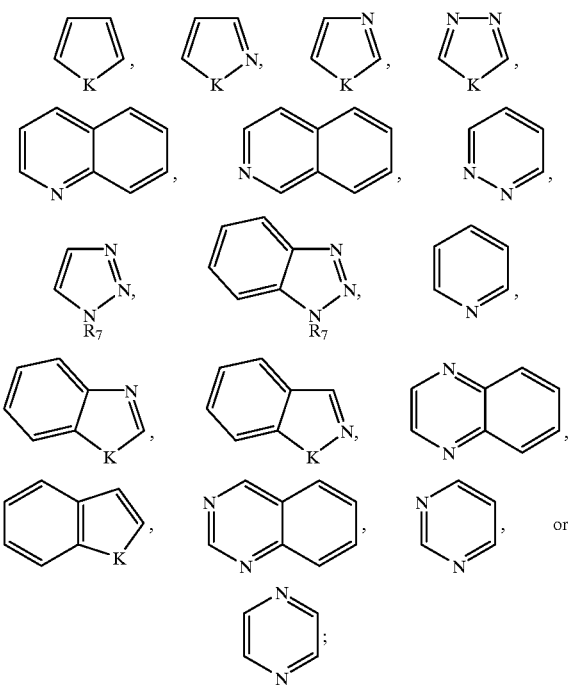

wherein K is defined as O, S or —NR$_7$, and R$_7$ is hydrogen, aryl, aralkyl, heteroaryl, heteroaralkyl, alkyl of 1–6 carbon atoms, alkenyl of 2–6 carbon atoms, alkynyl of 1–6 carbon atoms, cycloalkyl of 3–6 carbon atoms, —C(O)—R$_1$, —SO$_2$—R$_1$, —C(O)—NHR$_1$, —C(O)NR$_5$R$_6$, —C(O)R$_1$, NR$_5$R$_6$, —C(O)—OR$_1$, —C(NH)—NH$_2$.

Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. Heteroaryl groups of the present invention may be mono or disubstituted.

—C$_4$–C$_8$-cycloheteroalkyl is defined as

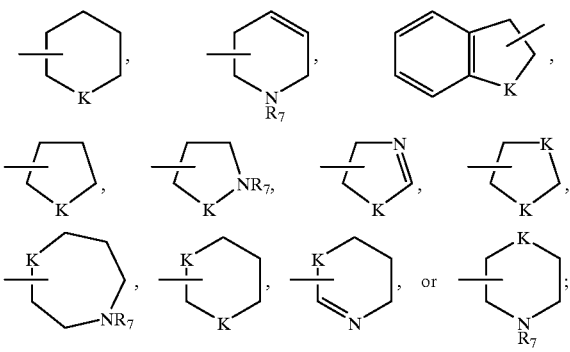

wherein K is O, S or NR7 and R7 is as defined before.
Preferred heterocycloalkyl rings include piperidine, piperazine, morpholine, tetrahydropyran, tetrahydrofuran or pyrrolidine. Heterocycloalkyl groups of the present invention may optionally be mono- or di-substituted.

Aryl, as used herein refers to phenyl or naphthyl aromatic rings which may, optionally be mono- or di-substituted.

Alkyl, alkenyl, alkynyl, and perfluoroalkyl include both straight chain as well as branched moieties. Alkyl, alkenyl, alkynyl, and cycloalkyl groups may be unsubstituted (carbons bonded to hydrogen, or other carbons in the chain or ring) or may be mono- or poly-substituted.

Aralkyl as used herein refers to a substituted alkyl group, -alkyl-aryl, wherein alkyl is lower alkyl and preferably from 1–3 carbon atoms, and aryl is as previously defined.

Heteroaralkyl as used herein refers to a substituted alkyl group, alkyl-heteroaryl wherein alkyl is lower alkyl and preferably from 1–3 carbon atoms, and heteroaryl is as previously defined.

Halogen means bromine, chlorine, fluorine, and iodine.

Suitable substituents of aryl, aralkyl, heteroaryl, heteroaralkyl, alkyl, alkenyl, alkynyl and cycloalkyl include, but are not limited to halogen, alkyl of 1–6 carbon atoms; alkenyl of 2–6 carbon atoms; alkynyl of 2–6 carbon atoms, cycloalkyl of 3–6 carbon atoms, —OR$_5$, =O, —CN, —COR$_5$, perfluoroalkyl of 1–4 carbon atoms, —O-perfluoroalkyl of 1–4 carbon atoms, —CONR$_5$R$_6$, —S(O)$_n$R$_5$, —OPO(OR$_5$)OR$_6$, —PO(OR$_5$)R$_6$, —OC(O)OR$_5$, —OR$_5$NR$_5$R$_6$, —OC(O)NR$_5$R$_6$, —C(O)NR$_5$OR$_6$, —COOR$_5$, —SO$_3$H, —NR$_5$R$_6$, —N[(CH$_2$)$_2$]$_2$NR$_5$, —NR$_5$COR$_6$, —NR$_5$COOR$_6$, —SO$_2$NR$_5$R$_6$, —NO$_2$, —N(R$_5$)SO$_2$R$_6$, —NR$_5$CONR$_5$R$_6$, —NR$_5$C(=NR$_6$)NR$_5$R$_6$, —NR$_5$C(=NR$_6$)N(SO2R$_5$)R$_6$, —NR$_5$C(=NR$_6$)N(C=OR$_5$)R$_6$, -tetrazol-5-yl, —SO$_2$NHCN, —SO$_2$NHCONR$_5$R$_6$, phenyl, heteroaryl or —C$_4$–C$_8$-cycloheteroalkyl;
wherein
—NR$_5$R$_6$ may form a pyrrolidine, piperidine, morpholine, thiomorpholine, oxazolidine, thiazolidine, pyrazolidine, piperazine, or azetidine ring;
R$_5$ and R$_6$ are each, independently, hydrogen, alkyl of 1–6 carbon atoms, cycloalkyl of 3–6 carbon atoms, aryl, aralkyl, heteroaryl, heteroaralkyl or —C$_4$–C$_8$-cycloheteroalkyl;
R$_7$ is hydrogen, aryl, heteroaryl, alkyl of 1–6 carbon atoms or cycloalkyl of 3–6 carbon atoms, —C(O)—R$_1$, —SO$_2$—R$_1$, —C(O)—NHR$_1$, —C(O)—OR$_1$, —C(NH)—NH$_2$; and n is 0–2.

When a moiety contains more than substituent with the same designation each of those substituents may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

Also according to the present invention, there are provided processes for producing the compounds of the present invention.

Process of the Invention

The compounds of the present invention may be prepared according to one of the general processes outlined below.

The compounds of the present invention, where n=0, X=O, S or NR$^7$, and R$^8$ and R$^9$ taken with the carbon atom to which they are attached, form a six membered heterocyclic ring containing N—R$^7$, S or O and A=S, SO or SO$_2$ may be prepared according to one of the general processes outlined below.

As outlined in scheme 1, the appropriately substituted mercaptan derivative was alkylated using α-bromo acetic acid ester derivative in refluxing chloroform using N,N-diisopropylethylamine as base. The sulfide derivative thus obtained was reacted with appropriately substituted propargyl bromide derivative in refluxing acetone using K$_2$CO$_3$ as base. In the case of X=—N—R$^7$ the N-alkylation can be carried out in DMF/NaH at room temperature. The sulfide derivative thus obtained was oxidized using m-chloroperbenzoic acid in CH$_2$Cl$_2$ or by using Oxone in methanol/water. The sulfone thus obtained can be converted to the corresponding piperidine derivative by reacting it with bis(2-chloroethyl)N-substituted amine derivative.

SCHEME 1

SYNTHESIS:

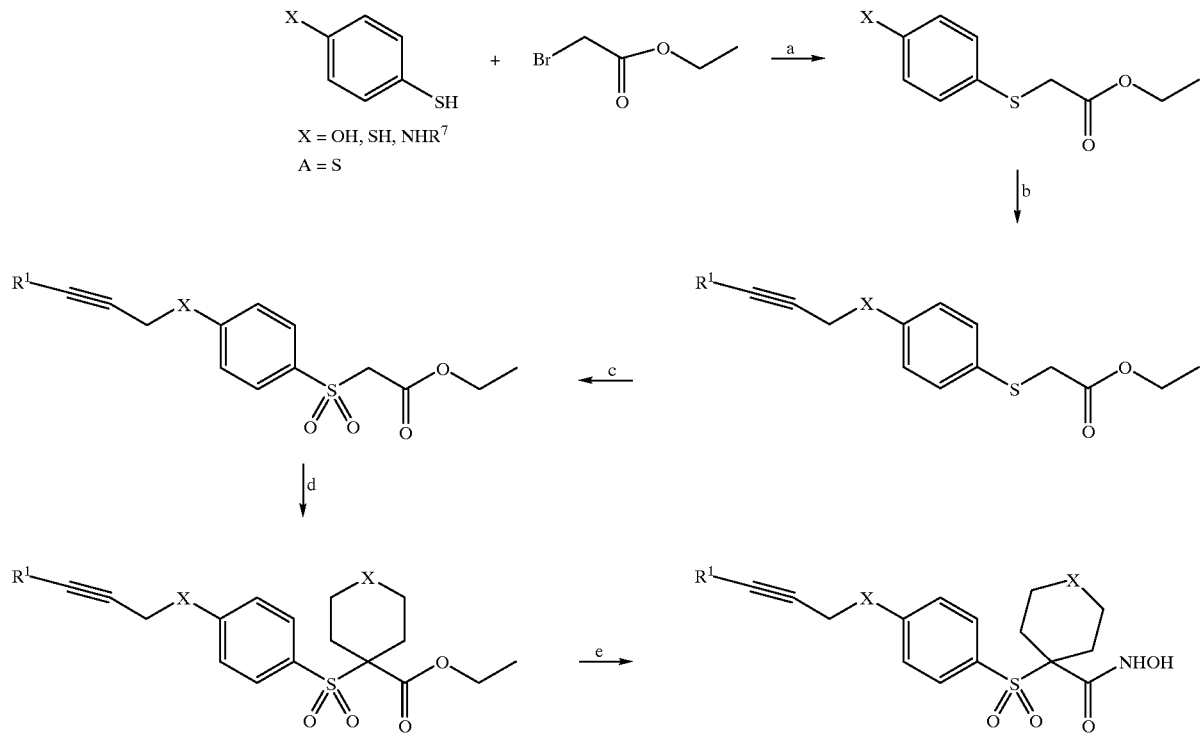

a. Diisopropylethyamine/CHCl₃/RT/3 Hr; b. K₂CO₃/Acetone/Prpargyl bromide derivative; c. Oxone/MeOH:THF/THF/RT; d: K₂CO₃/18-Crown-6/(C₄H₉)₄NBr/Acetone/Bis-2-chloroethyl N-substituted amine derivative/Reflux; e: NaOH/THF:MeOH/RT and (COCl)₂/NH₂OH.HCl/Et₃N/THF/DMF.

Bis-2-chloroethyl N-substituted amines can be prepared from the substituted diethanolamine and thionyl chloride. (Scheme 2). The cyclic product obtained by the above mentioned operation, can be hydrolyzed to carboxylic acid and subsequently converted to the hydroxamic acid as outlined in scheme 1.

SCHEME 2

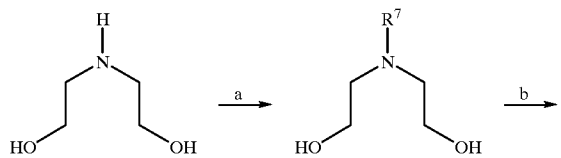

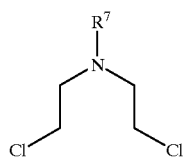

a: Diisopropylethylamine/R⁷Br/CHCl₃/Reflux; b: SOC₂/CH₂Cl₂/Reflux

The corresponding sulfides and sulfoxides can be prepared starting from the corresponding saturated heterocyclic carboxylic acid derivative. (Scheme-3). N-Boc protected isonipecotic acid can be lithiated using tert-butyllithium and the resulting anion was reacted with appropriately substituted disufides. The sufide derivative can be converted to hydroxamic acids by the procedure outlined above.

SCHEME 3

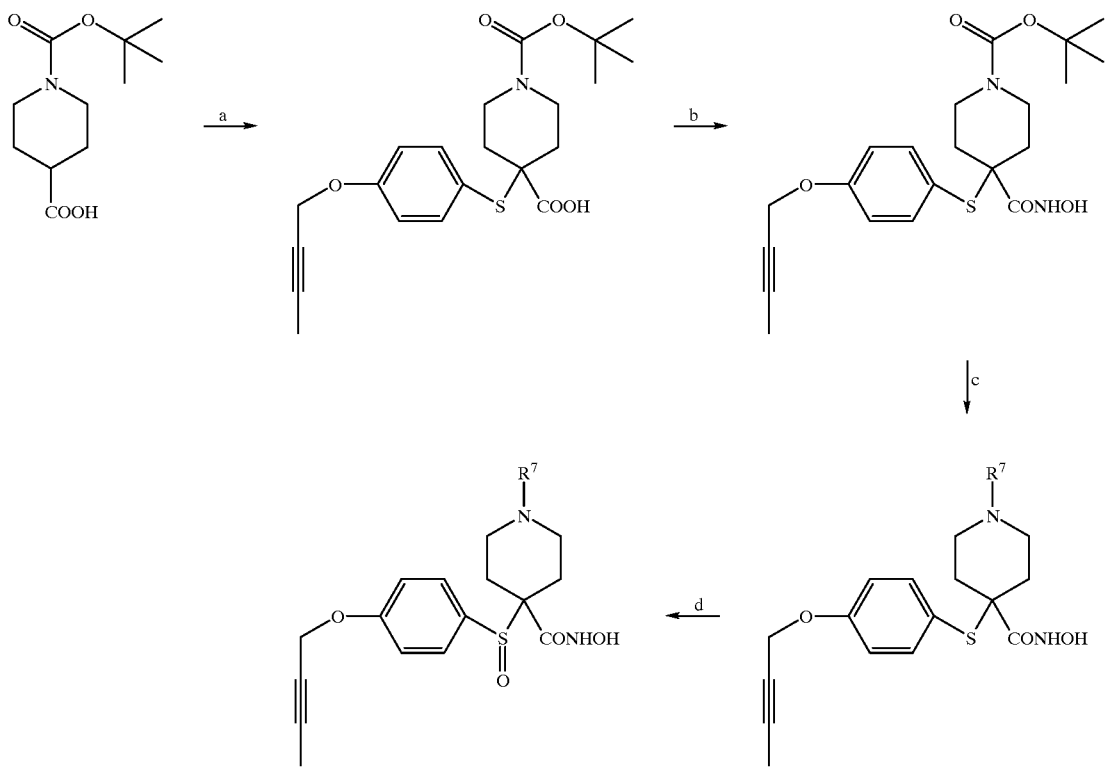

a: tert-Butyllithium/−78° C./THF/Bis(4-but-2-ynyloxyphenyl)disufide; b: (COCl)$_2$/NH$_2$OH.HCl/Et$_3$N/DMF/CH$_2$Cl$_2$; c: 1.HCl/Dioxane; c: 2:R$_7$Br/Et$_3$N; d: MeOH/30% H$_2$O$_2$ These sulfides subsequently can be converted to the sulfoxides using 30% hydrogen peroxide at room temperature. The required disulfides can be prepared from the appropriately substituted thiol and DMSO/HCl oxidation. This procedure can be applied to any saturated, fused or non-fused heterocyclic carboxylic acid derivative. (Scheme 4)

a: tert-Butyllithium/−78° C./THF/Bis(4-but-2-ynyloxyphenyl)disufide; b: (COCl)$_2$/NH$_2$OH.HCl/Et$_3$N/DMF/CH$_2$Cl$_2$; c: CH$_2$Cl$_2$/HCl/MeOH/R$^7$Br/Et$_3$N; d: MeOH/30% H$_2$O$_2$; e: Oxone/MeOH/THF/Rt.

Alternatively, sulfone derivatives can also be lithiated and carbonylated using either dry ice or CO$_2$ gas. (Scheme 5). The sulfone derivative can be a mono heterocyclic, bicyclic, benzo fused or hetero aryl such as pyridyl, thienyl, furanyl, pyrazinyl, pyrimidyl, thiazolyl fused ring systems.

SCHEME 4

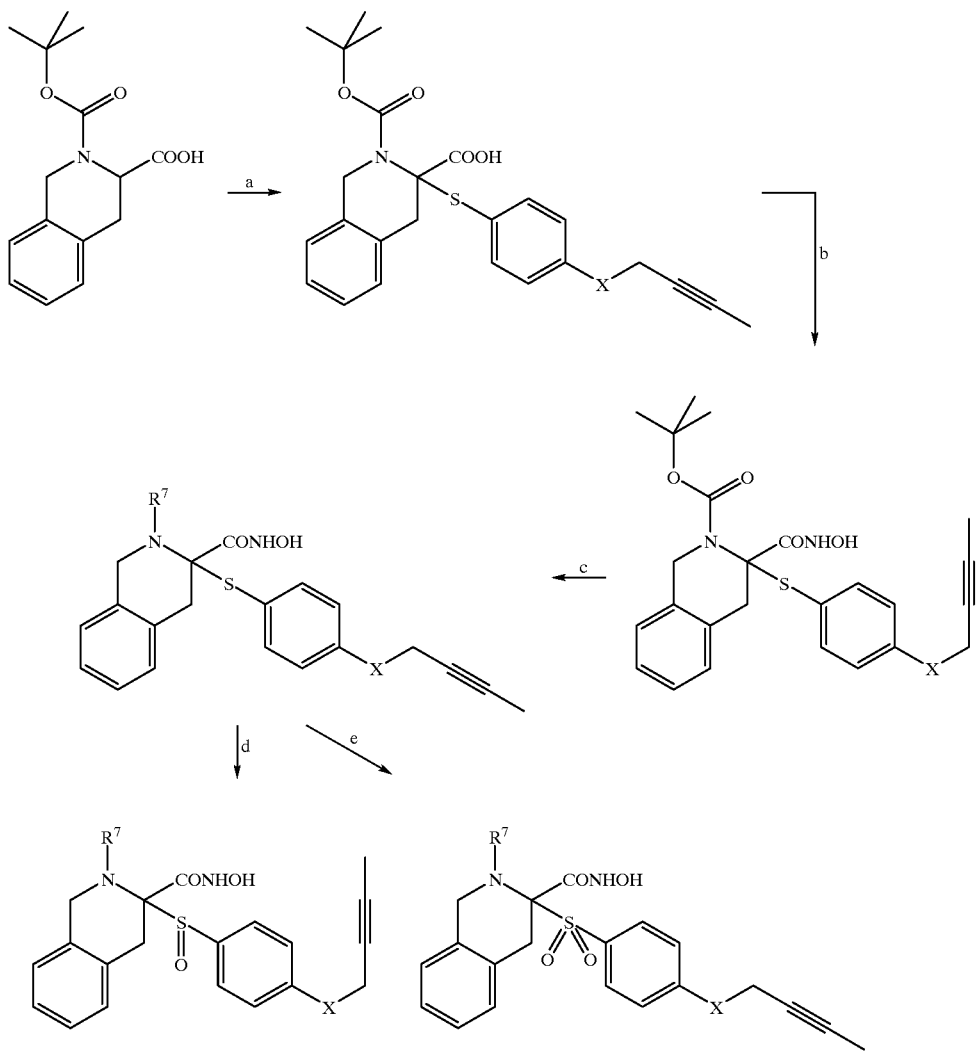

SCHEME 5

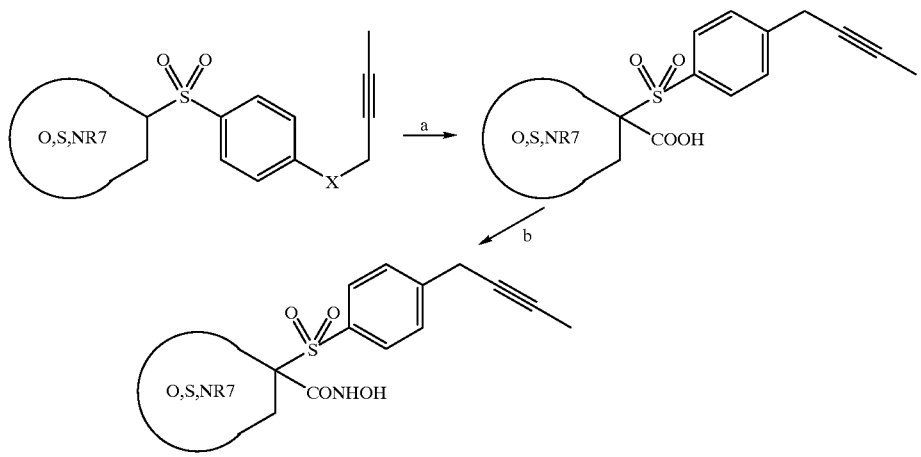

a: n-Butyllithium and quench with $CO_2$; b: $(COCl)_2$/ DMF/$NH_2OH\cdot HCl$/$Et_3N$ The oxygen analogue can be prepared (Scheme 6) from the appropriately substituted alkynyloxy-benzenesulfonyl acetic acid ethyl ester and 2-chloroethyl ether. The corresponding pyran derivative can be hydrolyzed to carboxylic acid, which can be converted to the hydroxamic acid derivative.

hydroxy, thiol or substituted amino moiety may be alkylated with acetylenes 2, where J is a suitable leaving group such as halogen mesylate, tosylate, or triflate to give 3. Acetylenes 2 are commercially available or known compounds, or they may be synthesized by known methods by those skilled in the art. The sulfonic acid salts 3 may be converted into the corresponding sulfonyl chloride or other sulfonylating agent 4 by known methods, such as reaction with oxalyl chloride,

SCHEME 6

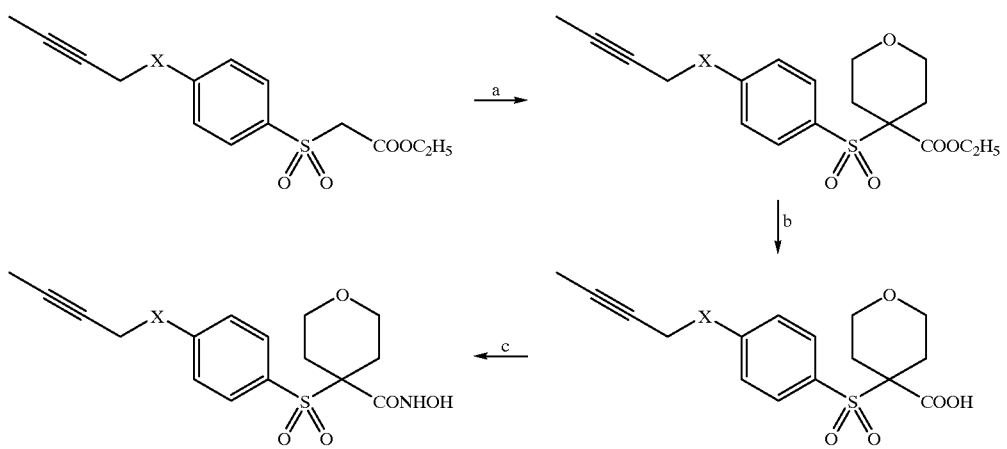

a: 2-Chloroethyl ether/$K_2CO_3$/18-Crown-6/n-$(C_4H_9)_4$Br/Acetone/Reflux;
b: 10N. NaOH/THF/MeOH/RT;
c: $(COCl)_2$/DMF/$NH_2OH\cdot HCl$/$Et_3N$.

The thiols used as intermediates for the synthesis of compounds of the invention can be made according to Scheme 7. Thus, sulfonic acid salts 1, where $XR_{50}$ is a phosphorus oxychloride or other reagent compatible with substituents $R_1$, $R_2$, and $R_3$ and the acetylene. The sulfonyl chloride 4 can then be reduced to the corresponding thiol 5 using triphenylphosphine in a suitable solvent mixture such as dichloromethane/DMF at a temperature of between −20° C. and 30° C.

SCHEME 7

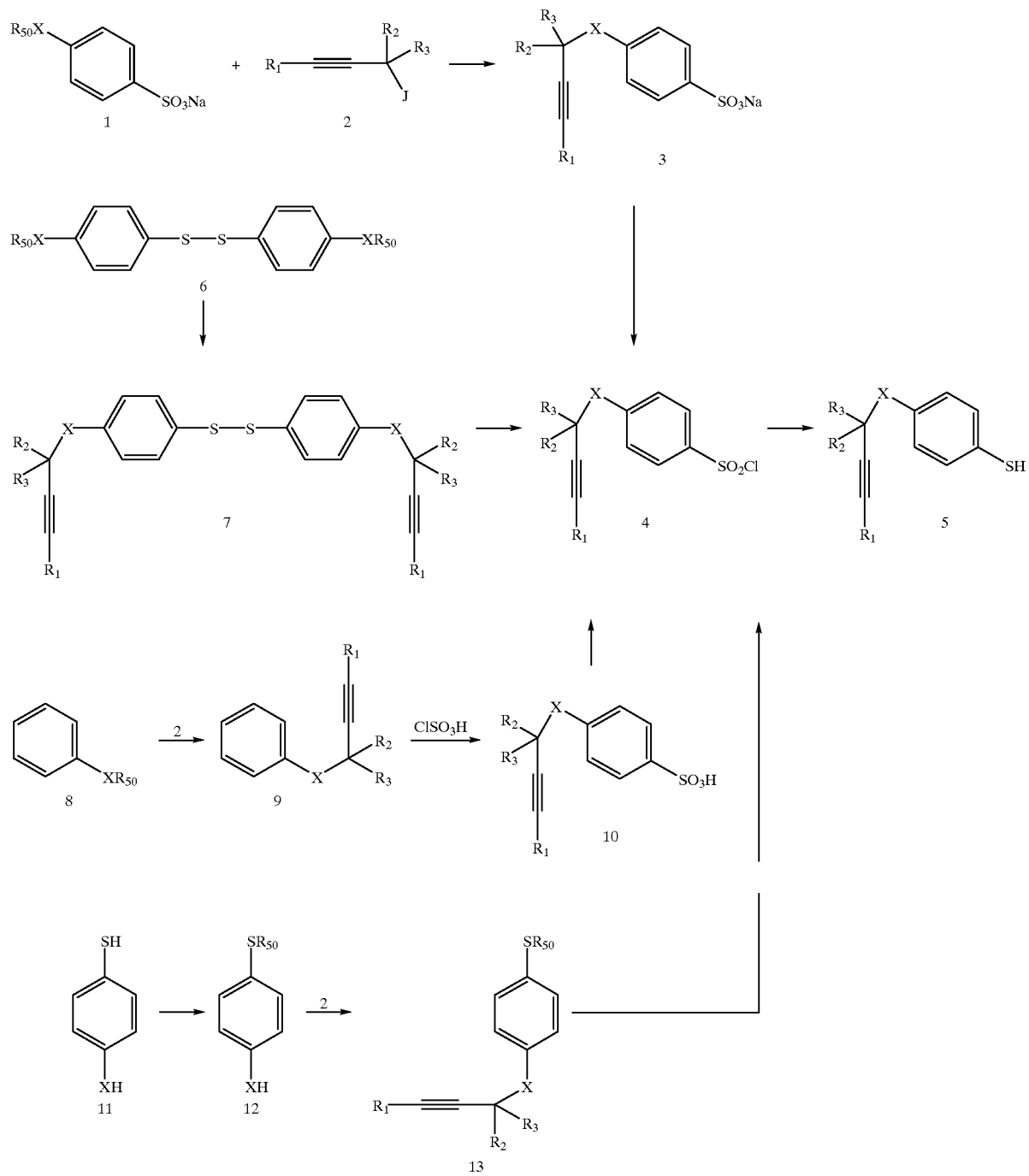

Alternatively, disulfide 6 may be converted into di-acetylene 7 by reaction with compounds 2, followed by reduction of the disulfide bond to provide the desired thiols 5. Bisacetylenes 7 may also be converted into thiols 5 via sulfonyl chlorides 4. Alkylation of the phenol, thiophenol, aniline or protected aniline 8 with 2 to give 9, followed by reaction with chlorosulfonic acid provides sulfonic acids 10 which are readily converted into 4 with oxalyl chloride or similar reagents and subsequently reduced to thiols 5. Thiophenols 11 are also precursors to 5 via protection of the thiol 5 with a triphenylmethyl or other suitable protecting group, alkylation of XH, where X is O, N or S, and deprotection of the sulfur.

SCHEME 8

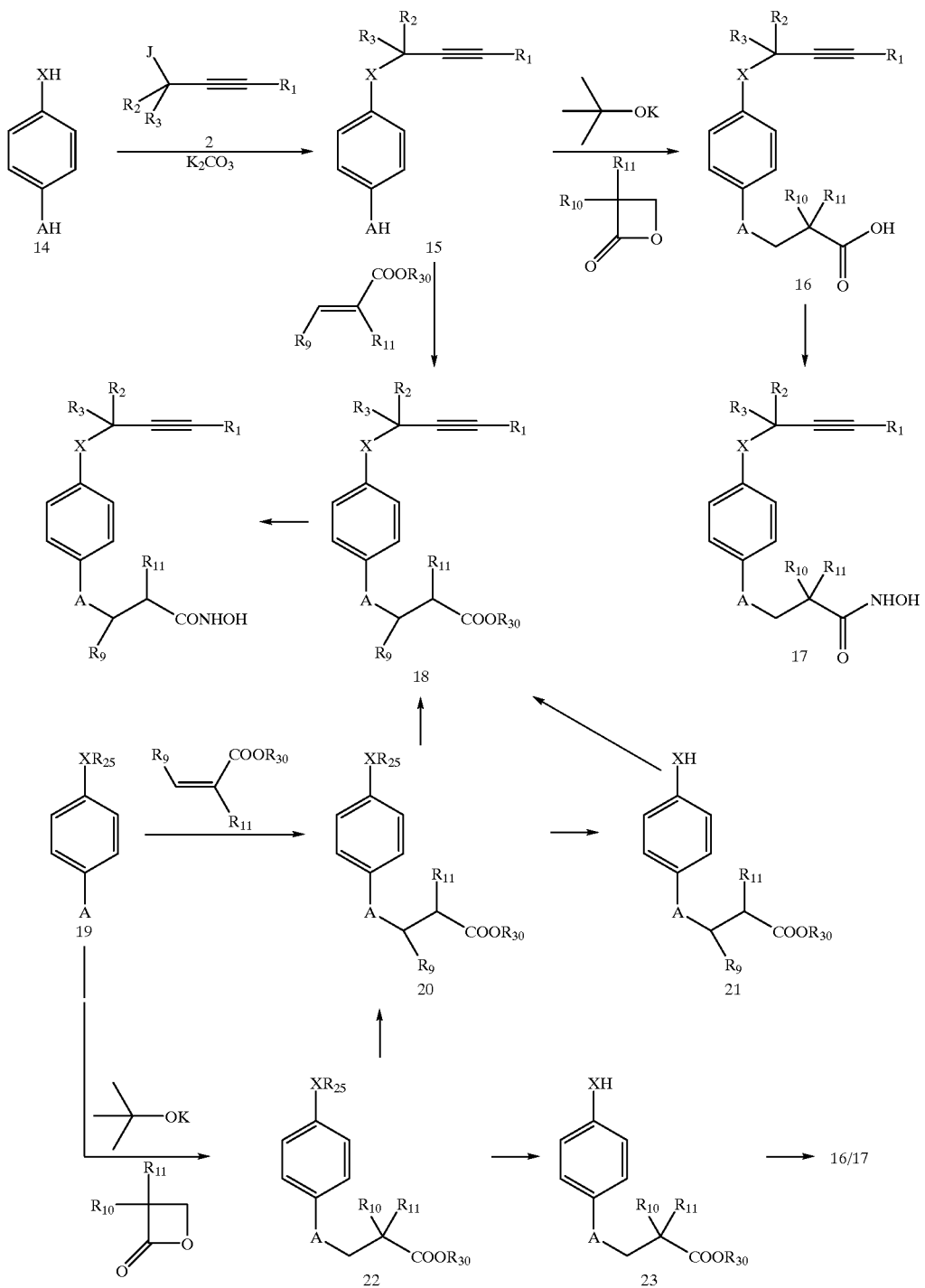

Compounds of the invention wherein X is N, O, S, SO or SO$_2$, can be synthesized according to Scheme 8 and Scheme 9. Alkylation of the para-disubstituted aryl 14, or its protected equivalent, with acetylene 2 in the presence of a base such as potassium carbonate in a polar aprotic solvent such as acetone or DMF at a temperature of between 20° C. and 120° C. provides the mono-propargylic ether 15. Those skilled in the art will recognize that protecting groups may be required to avoid undesirable side reactions and increase the yield of the reaction. The need and choice of protecting group for a particular reaction is known to those skilled in the art. Reaction of this compound with .-propiolactone, or a substituted propiolactone derivative (wherein the substituents are defined as before), in the presence of a base such as potassium t-butoxide in a polar solvent, or solvent mixture, such as THF or DMF affords the carboxylic acid 16. Conversion of carboxylic acid 16 into the corresponding hydroxamic acid, 17, is accomplished via formation of an activated ester derivative such as an acid chloride or acid anhydride followed by reaction with hydroxylamine. It is understood by those skilled in the art that when A is sulfur, in Scheme 8 and all relevant subsequent Schemes, the sulfur can be oxidized to the corresponding sulfoxide or sulfone at any stage after formation of the thioether, using a suitable oxidant such as oxone, air, m-chloroperbenzoic acid or hydrogen peroxide.

Compounds 18 are also accessible from the Michael addition of compound 15 to a cyclic acrylate ester, or substituted acrylate ester (substituents are defined as before), to provide 18, in which $R_{30}$ is hydrogen or a suitable carboxylic acid protecting group. Deprotection of the ester moiety then provides carboxylic acid, which can be converted into the analogous hydroxamic acid. Similarly, Michael addition of mono-protected 1,4-disubstituted aryl 19, where $XR_{25}$ is hydroxy or protected hydroxy, thiol or amine, gives compound 20. Unmasking of the protecting group gives thiol, aniline or phenol 21 which can be alkylated with propargyl derivative 2 to provide 18. Mono protected compound 19 can also be reacted with β-propionolactone to provide 22. Alternatively, 22 can be deprotected followed by alkylation to give 16 and 17.

Synthesis of compounds of the invention wherein X is N, O, S, SO or $SO_2$, and the linker between the proximal heteroatom and the hydroxamic acid is a one or three carbon chain can be synthesized according to Scheme 9. Compound 19, where $XR_{25}$ is hydroxy or protected hydroxy, thiol or amine, can react with ester 24 or lactone 24a, in which $R_{30}$ is hydrogen or a suitable carboxylic acid protecting group, with an appropriately substituted leaving group such as halogen, tosylate, mesylate or triflate, to provide 25. Unmasking of the heteroatom X of compound 25 then provides 26, which may next be alkylated with propargylic derivative 2 to give acetylene-ester 27. Ester 27 can be converted into the corresponding hydroxamic acid 28 through conversion of the ester into the carboxylic acid by acid or base hydrolysis, followed by conversion into the hydroxamic acid as described in Scheme 1. Alternatively, compound 15, prepared as shown in Scheme 8, can be alkylated directly with ester 24 or lactone 24a to give 27 and then 28. Substituents on the carbon alpha to the hydroxamic are defined as before.

SCHEME 9

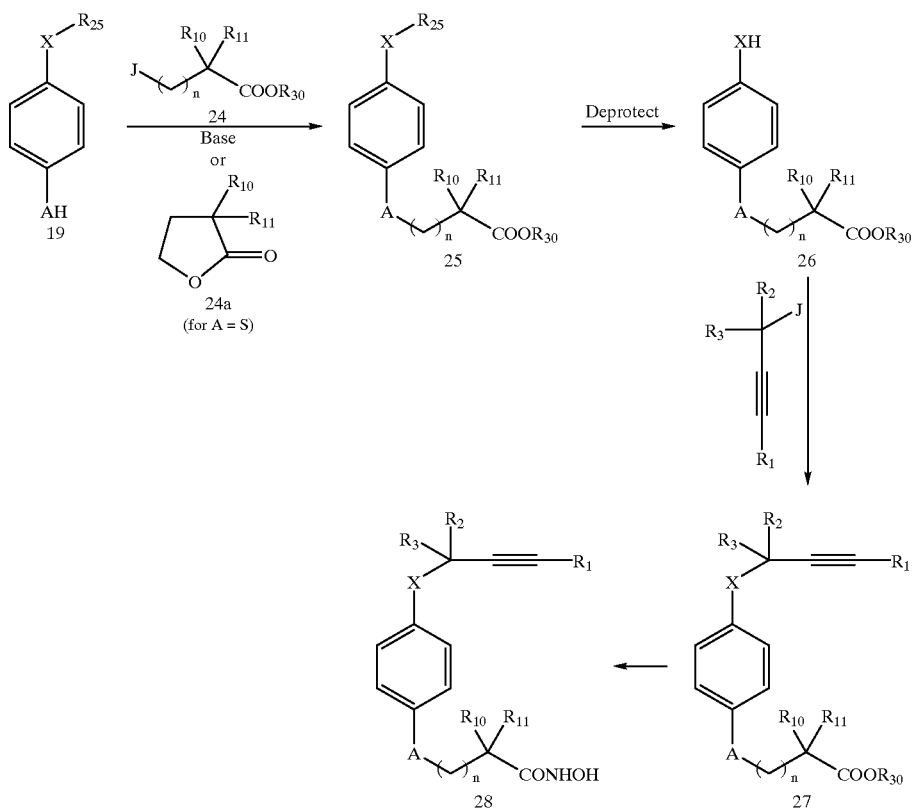

-continued

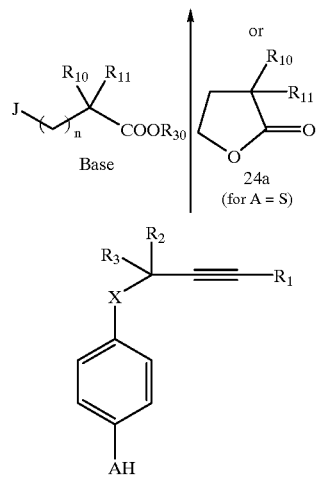

Compounds of the invention wherein A is a methylene or substituted methylene group, and X is oxygen, can be obtained according to Scheme 10. Esters or carboxylic acids 29, commercially available or known in the literature, can be converted into the corresponding phenols, 30. Alkylation of the phenol with acetylene 2 gives the propargylic ethers, 31, which can be converted into the corresponding carboxylic acids and thence the hydroxamic acids, 33, as described in Scheme 1. Substituents on the carbon alpha to the hydroxamic, are defined as before.

Compounds of the invention wherein A is —SO$_2$—, and R$_8$ and R$_9$ are not hydrogen, are available starting from 4-fluorobenzenethiol 34 as shown in Scheme 11. Deprotonation of the thiol followed by reaction with .-propiolactone, or an acrylate ester, or ester deriavtive 24, and subsequent oxidation of the resulting thioether provides sulfone-acid 35. Displacement of the 4-fluoro substituent of 35, or its corresponding ester, with propargyl derivative 36, wherein X is N, O or S, then provides sulfone 16. Compound 16 can be converted into the compounds of the 15 invention according to Scheme 1. Fluoroaryl 35 can also react with a masked hydroxyl, thiol or amino group (HXR$_{40}$, wherein R$_{40}$ is a suitable protecting group) in the presence of a base such as sodium hydride in a polar aprotic solvent such as DMF to provide 36. Deprotection of 36 followed by alkylation with acetylenic derivative 2 then gives 16.

SCHEME 10

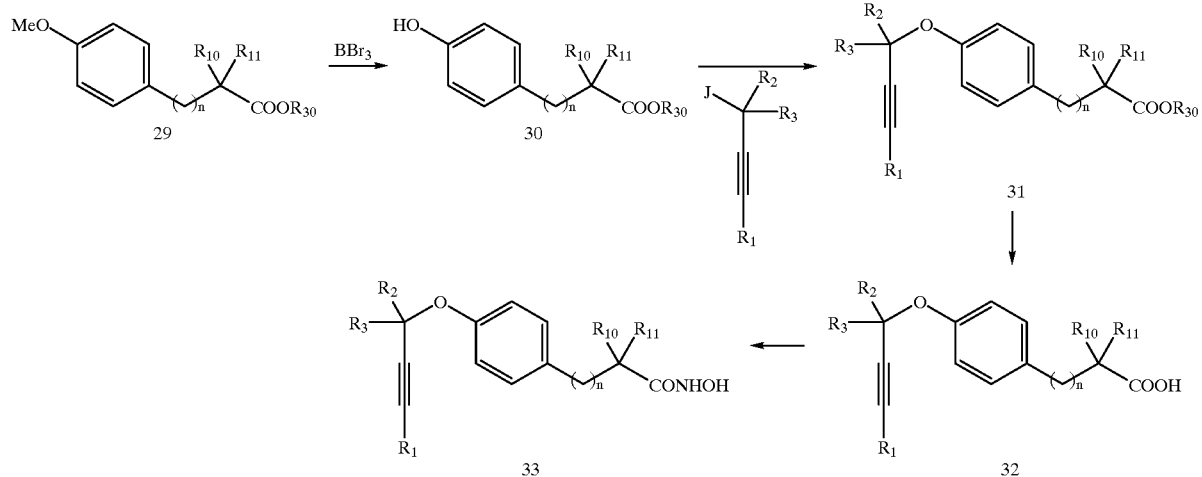

SCHEME 11

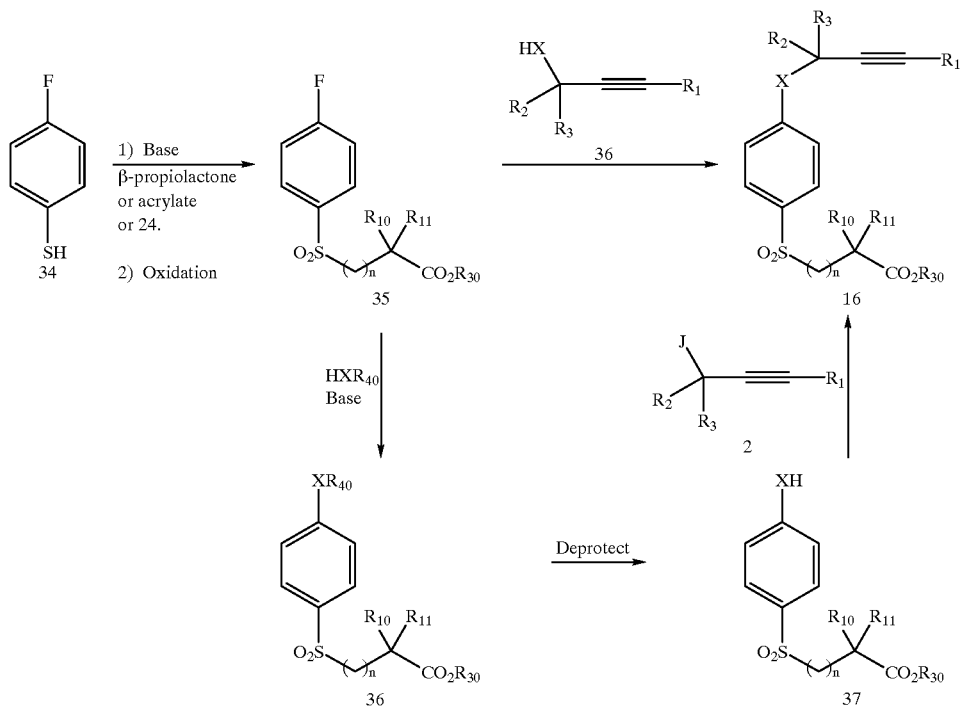

Compounds of the invention wherein X is NH are also available starting from the appropriate commercially available nitro aryl compound 38 (Scheme 12). Thus, the anion of compound 38 can be used to alkylate β-propiolactone, or a substituted derivative, or a cyclic acrylate ester to provide 40 and 39 respectively. Reduction of the nitro group followed by alkylation of the resulting aniline then gives 16. Compound 38 can also be alkylated with ester derivative 24 to afford nitro-ester 40, followed by reduction to give the corresponding aniline, analogous to compound 26 of Scheme 9.

SCHEME 12

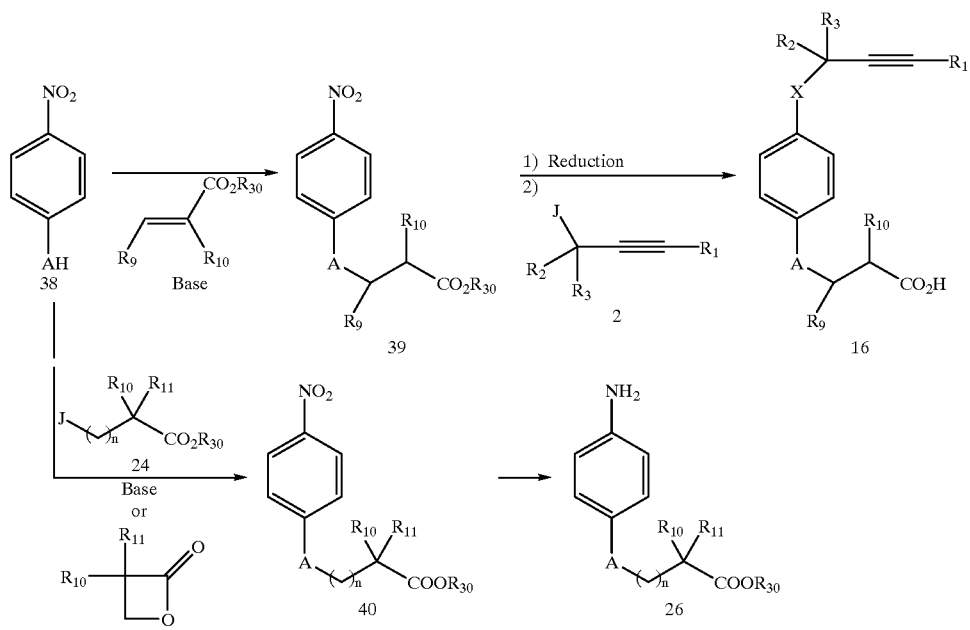

Compounds of the invention wherein $R_{11}$, alpha to the hydroxamic acid, is a hydroxy group can be obtained via epoxides 41, as shown in Scheme 13. These epoxides are available through the oxidation of the corresponding acrylate esters or by the Darzens reaction of an alpha-halo ester with a ketone. Reaction of the epoxide with thiol, phenol or aniline 19 in the presence of base or Lewis acid catalyzed epoxide ring opening, provides alpha-hydroxy ester 42. Deprotection of 42 followed by alkylation with propargyl derivative 2 gives 44. Conversion of the ester of 44 into the analogous hydroxamic acid as described in Scheme 1 then provides 45. Compounds 45, wherein A is sulfur, may be converted into the analogous sulfoxides or sulfones through oxidation with hydrogen peroxide, air, Oxone or other suitable reagent at this point. Similarly, thiol, phenol or aniline 15 can be reacted with 41 to give 44. The hydroxyl group of compound 43 can also be manipulated through its conversion into a suitable leaving group, such as halide or sulfonate ester, followed by displacement with various nucleophiles including amines to provide 44.

SCHEME 13

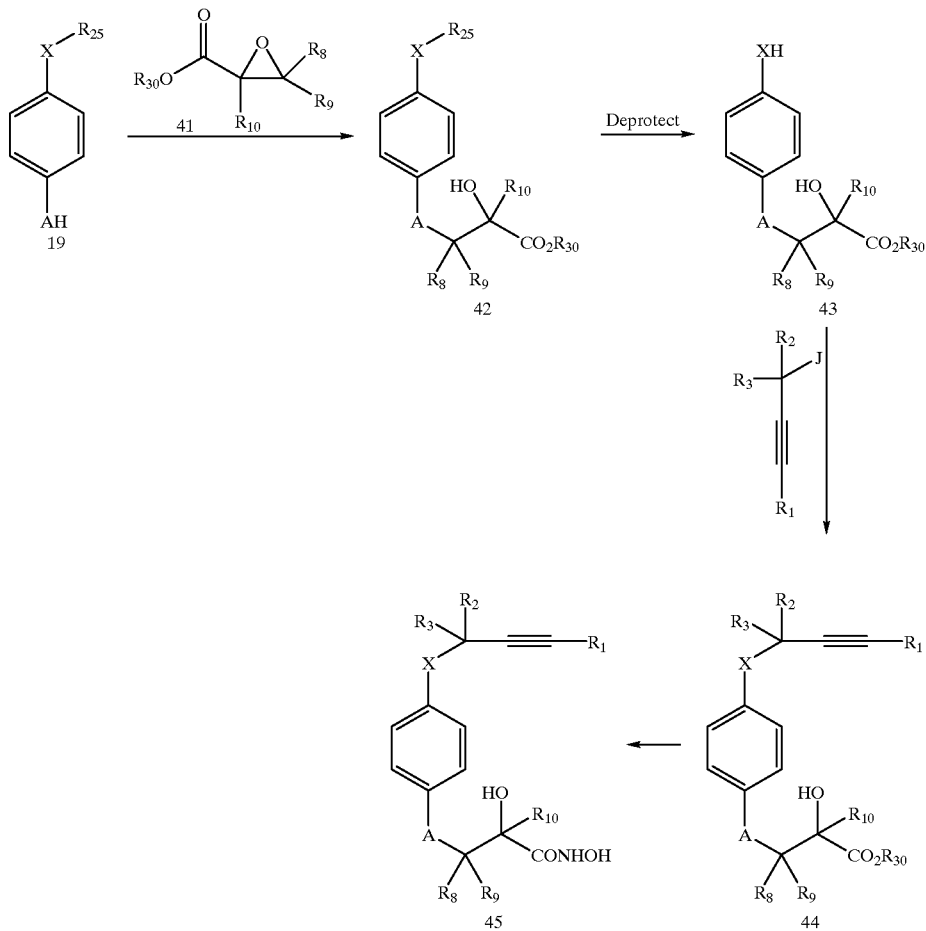

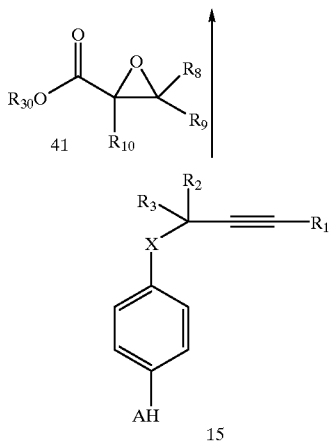

Another route to alpha-hydroxy hydroxamic acids of the invention is shown in Scheme 14. Compound 15 can be alkylated with alcohol 46 to give 47. Oxidation of the alcohol, with or without concomitant oxidation of the thioether (for A=S), gives the aldehyde 48. Reaction of aldehyde 48 with trimethylsilyl cyanide or other suitable reagent then provides the cyanohydrin 49. Hydrolysis of the nitrile 49 into the corresponding carboxylic acid followed by conversion into the hydroxamic acid as described in Scheme 1 gives 50.

SCHEME 14

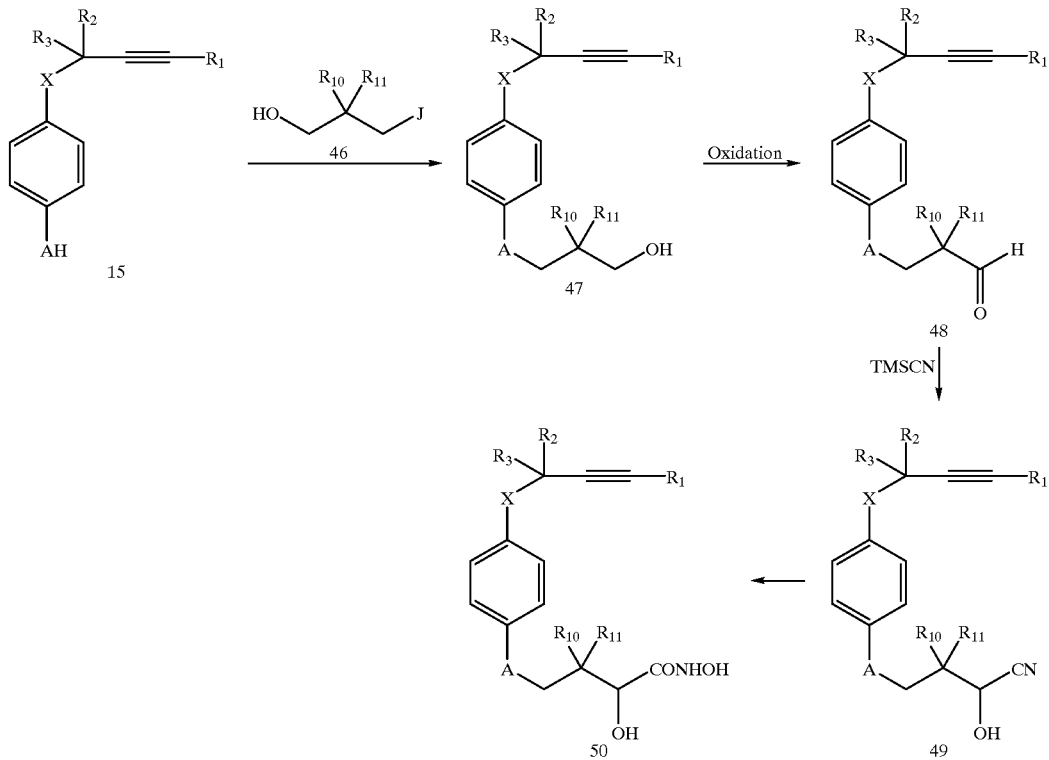

Compounds described in the present invention (from Example 30 to 63) were prepared as per the Schemes 15 and Scheme 16. In scheme 15, the t-Boc-protected ethyl isonipecotate 51 was carefully alkylated using diiodomethane to yield the monoiodo compound 52. This was subsequently converted to different hydroxamic acid derivatives as depicted in Scheme 15. In scheme 16, the N-Boc group was selectively removed using TMSOTf/2,6-Lutidine. After the derivatisation of the nitrogen, the O-tBu was removed using TFA in methylene chloride.

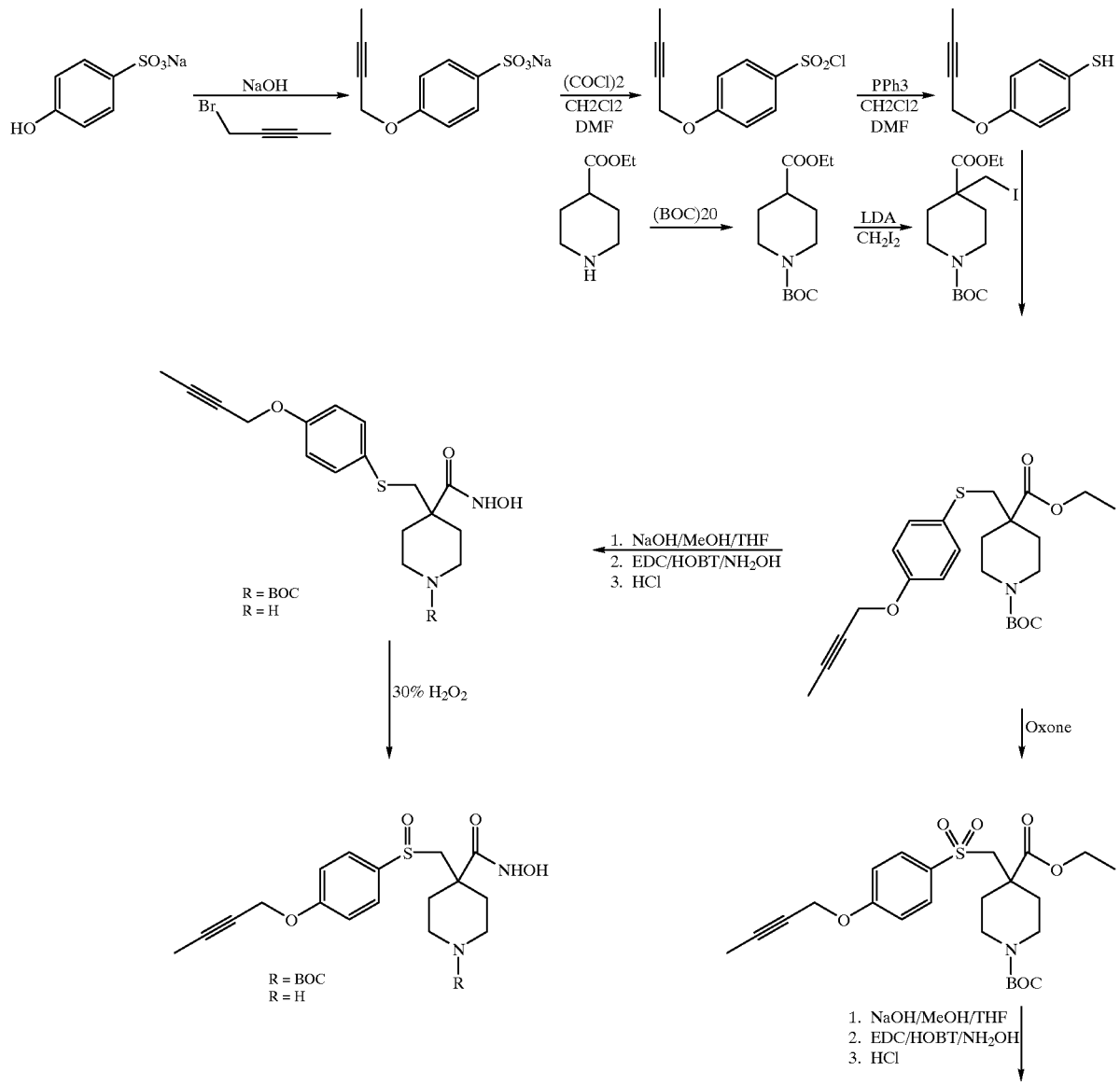

SCHEME 15

-continued
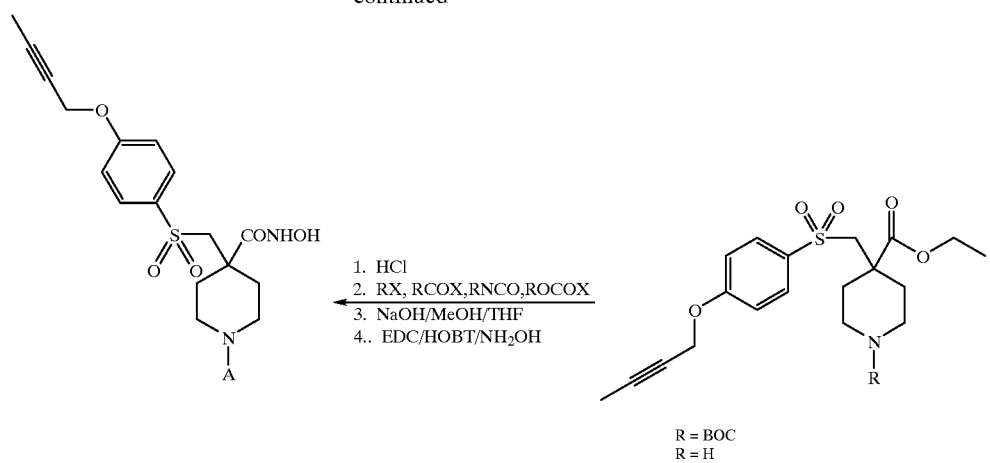
Scheme 16
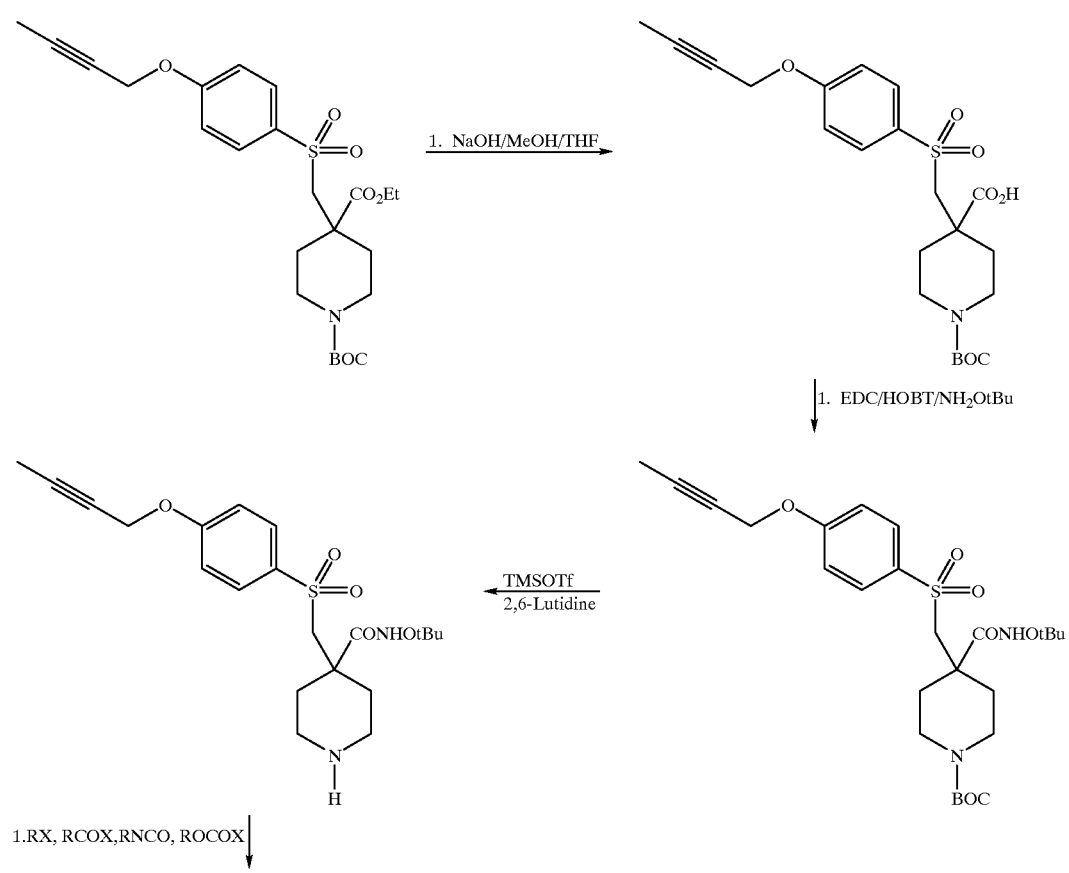

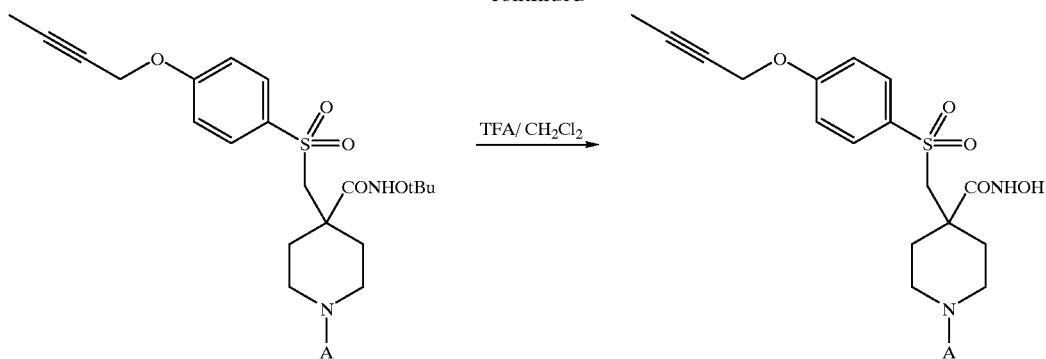
Alternatively, compounds (wherein A=SO$_2$ and n=0) described in examples 64 to 74 and 80 were prepared as depicted in Scheme 17.
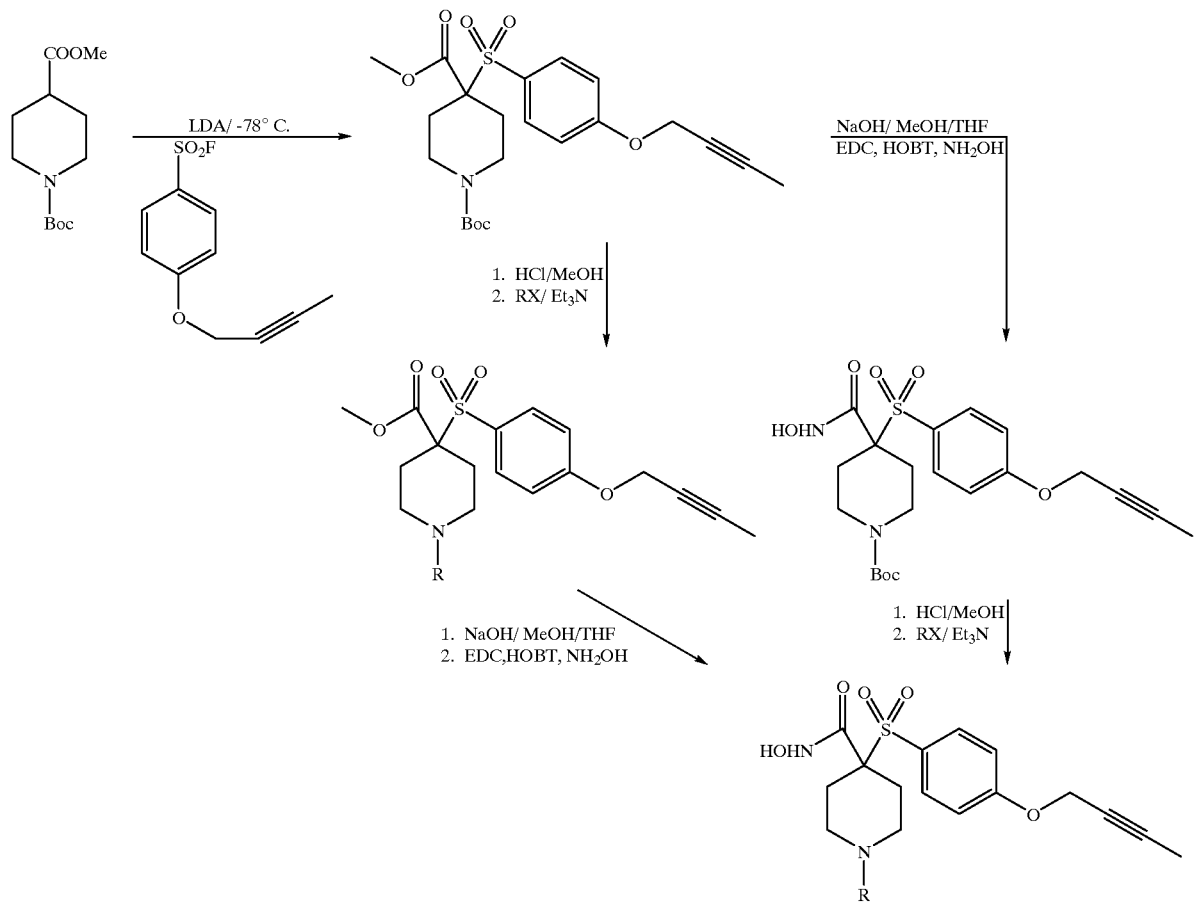

Experimental

EXAMPLE 1

1-(4-Bromo-benzyl)-4-(4-but-2-ynyxoy-benzenesulfonyl)-piperdine-4-carboxylic acid hydroxyamide Step 1

To a stirred solution of 4-mercapto phenol (12.6 g. 100 mmol) and N,N-diisopropylethylamine (13.0 g, 100 mmol) in chloroform (200 ml), ethyl bromoacetate (17.0 g, 100 mmol) in chloroform (30 ml) solution was added slowly at room temperature. After the addition was complete, the reaction mixture was refluxed for 1 hr and cooled to room temperature. The reaction mixture was washed well with water, dried over anhydrous $MgSO_4$; filtered and concentrated. The oily product obtained was taken to next step without purification.

Step 2

A mixture of $K_2CO_3$ (15 gm, excess), (4-hydroxy-phenylsulfanyl)-acetic acid ethyl ester (5 g, 23.6 mmol) and 1-bromo-2-butyne (9.34 g, 35.4 mmol) was refluxed with stirring for 8 hrs. The reaction mixture was then cooled to room temperature and filtered. The filtrate was concentrated and extracted with chloroform. The chloroform layer was washed with water, dried over anhydrous $MgSO_4$, filtered and concentrated. The product obtained was taken to next step with out purification. Yield 6.0 g (96%); yellow oil; MS: 264.0 EI $(M^+H)$.

Step 3

To a stirred solution of (4-but-2-ynyloxy-phenyl sulfanyl)-acetic acid ethyl ester (101 g, 380 mmol) in MeOH:THF (3:1) (1000 ml), Oxone (670.0 g, excess) in water (1000 ml) was added at room temperature. The reaction mixture was stirred at room temperature for 8 hrs. The reaction mixture was then diluted with chloroform (600 ml) and filtered. The organic layer was separated and washed once with a saturated solution of $NaHSO_3$ (400 ml). The chloroform layer was washed well with water, dried and concentrated. The oily product was dissolved in MeOH (100 ml) and hexane (600 ml) was added. The separated colorless solid was filtered and washed with hexane. Yield 108 g (96%); mp. 91–93° C.; MS: 297 $(M^+H)^+$.

Step 4

A mixture of diethanolamine (22.5 g, 150 mmol), 4-bromobenzyl bromide (25 g, 100 mml) and N,N-diisopropylethylamine (19.0 g, 150 mmol) was refluxed for 24 hrs in chloroform (500 ml) solution. The reaction mixture was then concentrated and the residue was extracted with chloroform. It was washed well with water, dried over anhydrous $MgSO_4$, filtered and concentrated. The crude product obtained was taken to next step with out purification. Yield 33.6 g (99%); Yellow oil, MS: 273.8 $(M^+H)^+$.

Step =

2-[(4-Bromobenzyl)-(2-hydroxy-ethyl)-amino]-ethanol (33.28 g, 122 mmol) was dissolved in methanolic hydrogen chloride (100 ml) at 0° C. Methanol was removed in vacuo and the hydrochloride salt was suspended in $CH_2Cl_2$ (300 ml). To a stirred solution of the above mentioned suspension, thionyl chloride (30 g, excess) was added slowly at room temperature. The reaction mixture was brought to gentle reflux for 3 hrs. The reaction mixture was then concentrated and the (4-bromo-benzyl)-bis-(2-chloro-ethyl)-amine was used in the next step with out purification. Yield: 47 g (99%); brown solid; mp 125° C.; MS: 309.8 $(M^+H)^+$.

Step 6

A stirred mixture of anhydrous $K_2CO_3$ (10 g, excess), 18-crown-6 (1 g), tetrabutylammonium bromide (1.0 g), (4-but-2-ynyloxy-benzenesulfonyl)-acetic acid ethyl ester (2.8 g, 9.46 mmol) and (4-bromo-benzyl)-bis-(2-chloro-ethyl)-amine (4.9 g, 14.2 mmol) in anhydrous acetone (200 ml) was refluxed for 24 hrs. The reaction mixture was then cooled and filtered and the filtrate was concentrated. The crude product was extracted with chloroform, washed well with water, dried and concentrated. The brown colored material was purified by column chromatography on silica gel by eluting with 50% ethylacetate:hexane. Yield 1.36 g (27%); brown oil; MS: 534 $(M+H)^+$ Step 7

1-(4-Bromo-benzyl)-4-(4-but-2-ynyloxy-benzenesulfonyl)-piperdine-4-carboxylic acid was prepared starting from 1-(4-bromo-benzyl)-4-(4-but-2-ynyloxy-benzenesulfonyl)-piperdine-4-carboxylic acid ethyl ester (1.36 g, 2.54 mmol) dissolved in THF:methanol (100:50 ml) and 10 N NaOH (15 ml). The reaction mixture was stirred at room temperature for 24 hrs. The reaction mixture was then concentrated and residue was cooled and neutralized with concentrated HCl. The separated solid was extracted with chloroform:methanol (3:1) (300 ml) and washed with water. The chloroform layer was dried and concentrated. The product was crystallized from methanol. Yield 800 mg (62%); off white solid; mp 197° C.; MS: 507.9 $(M+H)^+$ Step 8

To a stirred solution of 1-(4-bromo-benzyl)-4-(4-but-2-ynyxoy-benzene-sulfonyl)-piperdine-4-carboxylic acid (750 mg, 1.5 mmol) and DMF (1 ml) in $CH_2Cl_2$ (100 ml), oxalyl chloride (508 mg, 4.0 mmol) in methylene chloride (2 ml) was added dropwise at 0° C. After the addition, the reaction mixture was warmed to room temperature and stirred for 1 hr. The acid chloride thus formed was concentrated to remove excess oxalyl chloride and redissolved in $CH_2Cl_2$ (30 ml). In a separate flask, hydroxylamine hydrochloride (690 mg, 10 mmol) was dissolved in DMF (10 ml) and triethylamine (10 g, 10 mmol) was added. The reaction mixture was further diluted with acetonitrile (25 ml) and stirred at 0° C. The acid chloride was slowly added into the hydroxylamine and after the addition was complete, the reaction mixture was brought to room temperature and stirred for 24 hrs. The reaction mixture was concentrated and the residue was extracted with chloroform, washed well with water and dried over anhydrous $Na_2SO_4$. The product was purified by silica gel column chromatography by eluting it with 10% methanol:ethyl acetate. 270 mg of 1-(4-bromo-benzyl)-4-(4-but-2-ynyloxy-benzenesulfonyl)-piperdine-4-carboxylic acid hydroxyamide was isolated as a hydrochloride salt, a white powder. Yield 52%; mp 153° C.; MS: 522.9 $(M+H)^+$; $^1H$ NMR (300 MHz, DMSO-$d_6$): δ1.85 (t, J=2.04 Hz, 3H), 2.23 (m, 2H), 2.49 (m, 2H), 2.83 (m, 2H), 3.36 (m, 2H), 4.28 (s, 2H) 4.89 (d, J=2.2 Hz, 2H), 7.18 (d, J=9 Hz, 2H), 7.47 (d, J=8.1 Hz, 2H), 7.68 (m, 4H) 9.37 (s, 1H), 10.25 (s, 1H)

EXAMPLE 2

4-(4-But-2-ynyloxy-benzenesulfonyl)-1-(4-methoxy-benzyl)-piperdine-4-carboxylic acid hydroxyamide 2-[(2-Hydroxy-ethyl)-(4-methoxy-benzyl)-amino]-ethanol was prepared according to the general method as outlined in Example 1 (Step 4). Starting from diethanolamine (10.5 g, 100 mmol). and 4-methoxy benzyl chloride (15.6 g, 100 mmol). Yield 21 g, (98%); yellow oil; MS: 226 $(M+H)^+$ Bis-(2-chloro-ethyl)-(4-methoxy-benzyl)-amine was prepared according to the general method as outlined in Example 1 (Step 5). Starting from 2-[(2-hydroxy-ethyl)-(4- methoxy-benzyl)-amino]-ethanol (11.2 g, 50 mmol). Yield 14 g, (99%); dark brown low melting solid; MS: 263 (M+H)+

4-(4-but-2-ynyloxy-benzenesulfonyl)-1-(4-methoxy-benzyl)-piperidine-4-carboxylic acid ethyl ester was prepared according to the general method as outlined in Example 1. Starting from (4-but-2-ynyloxy-benzenesulfonyl)-acetic acid ethyl ester (2 g, 6.73 mmol) and bis-(2-chloro-ethyl)-(4-methoxy-benzyl)-amine (2.61 g, 8.75 mmol) and following the procedure as outlined in Example 1 (Step 6) 2.5 g of the product was isolated. Yield 2.5 g (77%); yellow oil; MS: 486 (M+H)+

4-(4-But-2-ynyloxy-benzenesulfonyl)-1-(4-methoxy-benzyl)-piperdine-4-carboxylic acid was prepared starting from 4-(4-but-2-ynyloxy-benzenesulfonyl)-1-(4-methoxy-benzyl)-piperidine-4-carboxylic acid ethyl ester (2.5 g, 5.15 mmol) dissolved in THF:methanol (3:1, 200 ml) and 10 N NaOH (15 ml). The resulting reaction mixture was worked up as outlined in Example 1 (Step 7). Yield 1.26 g (54%); off white solid; mp 223° C.; MS: 458 (M+H)+

Starting from 4-(4-but-2-ynyloxy-benzenesulfonyl)-1-(4-methoxy-benzyl)-piperdine-4-carboxylic acid (1 g, 2.19 mmol) and following the procedure as outlined in Example 1, (Step 8), 350 mg of 4-(4-but-2-ynyloxy-benzenesulfonyl)-1-(4-methoxy-benzyl)-piperdine-4-carboxylic acid hydroxyamide was isolated as a hydrochloride salt, an off white solid. Yield 31%; mp 162° C.; MS: 473 (M+H)+; 1H NMR (300 MHz, DMSO-$d_6$): δ1.86 (t, J=2.13 Hz, 3H), 2.23 (m, 2H), 2.49 (m, 2H), 2.73 (m, 2H), 3.39 (m, 2H), 3.77 (s, 3H), 4.21 (d, J=4.26 Hz, 2H), 4.89 (d, J=2.28 Hz, 2H), 6.99 (d, J=8.7 Hz, 2H), 7.17 (d, J=9 Hz, 2H), 7.43 (d, J=8.4 Hz, 2H), 7.68 (d, J=9 Hz, 2H), 9.37 (s, 1H), 10.21 (s, 1H), 11.17 (s, 1H).

EXAMPLE 3

4-(4-But-2-ynyloxy-benzenesulfonyl)-1-(4-chloro-benzyl)-piperdine-4-carboxylic acid hydroxyamide 2-[(4-chlorobenzyl)-(2-hydroxy-ethyl)-amino]-ethanol was prepared according to the general method as outlined in Example 1 (Step 4). Starting from diethanolamine (14.3 g, 95 mmol). and 4-chlorobenzyl chloride (10.2 g, 63 mmol). Yield 12.1 g, (84%); yellow oil; MS: 230 (M+H)+

(4-Chloro-benzyl)-bis-(2-chloro-ethyl)-amine was prepared according to the general method as outlined in Example 1 (Step 5). Starting from 2-[(4-chlorobenzyl)-(2-hydroxy-ethyl)-amino]-ethanol (12 g, 52.4 mmol). Yield 41.27 g, (90%); yellow powder; mp 115° C.; MS: 303 (M+H)+

4-(4-But-2-ynyloxy-benzenesulfonyl)-1-(4-chloro-benzyl)-piperdine-4-carboxylic acid ethyl ester was prepared according to the general method as outlined in Example 1 (Step 6). Starting from (4-but-2-ynyloxy-benzenesulfonyl)-acetic acid ethyl ester (4 g, 13.5 mmol) and (4-chlorobenzyl)-bis-(2-chloro-ethyl)-amine (4.9 g, 16.2 mmol). Yield 3.5 g (53%); white crystals; MP 91.8° C.; MS: 490 (M+H)+

4-(4-But-2-ynyloxy-benzenesulfonyl)-1-(4-chloro-benzyl)-piperdine-4-carboxylic acid was prepared starting from 4-(4-but-2-ynyloxy-benzenesulfonyl)-1-(4-chloro-benzyl)-piperdine-4-carboxylic acid ethyl ester (3.14 g, 6.42 mmol) dissolved in THF:methanol 3:1 (100 ml) and 10 N NaOH (10 ml). The resulting reaction mixture was worked up as outlined in Example 1 (Step 7). Yield 2.37 g (80%); white solid; mp 205° C.; MS: 461.9 (M+H)+

Starting from 4-(4-but-2-ynyloxy-benzenesulfonyl)-1-(4-chloro-benzyl)-piperdine-4-carboxylic acid (2.31 g, 5.01 mmol) and following the procedure as outlined in Example 1 (Step 8), 790 mg of 4-(4-but-2-ynyloxy-benzenesulfonyl)-1-(4-chloro-benzyl)-piperidine-4-carboxylic acid hydroxyamide was isolated as a hydrochloride salt, a yellow solid. Yield 31%; mp 130° C.; MS: 476.9 (M+H)+; 1H NMR (300 MHz, DMSO-$d_6$): δ1.856 (s, 3H), 2.23 (m, 2H), 2.73–2.89 (m, 4H), 3.37 (d, 2H), 4.28 (m, 2H), 4.89 (d, 2H), 7.18 (d, J=8.94 Hz, 2H), 7.54 (s, 4H), (d, J=8.88 Hz, 2H), 9.40 (s, 1H), 10.3 (s, 1H).

EXAMPLE 4

1-Benzyl-4-(4-but-2-ynyloxy-benzenesulfonyl)-piperdine-4-carboxylic acid hydroxyamide Bis-(2-Chloro-ethyl)-benzyl amine was prepared according to the general method as outlined in Example 1 (Step 5). Starting from N-benzyldiethanolamine (164.6 g, 844 mmol). Yield 178.5 g (79%); brown solid; MS: 231.9 (M+H)+

1-Benzyl-4-(4-but-2-ynyloxy-benzenesulfonyl)-piperidine-4-carboxylic acid ethyl ester was prepared according to the general method as outlined in Example 1 (Step 6). Starting from (4-but-2-ynyloxy-benzenesulfonyl)-acetic acid ethyl ester (2 g, 6.73 mmol) and bis-(2-chloro-ethyl)-benzyl amine (2.3 g, 8.8 mmol). Yield 3.33 g (99%); yellow oil; MS: 455.9 (M+H)+

1-Benzyl-4-(4-but-2-ynyloxy-benzenesulfonyl)-piperdine-4-carboxylic acid was prepared starting from 1-benzyl-4-(4-but-2-ynyloxy-benzenesulfonyl)-piperdine-4-carboxylic acid ethyl ester (3 g, 6.6 mmol) dissolved in THF:methanol (3:1 150 ml) and 10 N NaOH (15 ml). The resulting reaction mixture was worked up as outlined in Example 1 (Step 7). Yield 1.65 g (59%); off white powder; mp 191° C.; MS: 428 (M+H)+

Starting from 1-benzyl-4-(4-but-2-ynyloxy-benzenesulfonyl)-piperidine-4-carboxylic acid (1.55 g, 3.63 mmol) and following the procedure as outlined in Example 1 (Step 8), 1.08 g of 1-benzyl-4-(4-but-2-ynyloxy-benzenesulfonyl)-piperidine-4-carboxylic acid hydroxyamide was isolated as a hydrochloride salt, an off white powder. Yield 62%; mp 175° C.; MS: 443 (M+H)+; 1H NMR (300 MHz, DMSO-$d_6$): δ1.85 (t, J=2.16 Hz, 3H), 2.25 (m, 2H), 2.49 (m, 4H), 2.77 (m, 2H), 4.28 (d, J=4.3 Hz, 2H), 4.89 (d, J=2.28, 2H), 7.18 (m, 2H), 7.46 (m, 5 H), 7.73 (m, 2H), 9.36 (s, 1H), 10.27 (s, 1H), 11.08 (s, 1H).

EXAMPLE 5

1-(4-Bromo-benzyl)-4-(4-pent-2-ynyloxy-benzenesulfonyl)-piperdine-4-carboxylic acid hydroxyamide (4-Pent-2-ynyloxy-phenylsulfanyl)-acetic acid ethyl ester was prepared according to the general method as outlined in Example 1 (Step 2). Starting from (4-hydroxy-phenylsulfanyl)-acetic acid ethyl ester (5 g, 30 mmol) and 2-pentynyl chloride (3.7 g, 36.6 mmol) 7.15 g of the product isolated. Yield 7.15 g (86%); brown oil; MS: 278 EI (M+H)+

(4-Pent-2-ynyloxy-benzenesulfonyl)-acetic acid ethyl ester was prepared according to the general method as outlined in Example 1 (Step 3). Starting from (4-pent-2-ynyloxy-phenylsulfanyl)-acetic acid ethyl ester (7.04 g, 25.3 mmol) and oxone (25 g) (4-Pent-2-ynyloxy-benzenesulfonyl)-acetic acid ethyl ester was isolated. Yield 8 g (99%); yellow oil; MS: 310.9 (M+H)+

1-(4-Bromo-benzyl)-4-(4-pent-2-ynyloxy-benzenesulfonyl)-piperidine-4-carboxylic acid ethyl ester was prepared according to the general method as outlined in Example 1 (Step 6). Starting from (4-pent-2-ynyloxy-benzenesulfonyl)-acetic acid ethyl ester (4 g, 12.9 mmol) and (4-bromo-benzyl)-bis-(2-chloro-ethyl)-amine (5.83 g, 16.8 mmol, 2.85 g of the product was isolated. Yield 2.85 g (31%); low melting white solid; MS: 549.9 (M+H)$^+$ 1-(4-Bromo-benzyl)-4-(4-pent-2-ynyloxy-benzenesulfonyl)-piperdine-4-carboxylic acid was prepared starting from 1-(4-bromo-benzyl)-4-(4-pent-2-ynyloxy-benzenesulfonyl)-piperdine-4-carboxylic acid ethyl ester (2.64 g 4.8 mmol) dissolved in THF:methanol (100:50 ml) and 10 N NaOH (10 ml). The resulting reaction mixture was worked up as outlined in Example 1 (Step 7). Yield 1.6 g (65%); off white solid; mp 217° C.; MS: 521.9 (M+H)$^+$ Starting from 1-(4-bromo-benzyl)-4-(4-pent-2-ynyloxy-benzenesulfonyl)-4-carboxylic acid (1.55 g, 2.98 mmol) and following the procedure as outlined in Example 1 (Step 8), 200 mg of 1-(4-bromo-benzyl)-4-(4-pent-2-ynyloxy-benzenesulfonyl)-piperdine-4-carboxylic acid hydroxyamide was isolated as a HCl salt, a yellow solid. Yield 12%; mp 62° C.; MS: 536.9 (M+H)$^+$; $^1$H NMR (300 MHz, DMSO-d$_6$): δ1.069 (t, J=7.47 Hz, 3H), 2.26 (m, 2H), 2.49 (m, 2H), 2.73 (m, 2H), 2.89 (s, 2H), 3.40 (d, 2H), 4.26 (d, 2H), 4.9 (m, 2H) 7.18 (m, 2H), 7.48 (d, J=8.4 Hz, 2H), 7.66 (m, 4H), 10.39 (s, 1H), 11.19 (s, 1H).

EXAMPLE 6

1-(4-Bromo-benzyl)-4-(4-oct-2-ynyloxy-benzenesulfonyl)-piperdine-4-carboxylic acid hydroxyamide (4-Oct-2-ynyloxy-phenylsulfanyl)-acetic acid ethyl ester was prepared according to the general method as outlined in Example 1 (Step 2). Starting from (4-hydroxy-phenyl-sulfanyl)-acetic acid ethyl ester (5 g, 30 mmol) and 1-bromo-2-octyne (6.9 g, 36.6 mmol) 8.9 g of (4-oct-2-ynyloxy-phenylsulfanyl)-acetic acid ethyl ester was isolated. Yield 8.9 g (92%); yellow oil; MS: 320 EI (M+H)$^+$ (4-Oct-2-ynyloxy-benzenesulfonyl)-acetic acid ethyl ester was prepared according to the general method as outlined in Example 1 (Step 3). Starting from (4-oct-2-ynyloxy-phenylsulfanyl)-acetic acid ethyl ester (8.8 g, 27.5 mmol) 8.45 g of (4-oct-2-ynyloxy-phenylsulfonyl)-acetic acid ethyl ester was isolated. Yield 8.45 g (87%); yellow oil; MS: 352 EI (M+H)$^+$ 1-(4-Bromo-benzyl)-4-(4-oct-2-ynyloxy-benzenesulfonyl)-piperdine-4-carboxylic acid ethyl ester was prepared according to the general method as outlined in Example 1 (Step 6). Starting from (4-oct-2-ynyloxy-benzenesulfonyl)-acetic acid ethyl ester (4 g, 11.4 mmol) and (4-bromo-benzyl)-bis-(2-chloro-ethyl)-amine (5.13 g, 14.8 mmol) 1.47 g of 1-(4-bromo-benzyl)-4-(4-oct-2-ynyloxy-benzenesulfonyl)-piperdine-4-carboxylic acid ethyl ester was isolated. Yield 1.47 g (22%); yellow solid; MS: 591.9 (M+H)$^+$ 1-(4-Bromobenzyl)-4-(4-oct-2-ynyloxy-benzenesulfonyl)-piperdine-4-carboxylic acid was prepared starting from 1-(4-bromobenzyl)-4-(4-oct-2-ynyloxy-benzenesulfonyl)-piperdine-4-carboxylic acid ethyl ester (1.36 g, 2.3 mmol) dissolved in THF:methanol (50:50 ml) and 10 N NaOH (10 ml). The resulting reaction mixture was worked up as outlined in Example 1 (Step 7). Yield 660 mg (51%); off white solid; mp 199° C.; MS: 562 (M+H)$^+$ Starting from 1-(4-bromo-benzyl)-4-(4-oct-2-ynyloxy-benzenesulfonyl)-piperdine-4-carboxylic acid (570 mg, 1.01 mmol) and following the procedure as outlined in Example 1 (Step 8), 100 mg of 1-(4-bromo-benzyl)-4-(4-oct-2-ynyloxy-benzenesulfonyl)-piperdine-4-carboxylic acid hydroxyamide was isolated as a hydrochloride salt, a white powder. Yield 17%; mp 140° C.; MS: 579 (M+H)$^+$; $^1$H NMR (300 MHz, DMSO-d$_6$): δ0.828 (t, J=7.14 Hz, 3H), 1.25 (m, 6H), 1.38 (m, 2H), 2.27 (m, 2H), 2.49 (m, 4H), 2.73 (m, 2H), 4.03 (m, 2H), 4.91 (s, 2H), 7.18 (d, J=9 Hz, 2H), 7.47 (d, J=8.1 Hz, 2H), 7.68 (m, 4H), 9.43 (s, 1H), 10.25 (s, 1H), 11.19 (s, 1H).

EXAMPLE 7

4-(4-But-2-ynyloxy-benzenesulfonyl)-1-(4-fluoro-benzyl)-piperidine-4-carboxylic acid hydroxyamide 2-[(4-Fluoro-benzyl)-(2-hydroxy-ethyl)-amino]-ethanol was prepared according to the general method as outlined in Example 1 (Step 4). Starting from diethanolamine (15.7 g, 150 mmol), and 4-fluoro-benzyl chloride (14.4 g, 100 mmol) 20 g of the product was isolated. Yield 20 g, (93%%); yellow oil; MS: 215 M+H)$^+$ (4-Flouro-benzyl)-bis-(2-chloro-ethyl)-amine was prepared according to the general method as outlined in Example 1 (Step 5). Starting from 2-[(4-fluoro-benzyl)-(2-hydroxy-ethyl)-amino]-ethanol (23.6 g, 110 mmol) 28 gms of the product was isolated. Yield 28 g, (96%); brown solid; mp 98–99° C.; MS: 251 (M+H)$^+$ 4-(4-But-2-ynyloxy-benzenesulfonyl)-1-(4-fluoro-benzyl)-piperidine-4-carboxylic acid ethyl ester was prepared according to the general method as outlined in Example 1 (Step 6). Starting from (4-but-2-ynyloxy-benzenesulfonyl)-acetic acid ethyl ester (5 g, 16.9 mmol) and (4-fluoro-benzyl)-bis-(2-chloro-ethyl)-amine (5.8 g, 20.1 mmol) 5.3 g of the product was isolated. Yield 5.3 g (67%); Brown oil; MS: 474 (M+H)$^+$ 4-(4-But-2-ynyloxy-benzenesulfonyl)-1-(4-fluoro-benzyl)-piperidine-4-carboxylic acid was prepared starting from 4-(4-but-2-ynyloxy-benzenesulfonyl)-1-(4-fluoro-benzyl)-piperidine-4-carboxylic acid ethyl ester (9.5 g, 20 mmol) dissolved in THF:methanol 3:1 (100 ml) and 10 N NaOH (20 ml). The resulting reaction mixture was worked up as outlined in Example 1 (Step 7). Yield 5.7 g (63%); white solid; mp 106-106° C.; MS: 447 (M+H)$^+$ Starting from 4-(4-but-2-ynyloxy-benzenesulfonyl)-1-(4-fluoro-benzyl)-piperidine-4-carboxylic acid (5.7 g, 13 mmol) and following the procedure as outlined in Example 1 (Step 8), 4.1 g of 4-(4-but-2-ynyloxy-benzenesulfonyl)-1-(4-fluoro-benzyl)-piperdine-4-carboxylic acid hydroxyamide was isolated as a HCl salt, a yellow solid. Yield: 64%; mp 162–4° C.; MS: 461 (M+H)$^+$; $^1$H NMR (300 MHz, CDCl$_3$): δ1.92 (s, 3H), 2.02–2.32 (m, 6H), 2.86 (m, 2H), 3.41 (d, 2H), 4.84 (d, 2H), 7.01 (d, J=8.94 Hz, 2H), 7.15 (d, J=8.88 Hz, 2H), 7.25 (d, J=9 Hz, 2H), 7.74 (d, J=9.0 Hz, 2H), 9.4–9.7 (bs, 1H).

EXAMPLE 8

4-(4-But-2-ynyloxy-benzenesulfonyl)-1-(4-cyano-benzyl)-piperidine-4-carboxylic acid hydroxyamide 4-{[Bis-(2-hydroxyethyl)-amino]-methyl}benzonitrile was prepared according to the general method as outlined in Example 1 (Step 4) starting from diethanolamine (10.2 g, 97 mmol) and α-bromo-p-tolunitrile (15.8 g, 81 mmol). Yield, (68%); white solid; mp 163° C. MS: 221.2 (M+H)$^+$ 4-{[Bis-(2-chloroethyl)-amino]-methyl}benzonitrile was prepared according to the general method as outlined in Example 1 (Step 5) starting from 4-{[bis-(2-hydroxyethyl)-amino]-methyl}benzonitrile (33.28 g, 122 mmol). Yield g, (%); brown solid; mp ° C.; MS: (M+H)$^+$ 4-(4-But-2-ynyloxy-benzenesulfonyl)-1-(4-cyano-benzyl)-piperidine-4-carboxylic acid ethyl ester was prepared according to the general method as outlined in Example 1 (Step 6). Starting from 4-(4-but-2-ynyloxy-benzenesulfonyl)-acetic acid ethyl ester (5.86 g, 19.8 mmol) and 4-cyano-benzyl-bis-(2-chloro-ethyl)-amine (5.4 g, 18 mmol) 4.7 g of the product was isolated. Yield (52%); amber oil; MS: 481.0 (M+H)$^+$ 4-(4-But-2-ynyloxy-benzenesulfonyl)-1-(4-cyano-benzyl)-piperidine-4-carboxylic acid was prepared starting from 4-(4-But-2-ynyloxy-benzenesulfonyl)-1-(4-cyano-benzyl)-piperidine-4-carboxylic acid ethyl ester (4 g, 8.3 mmol) dissolved in THF:Methanol (60:30 ml) and 10 N NaOH (10 ml). The resulting reaction mixture was worked up as outlined in Example 1 (Step 7). Yield 1.8 g (48%); off white solid; MS: 441.9 (M+H)$^+$ Starting from 4-(4-But-2-ynyloxy-benzenesulfonyl)-1-(4-cyano-benzyl)-piperidine-4-carboxylic acid (1.8 g, 4 mmol) and following the procedure as outlined in Example 1 (Step 8), 0.20 g of 4-(4-But-2-ynyloxy-benzenesulfonyl)-1-(4-cyano-benzyl)-piperidine-4-carboxylic acid hydroxamide was isolated as a hydrochloride salt, white solid. Yield 20%; mp 109.6° C.; MS: 468.0 (M+H)$^+$; $^1$H NMR (300 MHz, DMSO-d$_6$): δ1.86 (m, 3H), 2.25 (m, 4H), 2.5 (m, 2H), 2.85 (d, 2H), 4.39 (s, 2H), 4.88 (s, 2H), 7.15–7.19 (d, J=13.2, 2H), 7.67–7.70 (d, J=13.5, 2H), 7.78 (m, 2H), 7.96–7.99 (d, J=9.6, 2H), 9.42 (s, 1H), 10.14 (s, 1H), 11.20 (s, 1H)

EXAMPLE 9

4-(4-But-2-ynyloxy-benzenesulfonyl)-1-(4-methyl-benzyl)-piperidine-4-carboxylic acid hydroxamide 2-[(2-Hydroxy-ethyl)-(4-methyl-benzyl)-amino]-ethanol was prepared according to the general method as outlined in Example 1 (Step 4). Starting from diethanolamine (4.84 g, 46 mmol) and 4-methylbenzyl bromide (8.5 g, 46 mmol), 8.2 g of the product was isolated. Yield, (85%); white solid; MS: 210.1 (M+H)$^+$ 4-Methyl-benzyl-bis-(2-chloro-ethyl)-amine was prepared according to the general method as outlined in example 1 (Step 5). Starting from 2-[(2-Hydroxy-ethyl)-(4-methyl-benzyl)-amino]-ethanol (6.0 g, 20 mmol) 5.2 g of the product was isolated. Yield: (84%); yellow solid; mp 145–147° C.; MS: 245.9 (M+H)$^+$ 4-(4-But-2-ynyloxy-benzenesulfonyl)-1-(4-methyl-benzyl)-piperidine-4-carboxylic acid ethyl ester was prepared according to the general method as outlined in Example 1 (Step 6). Starting from 4-(4-but-2-ynyloxy-benzenesulfonyl)-acetic acid ethyl ester (5.75 g, 19.0 mmol) and 4-methyl-benzyl-bis-(2-chloro-ethyl)-amine (6.04, 208 mmol) 6.47 g of the product was isolate. Yield: (72%); amber oil; MS: 470 (M+H)$^+$ 4-(4-But-2-ynyloxy-benzenesulfonyl)-1-(4-methyl-benzyl)-piperidine-4-carboxylic acid was prepared starting from 4-(4-But-2-ynyloxy-benzenesulfonyl)-1-(4-methyl-benzyl)-piperidine-4-carboxylic acid ethyl ester (6.4 g, 13.6 mmol) dissolved in THF:Methanol (30:20 ml) and 10 N NaOH (15 ml). The resulting reaction mixture was worked up as outlined in Example 1 (Step 7). Yield 2.3 g (48%); off white solid; mp 213° C. MS: 441.9 (M+H)$^+$ Starting from 4-(4-But-2-ynyloxy-benzenesulfonyl)-1-(4-methyl-benzyl)-piperidine-4-carboxylic acid (2.0 g, 5.0 mmol) and following the procedure as outlined in Example 1 (Step 8), 3.6 g of 4-(4-But-2-ynyloxy-benzenesulfonyl)-1-(4-methyl-benzyl)-piperidine-4-carboxylic acid hydroxamide was isolated as a HCl salt, off-white solid. Yield 1.2 g (28%); mp 188° C.; MS: 457.0 (M+H)$^+$; $^1$H NMR (300 MHz, DMSO-d$_6$): δ1.86 (s, 3H), 2.27 (m, 2H), 2.50 (m, 4H), 2.64 (m, 2H), 4.23–4.24 (d, J=4.5, 2H), 4.89 (d, J=1.8, 2H), 7.16–7.19 (d, J=9 2H), 7.24–7.26 (d, J=7.5, 2H), 7.37–7.40 (d, J=8.1, 2H), 9.36 (s, 1H), 10.11 (s, 1H), 11.20 (s, 1H)

EXAMPLE 10

4-(4-But-2-ynyloxy-benzenesulfonyl)-1-(3,4-dichloro-benzyl)-piperidine-4-carboxylic acid hydroxamide 2-[(2-Hydroxy-ethyl)-(3,4-dichlor-benzyl)-amino]-ethanol was prepared according to the general method as outlined in Example 1 (Step 4). Starting from diethanolamine (4.84 g, 46 mmol) and 3,4-dichlorobenzyl chloride (8.97 g, 46 mmol), 9.4 g of the product was isolated. Yield, (78%); white solid; MS: 264.3 (M+H)$^+$ 3,4-Dichloro-benzyl-bis-(2-chloro-ethyl)-amine was prepared according to the general method as outlined in Example 1 (Step 5). Starting from 2-[(2-Hydroxy-ethyl)-(3,4-dichloro-benzyl)-amino]-ethanol (10.7 g, 41 mmol), 10.7 g of the product was isolated. Yield: (84%); yellow solid; mp 218–220° C.; MS: 301.8 (M+H)$^+$ 4-(4-But-2-ynyloxy-benzenesulfonyl)-1-(3,4-dichloro-benzyl)-piperidine-4-carboxylic acid ethyl ester was prepared according to the general method as outlined in Example 1 (Step 6). Starting from 4-(4-but -2-ynyloxy-benzenesulfonyl)-acetic acid ethyl ester (6.1 g, 23 mmol) and 3,4-dichloro-benzyl-bis-(2-chloro-ethyl)-amine (8.6 g, 25 mmol), 4.9 g of the product was isolated. Yield: (41%); amber oil; MS: 523.8 (M+H)$^+$ 4-(4-But-2-ynyloxy-benzenesulfonyl)-1-(3,4-dichloro-benzyl)-piperidine-4-carboxylic acid was prepared starting from 4-(4-But-2-ynyloxy-benzenesulfonyl)-1-(3,4-dichloro-benzyl)-piperidine-4-carboxylic acid ethyl ester ester (8.6 g, 16.4 mmol) dissolved in THF:Methanol (40:30 ml) and 10 N NaOH (15 ml). The resulting reaction mixture was worked up as outlined in Example 1 (Step 7). Yield 2.1 g (38%); off white solid; mp 232° C. MS: 495.9 (M+H)$^+$ Starting from 4-(4-But-2-ynyloxy-benzenesulfonyl)-1-(3,4-dichloro-benzyl)-piperidine-4-carboxylic acid (2.06 g, 4.0 mmol) and following the procedure as outlined in Example 1 (Step 8), 1.2 g of 4-(4-But-2-ynyloxy-benzenesulfonyl)-1-(3,4-dichloro-benzyl)-piperidine-4-carboxylic acid hydroxamide was isolated as a HCl salt, off-white solid. Yield 1.2 g (56%); mp 213° C.; MS: 510.9 (M+H)$^+$; $^1$H NMR (300 MHz, DMSO-d$_6$): δ1.86 (s, 3H), 2.30 (m, 2H), 2.50 (m, 4H), 2.80 (m, 2H), 4.40 (s, 2H), 4.90 (s, 2H), 7.16–7.19 (d, J=9 2H), 7.51–7.54 (d, J=8.4, 2H), 7.66–7.69 (d, J=9.0, 2H), 7.75–7.86 (d, J=11.7, 2H), 7.88 (s, 1H), 9.38 (s, 1H), 10.44 (s, 1H), 11.19 (s, 1H).

EXAMPLE 11

1-(4-Bromo-benzyl)-4-(4-prop-2-ynyloxy-benzenesulfonyl)-piperdine-4-carboxylic acid hydroxyamide Step 1

(4-Prop-2-ynyloxy-phenylsulfanyl)-acetic acid ethyl ester was prepared according to the general method as outlined in Example 1 (Step 2). Starting from (4-hydroxy-phenylsulfanyl)-acetic acid ethyl ester (example 1, 1$^{st}$ paragraph) (2.12 g, 10 mmol) and propargyl bromide (1.8 g, 15 mol) 2.4 g of the product was isolated. Yield: (96%); amber oil; MS: 251(M+H)$^+$ Step 2

(4-Prop-2-ynyloxy-benzenesulfonyl)-acetic acid ethyl ester was prepared according to the general method as outlined in Example 1 (Step 3). Starting from (4-prop-2-ynyloxy-phenyl sulfanyl)-acetic acid ethyl ester (2.5 g, 10 mmol) 2.8 g of (4-Prop-2-ynyloxy-benzenesulfonyl)-acetic acid ethyl ester was isolated. Yield (99%); brown oil; MS: 283 (M+H)$^+$ Step 3

1-(4-Bromo-benzyl)-4-(4-prop-2-ynyloxy-benzenesulfonyl)-piperdine-4-carboxylic acid ethyl ester was prepared according to the general method as outlined in Example 1 (Step 6). Starting from (4-prop-2-ynyloxy-benzenesulfonyl)-acetic acid ethyl ester (21.62 g, 76.7 mmol) and (4-bromo-benzyl)-bis-(2-chloro-ethyl)-amine (31.9 g, 92 mmol), 23 g of the ester derivative was isolated. Yiel: (58%); yellow oil; MS: 521.9 (M+H)$^+$.

Step 4

1-(4-Bromo-benzyl)-4-(4-prop-2-ynyloxy-benzenesulfonyl)-piperdine-4-carboxylic acid was prepared starting from 1-(4-bromo-benzyl)-4-(4-prop-2-ynyloxy-benzene-sulfonyl)-piperidine-4-carboxylic acid ethyl ester (5 g, 9.59 mmol) dissolved in THF:methanol (150:50 ml) and 10 N NaOH (15 ml). The resulting reaction mixture was worked up as outlined in Example 1 (Step 7). Yield 3.4 g (72%); brown low melting solid; MS: 491.9 (M–H)$^-$ Step 5

Starting from 1-(4-Bromo-benzyl)-4-(4-prop-2-ynyloxy-benzenesulfonyl)-piperdine-4-carboxylic acid (3 g, 6.1 mmol) and following the procedure as outlined in Example 1 (Step 8), 580 mg of 1-(4-bromo-benzyl)-4-(4-prop-2-ynyloxy-benzene-sulfonyl)-piperdine-4-carboxylic acid hydroxyamide was isolated as an HCl salt, off white powder. Yield 18%; mp 155° C.; MS: 508.8 (M+H)$^+$; $^1$H NMR (300 MHz, DMSO-d$_6$): δ2.22 (m, 2H), 2.50 (m, 2H), 2.79 (m, 2H), 3.45 (m, 2H), 4.27 (m, 2H), 4.96 (d, J=2.3 Hz, 2H), 7.2 (d, J=9 Hz, 2H), 7.48 (m, 2H), 7.68 (m, 4H), 9.37 (s, 1H), 10.36 (s, 1H), 11.19 (s, 1H).

EXAMPLE 12

1-(4-Bromo-benzyl)-4-[4-(4-piperdin-4-yl-but-2-ynyloxy)-benzenesulfonyl]-piperdine-4-carboxylic acid hydroxyamide To a stirred solution of piperidine (1.63 g, 19.2 mmol) diluted in dioxane (100 mL) acetic acid (5 mL) was added. The reaction fumed and stirred for 5 minutes. 1-(4-bromo-benzyl)-4-(4-prop-2-ynyloxy-benzenesulfonyl)-piperdine-4-carboxylic acid ethyl ester (5.0 g, 9.6 mmol), paraformaldehyde (0.29 g, 9.6 mmol) and the copper(I)chloride (0.35 g) was added to the piperidine solution. The reaction turned green and was heated at reflux for 1 hour turned brown. It was then concentrated and diluted in ice water then brought to pH 8 with NH$_4$OH and extracted in CHCl$_3$. The organic layer was washed 4 times with water then dried over Na$_2$SO$_4$ then concentrated. The product was purified by silica gel column chromatography by eluting it with 5% methanol:chloroform solution.

Yield 5.15 g (87%); brown oil; MS: 309.9 (M+2H)$^{2+}$, 618.8 (M+H)$^+$ 1-(4-Bromo-benzyl)-4-[4-(4-piperidin-1-yl-but-2-ynyloxy)-benzenesulfonyl]-piperdine-4-carboxylic acid was prepared starting from 1-(4-bromo-benzyl)-4-[4-(4-piperidin-1-yl-but-2-ynyloxy)-benzenesulfonyl]-piperidine-4-carboxylic acid ethyl ester (4.64 g, 7.5 mmol) dissolved in THF:methanol (50:150 ml) and 10 N NaOH (20 ml). The resulting reaction mixture was worked up as outlined in Example 1 (Step 7). Yield 3.35 g (76%); off white solid; mp 180° C.; MS: 295.9 (M+2H)$^{2+}$ 590.9 (M+H)$^+$ Starting from 1-(4-bromo-benzyl)-4-[4-(4-piperidin-1-yl-but-2-ynyloxy)-benzene-sulfonyl]-piperidine-4-carboxylic acid (1.9 g, 3.2 mmol) and following the procedure as outlined in Example 1 (Step 8), 810 mg of 1-(4-bromo-benzyl)-4-[4-(4-piperidin-1-yl-but-2-ynyloxy)-benzenesulfonyl]-piperidine-4-carboxylic acid hydroxyamide was isolated as a hydrochloride salt, a pale yellow solid. Yield 40%; mp 209° C.; MS: 303.4 (M+2H)$^{2+}$ 605.9 (M+H)$^+$; $^1$H NMR (300 MHz, DMSO-d$_6$): δ1.70 (m, 2H), 2.29 (m, 2H), 2.76 (m, 4H), 3.40 (m, 10H), 4.14 (s, 2H), 4.26 (2H) 7.24 (d, J=9 Hz, 2H), 7.51 (d, J=8.4 Hz, 2H), 7.67 (m, 4H), 9.39 (s, 1H), 10.45 (s, 1H).

EXAMPLE 13

1-(4-Bromo-benzyl)-4-[4-(4-morpholin-4-yl-but-2-ynyloxy)-benzenesulfonyl]-piperdine-4-carboxylic acid hydroxyamide To a stirred solution of morpholine (1.68 g, 19.2 mmol) diluted in dioxane (100 mL) acetic acid (5 mL) was added. The reaction fumed and stirred for 5 minutes. 1-(4-bromo-benzyl)-4-(4-prop-2-ynyloxy-benzenesulfonyl)-piperidine-4-carboxylic acid ethyl ester (5.0 g, 9.6 mmol), paraformaldehyde (0.29 g, 9.6 mmol) and the copper(I)chloride (0.35 g) was added to the piperidine solution. The reaction turned green and was heated at reflux for 1 hour turned brown. It was then concentrated and diluted in ice water then brought to pH 8 with NH$_4$OH and extracted in CHCl$_3$. The organic layer was washed 4 times with water then dried over Na$_2$SO$_4$ then concentrated. The product, 1-(4-Bromo-benzyl)-4-[4-(4-morpholin-4-yl-but-2-ynyloxy)-benzenesulfonyl]-piperidine-4-carboxylic acid ethyl ester was purified by silica gel column chromatography by eluting it with 5% methanol:chloroform solution. Yield 3.0 g (50%); colorless solid; mp 110° C.; MS: 311 (M+2H)$^{2+}$, 621 (M+H)$^+$ 1-(4-Bromo-benzyl)-4-[4-(4-morpholin-4-yl-but-2-ynyloxy)-benzenesulfonyl]-piperidine-4-carboxylic acid was prepared starting from 1-(4-bromo-benzyl)-4-[4-(4-morpholin-4-yl-but-2-ynyloxy)-benzenesulfonyl]-piperidine-4-carboxylic acid ethyl ester (2.87 g, 4.6 mmol) dissolved in THF:methanol (3:1, 150 ml) and 10 N NaOH (10 ml). The resulting reaction mixture was worked up as outlined in Example 1 (Step 7). Yield 2.26 g (83%); white powder; mp 198° C.; MS: 593.1 (M+H)$^+$ Starting from 1-(4-bromo-benzyl)-4-[4-(4-morpholin-4-yl-but-2-ynyloxy)-benzenesulfonyl]-piperidine-4-carboxylic acid (2.1 g, 3.55 mmol) and following the procedure as outlined in example 1, 1.8 g of 1-(4-bromo-benzyl)-4-[4-(4-morpholin-4-yl-but-2-ynyloxy)-benzenesulfonyl]-piperidine-4-carboxylic acid hydroxyamide was isolated as a hydrochloride salt, a white solid. Yield 80%; mp 94° C.; MS: 304.4 (M+2H)$^{2+}$ 607.9 (M+H)$^+$; $^1$H NMR (300 MHz, DMSO-d$_6$): δ2.38 (m, 2H), 2.46 (m, 2H), 2.75 (m, 2H), 3.35 (m, 2H), 3.87, (m, 8H), 4.21 (s, 2H), 4.26 (s, 2H), 5.10 (s, 2H), 7.24 (d, J=9 Hz, 2H), 7.51 (d, J=8.4 Hz, 2H), 7.67 (m, 4H), 9.42 (s, 1H), 10.69 (s, 1H), 11.13 (s, 1H)

Examples of compound where A=S or S=O.

EXAMPLE 14

4-(4-But-2-ynyloxy-phenylsulfanyl)-4-hydroxycarbamoyl-piperidine-1-carboxylic acid tert-butyl ester To a solution of triphenylphosphine (24.7 g, 94.2 mmol) and dimethylformamide (0.6 mL) in dichloromethane (25 mL) was added a solution of 4-but-2-ynyloxy-phenylsulfonyl chloride (7.69 g, 31.4 mmol) in dichloromethane dropwise over 30 min. After an additional 2 h, 1N aqueous hydrochloric acid (20 mL) and water was added. The organic layer was separated and concentrated in vacuo. Aqueous sodium hydroxide (1N, 50 mL) was added and the solid removed by filtration. The aqueous phase was washed with diethyl ether (3×), treated with 1N aqueous hydrochloric acid (50 mL) and extracted with ether (3×). the combined organic extracts were dried over anhydrous magnesium sulfate and concentrated to give the thiol as an oil (3.77 g). This material was dissolved in dimethylsulfoxide (40 mL) and concentrated hydrochloric acid was added (2 mL). After 18 h, diethyl ether was added and the organic phased was washed with water (5×) and dried over anhydrous magnesium sulfate. Concentration in vacuo gave a yellow solid which was filtered through silica gel with hexane:ethyl acetate to give bis (4-but-2-ynyloxy phenyl) disulfide as a yellow solid (3.0 g, 80%). $^1$HNMR (CDCl3: 300 MHz): 1.86 (s, —CH3, 3H), 4.63 (s, —CH2, 2H), 6.90 (d, ArH, 2H, J=9 Hz), 7.40 (d, ArH, 2H, J=9 Hz).

To a solution of N-BOC-isonipecotic acid (0.62 g, 2.7 mmol) in tetrahydrofuran (20 mL) at −78° C. was added tert-butyllithium (3.4 mL, 1.7M in hexane, 5.7 mmol). After 10 min at −78° C. the yellow solution was warmed to 0° C. in an ice bath. After 30 min the colorless solution was cooled to −78° C. whereupon bis (4-but-2-ynyloxy phenyl) disulfide(1.0 g, 2.8 mmol) was added as a solution in tetrahydrofuran (6 mL). The reaction mixture was allowed to warm to 25° C. After 1.5 h ethyl acetate was added followed by 6 mL of 1N aqueous hydrochloric acid in 20 mL of water. The organic layer was washed with water and brine, dried over anhydrous magnesium sulfate and concentrated in vacuo. Chromatography on silica gel (methanol/methylene chloride) gave the product (0.55 g). $^1$H NMR (DMSO-d6): 1.38 (s, OtBu, 9H), 1.5–1.6 (m, CH$\underline{H}$, 2H), 1.84 (s, CH3, 3H), 1.89–1.99 (m, CH$\underline{H}$, 2H), 2.95–3.05 (m, CH$\underline{H}$, 2H), 3.6–3.7 (m, CH$\underline{H}$, 2H), 4.8 (s, CH2, 2H), 6.95 (d, ArH, 2H, J=9 Hz), 7.38 (d, ArH, 2H, J=9 Hz).

Dimethylformamide (0.163 mL) was added to a solution of oxalyl chloride (1.06 mL of a 2.0M solution in dichloromethane) in dichloromethane (2 mL) at 0° C. After 15 min a solution of the acid in dimethylformamide (5 mL) was added and the reaction mixture was allowed to warm to room temperature. After 1 h the reaction mixture was added to a mixture of hydroxylamine hydrochloride (0.737 g), triethylamine (2.22 mL), water (5.7 mL) and tetrahydrofuran (22.8 mL) that had been stirring at 0° C. for 15 min. The reaction was held at 0° C. for 18 h then diluted with dichloromethane and washed with saturated aqueous sodium bicarbonate (3×), then dried over potassium carbonate and concentrated in vacuo to give 480 mg of 4-(4-but-2-ynyloxy-phenylsulfanyl)-4-hydroxycarbamoyl-piperidine-1-carboxylic acid tert-butyl ester. $^1$H NMR (DMSO-d6): 1.37 (s, OtBu, 9H), 1.5–1.6 (m, CH$\underline{H}$, 2H), 1.84 (s, CH$_3$, 3H), 1.9–2.0 (m, CH$\underline{H}$, 2H), 3.05–3.15 (m, CH$\underline{H}$, 2H), 3.5–3.6 (m, CH$\underline{H}$, 2H), 4.8 (s, CH$\underline{H}$, 2H), 6.9 (d, ArH, 2H), 7.4 (d, ArH, 2H), 8.8 (s, NHOH, 1H), 10.7 (d, NHOH, 1H).

EXAMPLE 15

4-(4-But-2-ynyloxy-phenylsulfanyl)-piperidine-4-carboxylic acid hydroxyamide 4-(4-But-2-ynyloxy-phenylsulfanyl)-4-hydroxycarbamoyl-piperidine-1-carboxylic acid tert-butyl ester, prepared by the method outlined in Example 14 (Step 3) (0.175 g, 0.4 mmol), was treated with 4N hydrochloric acid in dioxane (5 mL) at 25 ° C. for 1 h 15 min. The reaction mixture was concentrated in vacuo, diethyl ether was added and the resulting precipitate isolated by filtration to give 4-(4-but-2-ynyloxy-phenylsulfanyl)-piperidine-4-carboxylic acid hydroxyamide as a white solid (0.12 g). Electrospray Mass Spectroscopy: ((M+H)$^+$=321)

EXAMPLE 16

1-(4-Bromo-benzyl)-4-(4-but-2-ynyloxy-phenylsulfanyl)-piperidine-4-carboxylic acid hydroxyamide 4-(4-But-2-ynyloxy-phenylsulfanyl)-piperidine-4-carboxylic acid hydroxy-amide (prepared by the procedure outlined in example 15) (0.15 g, 0.5 mmol) in methanol (5 mL) and dimethylformamide (2.5 mL) was treated with triethylamine (0.15 mL, 1.1 mmol) followed by 4-bromobenzylbromide (0.13 g, 0.53 mmol). After 6 h the solution was diluted with ethyl acetate, acidified to pH=6 with 1N aqueous hydrochloric acid, washed sequentially with water, aqueous sodium bicarbonate and brine and dried over anhydrous sodium sulfate. Concentration in vacuo gave 1-(4-bromo-benzyl)-4-(4-but-2-ynyloxy-phenylsulfanyl)-piperidine-4-carboxylic acid hydroxyamide. $^1$HNMR (DMSO-d6): 1.5–1.6 (m, CH$\underline{H}$, 2H), 1.8 (s, CH3, 3H), 1.9–2.2 (m, CH$\underline{H}$, 4H), 2.5–2.6 (m, CH$\underline{H}$, 2H), 3.4 (s, CH2Ar, 2H), 4.75 (s, CH2, 2H), 6.9 (d, ArH, 2H), 7.2 (d, ArH, 2H), 7.3 (d, ArH, 2H), 7.5 (d, ArH, 2H), 8.8 (s, NHOH, 1H), 10.6 (d, NHOH, 1H). Electrospray Mass Spectroscopy: ((M+H)$^+$=489/491)

Examples of compounds, where n=1 and A=S, S=O or SO$_2$

EXAMPLE 17

4-(4-But-2-ynyloxy-phenylsulfanylmethyl)-tetrahydro-pyran-4-carboxylic acid hydroxyamide 4-But-2-ynyloxy-benzenesulfonic acid sodium salt To a solution of 52.35 g (0.225 mol) of 4-hydroxybenzenesulfonate sodium alt in 1 L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 56.0 g (100%) of the butynyl ether as a white solid.

4-But-2-ynyloxy-benzenesulfonyl chloride

To a 0° solution of 43.8 mL (0.087 mol) of oxalyl chloride in 29 mL of dichloro-methane was dropwise added 6.77 mL (0.087 mol) of DMF followed by 7.24 g (0.029 mol) of 4-but-2-ynyloxy-benzenesulfonic acid sodium salt. The reaction mixture was stirred for 10 minutes at 0° then let warm to room temperature and stirred for 2 days. The reaction was then poured into ice and extracted with 150 mL of hexanes. The organics were washed with water and brine, dried over Na$_2$SO$_4$, filtered and concentrated in vacuo to provide 6.23 g (88%) of the sulfonyl chloride as a yellow solid; m.p. 63–65° C. EI Mass Spec: 243.9 (M$^+$).

But-2-ynyloxy-benzene

To a solution of 6.14 g (23.40 mmol) of triphenylphosphine dissolved in 100 mL of benzene and 50 mL of THF was added 1.75 mL (23.40 mmol) of 2-butyn-1-ol. After five minutes 2.00 g (21.28 mmol) of the phenol, dissolved in 10 mL of THF, was added to the reaction followed by 3.69 mL (23.40 mmol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 2.18 g (70%) of the desired propargylic ether as a clear liquid. EI Mass Spec: 146.0 M$^+$ 4-But-2-ynyloxy-benzenesulfonyl chloride To a solution of 0.146 g (1.0 mmol) of the but-2-ynyloxy-benzene in 0.3 mL of dichloromethane in an acetone/ice bath under $N_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 g (53%) of the desired product as a light brown solid.

4-But-2-ynyloxy-benzenethiol

To a solution of 11.8 g (0.045 mol) of triphenylphosphine dissolved in 10 mL of dichloromethane and 0.3 mL of DMF was added 3.67 g (0.015 mol) of the 4-but-2-ynyloxy-benzenesulfonyl chlorid, dissolved in 15 mL of dichloromethane and the resulting mixture was stirred for 2 h at room temperature. After the addition of 5 mL of 1N HCl solution the reaction was stirred for 0.5 h followed by the addition of 15 mL of brine. The organics were separated and concentrated in vacuo and the residue was diluted with ether and 2.5N sodium hydroxide solution. The resulting precipitate was filtered off and the aqueous layer was acidified to pH2 and extracted with ether. The combined organics were washed with brine, dried over $Na_2SO_4$, filtered through Magnesol® and concentrated in vacuo. The residue was chromatographed on silica gel eluting with hexanes/ether (4:1) to provide 1.13 g (42%) of the thiol as a yellow oil. CI Mass Spec: 179 (M+H).

4-(4-But-2-ynyloxy-phenylsulfanylmethyl)-
tetrahydro-pyran-4-carboxylic acid

To a solution of 0.112 g (2.81 mmol) of 60% sodium hydride in 2 mL of THF, cooled to 0° C., was added a solution of 0.500 g (2.81 mmol) of 4-but-2-ynyloxy-benzenethiol, dissolved in 3 mL of THF. The resulting mixture was stirred for 0.5 h at room temperature, then cooled to 5° C., followed by the addition of 0.518 g (3.65 on mol) of neat 2,7-dioxaspiro[3,5]nonane-1-one while keeping the reaction temperature below 10° C. The reaction was allowed to warm to room temperature and stirred for an additional 0.5 h and then quenched with 3 mL of 3N HCl solution and 3 mL of water. The resulting mixture was extracted with dichloromethane and the combined organics were washed with water and brine, dried over $Na_2SO_4$, filtered through a plug of silica gel and concentrated in vacuo. The residue was triturated with hexanes and acetonitrile and filtered to give 0.72 g of the carboxylic acid as a semi-solid. Electrospray Mass Spec: 319 (M–H)$^-$ 4-(4-But-2-ynyloxy-phenylsulfanylmethyl)-
tetrahydro-pyran-4-carboxylic acid hydroxyamide To a 0° C. solution of 0.74 g (2.31 mmol) of the product of 4-(4-but-2-ynyloxy-phenylsulfanylmethyl)-tetrahydro-pyran-4-carboxylic acid, dissolved in 7 mL of dichloromethane and 0.175 mL of DMF was added 1.27 mL (2.54 mmol) of a 2M solution of oxalyl chloride. The reaction was warmed to room temperature and stirred for 2 h and then recooled to 0° C. A mixture of 0.875 mL (14.2 mmol) of a 50% hydroxylamine solution, 5.0 mL of THF and 2.0 mL of t-butanol were then added to the reaction. The reaction was stirred at room temperature for 1 h and then concentrated in vacuo. The residue was extracted with dichloromethane and the combined organics were washed with water and brine, dried over $Na_2SO_4$, filtered and concentrated in vacuo. The residue was chromatographed on silica gel eluting with dichloromethane/methanol (92:8) to provide 0.212 g of the sulfide-hydroxamic acid as a white solid; m.p. 135–137° C. Electrospray Mass Spec: 336 (M+H)$^+$

EXAMPLE 18

4-(4-But-2-ynyloxy-benzenesulfonylmethyl)-
tetrahydro-pyran-4-carboxylic acid hydroxyamide To a 0° C. solution of 0.186 g (0.56 mmol) of the product of 4-(4-but-2-ynyloxy-phenylsulfanylmethyl)-tetrahydro-pyran-4-carboxylic acid hydroxyamide, dissolved in 1.2 mL of THF and 4.8 mL of methanol was dropwise added a solution of 0.619 g (1.008 mmol) of Oxone® in 3 mL of water, while keeping the temperature below 20° C. After the addition was complete the reaction was stirred at room temperature for 3 h. The reaction mixture was then poured into a cooled solution of 2.5 mL of toluene and 5 mL of ethyl acetate and the precipitate was filtered off. The filtrate was extracted with ethyl acetate/toluene and the combined organic layers were washed with water, dried over Na2SO4 and concentrated in vacuo. The residue was triturated with ethyl acetate/toluene (5:2), filtered and dried in vacuo to provide 0.12 g (55%) of the sulfone-hydroxamic acid as a white solid; m.p. 184–185° C. Electrospray Mass Spec: 368 (M+H)$^+$

EXAMPLE 19

4-(4-But-2-ynyloxy-benzenesulfinylmethyl)-
tetrahydro-pyran-4-carboxylic acid hydroxyamide To a 0° C. solution of 0.288 g (0.80 mmol) of the product of 4-(4-but-2-ynyloxy-benzenesulfanylmethyl)-tetrahydro-pyran-4-carboxylic acid hydroxyamide dissolved in 20 mL of methanol was added 7.0 mL of 30% hydrogen peroxide solution. The reaction was allowed to warm to room temperature and stirred for 24 h. The reaction mixture was then recooled to 0° C., quenched with saturated $Na_2SO_3$ and concentrated in vacuo. The residue was diluted with water and dichloromethane. The organics were washed with water and brine, dried over $Na_2SO_4$, filtered and concentrated in vacuo. The residue was chromatographed on silica gel eluting with dichloromethane/methanol (95:5) to provide 0.050 g of the sulfoxide as a white solid. Electrospray Mass Spec: 351.9 (M+H)$^+$

EXAMPLE 20

4-{[4-(2-butynyloxy)phenyl]sulfonyl}-N-
hydroxytetrahydro-2H-pyran-4-carboxamide Step 1

Ethyl 4-{[4-(2-butynyloxy)phenyl]sulfonyl}tetrahydro-2H-pyran-4-carboxylate (4-but-2-ynyloxy-benzenesulfonyl)-acetic acid ethyl ester (10 g, 33.8 mmol) was added to a stirring solution of potassium carbonate (12 g), 18-crown-6 (0.5 g), 2-chloroethyl ether (4.75 ml, 40.5 mmol), and tetrabutyl ammonium bromide (0.5 g) in methyl ethyl ketone (200 ml). The mixture was heated at reflux overnight before the salts were filtered off and the filtrate was concentrated. The residue was dissolved in chloroform and washed with water. The organic layer was dried over $Na_2SO_4$, filtered and concentrated. The compound was isolated using silica-gel column chromatography by eluting it with 20% ethyl acetate:hexane solution. Ethyl 4-{[4-(2-butynyloxy)phenyl]sulfonyl}tetrahydro-2H-pyran-4-carboxylate was isolated as a yellow oil (10.06 g). Yield 80%; MS: 367.2 (M+H)$^+$ 4-{[4-(2-butynyloxy)phenyl]sulfonyl}tetrahydro-2H-pyran-4-carboxylic acid was prepared according to the general method as outlined in example 1 (step7), starting from ethyl 4-{[4-(2-butynyloxy)phenyl]sulfonyl}tetrahydro-2H-pyran-4-carboxylate (10 g, 27.3 mmol); 2.7 g white solid. mp: 197° C.; Yield 30%; MS: 337.2 (M−H)$^-$ Starting from a crude mixture of 4-{[4-(2-butynyloxy)phenyl]sulfonyl}tetrahydro-2H-pyran-4-carboxylic acid (2.59 g, 7.66 mmol), and following the procedure as outlined in Example 1 (step 8), 1.51 g of 4-{[4-(2-butynyloxy)phenyl]sulfonyl}-N-hydroxytetrahydro-2H-pyran-4-carboxamide was isolated as off white crystals. Mp: 210° C.; Yield: 58%; MS: 354.2 (M+H)$^+$; $^1$H NMR (300 MHz, DMSO-d$_6$): δ1.85 (t, J=2.28 Hz, 3H), 1.92 (m, 2H), 2.20 (d, J=13.1 Hz, 2H), 3.15 (t, J=11.52, 2H), 3.86 (d of d, 2H), 4.88 (d, J=2.34Hz, 2H), 7.16 (d, J=8.7 Hz, 2H), 7.66 (d, J=8.91 Hz, 2H), 9.16 (s, 1H), 11 (s, 1H).

EXAMPLE 21

1-benzyl-4-{[3-(2-butynyloxy)phenyl]sulfonyl}-N-hydroxy-4-piperdine carboxamide

Ethyl [(3-hydroxyphenyl) sulfanyl]acetate was prepared according to the general method as outlined in example 1 (step 1), starting from ethyl bromoacetate (7.95 g, 47.6 mmol) and 3-hydroxythiophenol (7.95 g, 47.6 mmol); 4.21 g yellow oil. Yield 41%; MS: 211.2 (M−H)$^-$ Ethyl{[3-(2-butynyloxy)phenyl]sulfanyl}acetate was prepared according to the general method as outlined in example 1 (step 2), starting from ethyl [(3-hydroxyphenyl) sulfanyl]acetate (3.87 g, 18.3 mmol) and 4-bromo-2-butyne (2.66 g, 20 mmol); 5.16 g yellow oil. Yield 100%; MS(EI): 264.1 (M+H)$^+$ Ethyl{[3-(2-butynyloxy)phenyl]sulfonyl}acetate was prepared according to the general method as outlined in example 1 (step 3), starting from ethyl{[3-(2-butynyloxy)phenyl]sulfanyl}acetate (5 g, 18.9 mmol) and oxone (23.3 g, 37.9 mmol); 6.19 g yellow oil. Yield 100%; MS(EI): 296.1 (M+H)$^+$ Ethyl 1-benzyl-4-{[3-(2-butynyloxy)phenyl]sulfonyl}-4-piperdine carboxylate was prepared according to the general method as outlined in example 1 (step 6), starting from ethyl{[3-(2-butynyloxy)phenyl]sulfonyl}acetate (3 g, 10.1 mmol) and benzyl-bis-(2-chloro-ethyl) amine hydrochloride (2.88 g, 10.7 mmol); 2.91 g yellow oil. Yield 63%; MS: 456.3 (M+H)$^+$ 1-benzyl-4-{[3-(2-butynyloxy)phenyl]sulfonyl}-4-piperdine carboxylic acid was prepared according to the general method as outlined in example 1 (step 7), starting from ethyl 1-benzyl-4-{[3-(2-butynyloxy)phenyl]sulfonyl}-4-piperdine carboxylate (2.9 g, 6.37 mmol); 1.10 g off white powder. mp: 171° C.; Yield 40%; MS: 428.4 (M+H)$^+$ Starting from 1-benzyl-4-{[3-(2-butynyloxy)phenyl] sulfonyl}-4-piperdine carboxylic acid (1 g, 2.34 mmol), and following the procedure as outlined in Example 1 (step 8), 460 mg of 1-benzyl-4-{[3-(2-butynyloxy)phenyl]sulfonyl}-N-hydroxy-4-piperdine carboxamide was isolated as an off white solid. mp: 91.4° C.; Yield: 41%; MS: 443.4 (M+H)$^+$; $^1$H NMR (300 MHz, DMSO-d$_6$): δ1.83 (t, 3H), 2.23–2.27 (m, 2H), 2.73–2.89 (m, 2H), 3.29 (m, 2H), 3.68 (q, 2H), 4.31 (m, 1H), 4.39 (d, J=5 Hz, 1H), 4.85 (d, J=2.25, 2H), 7.25–7.61 (m, 9H), 9.1 (s, 1H), 11.2 (s, 1H).

EXAMPLE 22

4-{[4-(2-butynyloxy)phenyl]sulfonyl}-N-hydroxy-1-isopropyl-4-piperidine carboxamide Ethyl 4-{[4-(2-butynyloxy)phenyl]sulfonyl}-1-isopropyl-4-piperidine carboxylate was prepared according to the general method as outlined in example 1 (step 6), starting from (4-but-2-ynyloxy-benzenesulfonyl)-acetic acid ethyl ester (6 g, 20.3 mmol) and isopropyl [bis(2-chloroethyl)] amine hydrochloride (4.88 g, 22.3 mmol); 5.28 g brown oil. Yield 64%; MS: 408.2 (M+H)$^+$ 4-{[4-(2-butynyloxy)phenyl]sulfonyl}-1-isopropyl-4-piperidine carboxylic acid was prepared according to the general method as outlined in example 1 (step 7), starting from ethyl 4-{[4-(2-butynyloxy)phenyl]sulfonyl}-1-isopropyl-4-piperidine carboxylate (5.25 g, 13 mmol); 2.06 g yellow solid. mp: 233° C.; Yield 42%; MS: 380.1 (M+H)$^+$ Starting from 4-{[4-(2-butynyloxy)phenyl]sulfonyl}-1-isopropyl-4-piperidine carboxylic acid (1.9 g, 5 mmol), and following the procedure as outlined in Example 1 (step 8), 107 mg of 4-{[4-(2-butynyloxy)phenyl]sulfonyl}-N-hydroxy-1-isopropyl-4-piperidine carboxamide was isolated as an brown solid. mp: 105° C.; Yield: 5%; MS: 395.2 (M+H)$^+$; $^1$H NMR (300 MHz, DMSO-d$_6$): δ1.2 (m, 6H), 1.85 (t, 3H), 2.27 (m, 2H), 2.73 (m, 2H), 3.06 (m, 2H), 3.52 (m, 2H), 3.57 (m, 1H), 4.89 (m, 2H), 7.19 (m, 2H), 7.71 (m, 2H), 9.3 (s, 1H), 11.4 (s, 1H).

EXAMPLE 23

4-{[4-(2-butynyloxy)phenyl]sulfonyl}-N-hydroxy-1-(3-pyridinylmethyl)-4-piperidine carboxamide Ethyl 4-{[4-(2-butynyloxy)phenyl]sulfonyl}-1-(3-pyridinylmethyl)-4-piperidine carboxylate was prepared according to the general method as outlined in example 1 (step 6), starting from (4-but-2-ynyloxy-benzenesulfonyl)-acetic acid ethyl ester (4 g, 16.9 mmol) and 3-pyridyl methyl [bis(2-chloroethyl)]amine hydrochloride (4.18 g, 18.6 mmol); 370 mg brown oil. Yield 5%; MS: 457.4 (M+H)$^+$ 4-{[4-(2-butynyloxy)phenyl]sulfonyl}-1-(3-pyridinyl methyl)-4-piperidine carboxylic acid was prepared according to the general method as outlined in example 1 (step 6), starting from ethyl 4-{[4-(2-butynyloxy)phenyl]sulfonyl}-1-(3-pyridinylmethyl)-4-piperidine carboxylate (320 mg, 0.7 mmol); 150 mg yellow solid. Yield 50%; MS: 429.2 (M+H)$^+$ Starting from 4-{[4-(2-butynyloxy)phenyl]sulfonyl)-1-(3-pyridinyl methyl)4-piperidine carboxylic acid (860 mg, 2 mmol), and following the procedure as outlined in Example 1 (step 8), 800 mg of 4-{[4-(2-butynyloxy)phenyl] sulfonyl}-N-hydroxy-1-(3-pyridinylmethyl)-4-piperidine carboxamide was isolated as a white solid. mp: 115° C.; Yield: 84%; MS: 444.1 (M+H)$^+$; $^1$H NMR (300 MHz, DMSO-d$_6$): δ1.86 (t, J=1.98 Hz, 3H), 2.32 (m, 2H), 2.46 (s, 2H), 2.84 (m, 2H), 3.46 (d, J=12 Hz, 2H), 4.45 (s, 2H), 4.89 (d, 2.1 Hz, 2H), 7.17 (d, J=8.9 Hz, 2H), 7.68 (d, J=8.85 Hz, 2H), 7.9 (t, J=5.6 Hz, 1H), 8.0 (s, 1H), 8.51 (d, J=7.9 Hz, 1H), 8.87 (d, J=4.6 Hz, 1H), 8.99 (s, 1H), 11.4 (s, 1H).

EXAMPLE 24

3-{[4-(2-Butynyloxy)phenyl]sulfonyl}-1-ethyl-N-hydroxy-3-piperidinecarboxamide Step 1

Piperidine-1,3-dicarboxylic acid 1-tert-butyl 3-ethyl ester

To a stirred solution of ethyl nipecotate (5.1 g, 33 mmol) in $CH_2Cl_2$ (75 ml) and triethylamine (3.7 g, 36 mmol) was added portionwise di-t-butyldicarbonate (7.1 g, 33 mmol). The reaction mixture was stirred at room temperature for 18 h, quenched with ice water and extracted with chloroform. The organic layer was dried over sodium sulfate, filtered, concentrated and chromatographed on a silica-gel column with 20:80 ethyl acetate:hexane. Piperidine 1,3dicarboxylic acid 1-tert-butyl ester-3-ethyl ester was isolated as a waxy solid. Yield 6.86 g (82%). MS (ES): m/z 258.2 $(M+H)^+$.

Step 2

1-(tert-Butyl) 3-ethyl 3-{[4-2-butynyloxy)phenyl]sulfonyl}-1,3-piperidine dicarboxylate To a stirred solution of diisopropylamine (7.2 g, 28 mmol) in THF (25 ml) at −78° C. was added n-butyllithium (1.6 m solution in hexanes, 19.0 ml, 30.8 mmol). The mixture was stirred for 30 min at 0° C. The mixture was then cooled to −78° C. and piperidine-1,3-dicarboxylic acid 1-tert-butyl ester 3-ethyl ester (5.3 g, 28 mmol) in THF (20 ml) was added slowly. The reaction mixture was stirred for 30 min then 4-but-2-ynyloxy-benzenesulfonyl fluoride (6.4 g, 28 mmol) in THF (15 ml) was added slowly. The reaction was warmed to room temperature and after 4 hrs quenched with ice water and extracted with chloroform. The organic layer was dried over sodium sulfate, filtered, concentrated and chromatographed on a silica-gel column with 20% ethyl acetate:hexane to afford 1-(tert-Butyl) 3-ethyl 3-{[4-2-butynyloxy)phenyl]sulfonyl}-1,3-piperidine dicarboxylate as a white solid. Yield 9.8 g (76%); mp 103.4° C.; MS (ES): m/z 466.4 (M+H)+. $^1H$ NMR (300 MHz, DMSO-$d_6$): δ1.07 (t, 3H), 1.34 (s, 9H), 3.31 (s, 3H), 3.84 (m, 2H), 4.00 (m, 4H), 4.53 (d, 2H), 4.91 (m, 4H), 7.22 (d, 2H), 7.71 (d, 2H).

Step 3

To a stirred solution of 1-(tert-Butyl) 3-ethyl 3-{[4-2-butynyloxy)phenyl]sulfonyl}-1,3-piperidine dicarboxylate (5.45 g, 11.7 mmol) in methylene chloride(25 ml) at 0° C. was added a saturated solution of hydrogen chloride in methylene chloride (25 ml). After 5 hours the solution was concentrated to afford ethyl 3-{[4-(2-butynyloxy)phenyl]sulfonyl}-3-piperidinecarboxylate hydrogen chloride and is stored under nitrogen. White hygroscopic solid; Yield 3.47 g (74%); MS (ES): m/z 366.2 $(M+H)^+$ Step 4

(Ethyl 3-{[4-(2-butynyloxy)phenyl]sulfonyl}-1-ethyl-3-piperidinecarboxylate)

3-{[4-(2-Butynyloxy)phenyl]sulfonyl}-3-piperidinecarboxylate hydrogen chloride (2.97 g, 8.0 mmol), ethyl iodide (1.28 g, 8 mmol) and dry powdered potassium carbonate (3.8 g) in dry acetone (60 ml) was heated to reflux for 18 hours. The mixture was allowed to cool and the potassium salts were filtered and concentrated. The residue was extracted with chloroform and washed with $H_2O$, dried over sodium sulfate and concentrated to afford ethyl 3-{[4-(2-butynyloxy)phenyl]sulfonyl}-1-ethyl-3-piperidinecarboxylate. This product was used without further purification. Amber gum, yield 3.47 g (99%); MS (ES): m/z 394 $(M+H)^+$.

Step 5

3-{[4-(2-butynyloxy)phenyl]sulfonyl}-1-ethyl-3-piperidinecarboxylic acid 3-{[4-(2-butynyloxy)phenyl]sulfonyl}-1-ethyl-3-piperidinecarboxylic acid was prepared starting from ethyl 3-{[4-(2-butynyloxy)phenyl]sulfonyl}-1-ethyl-3-piperidinecarboxylate (3.2 g, 8.0 mmol) dissolved in THF:Methanol (15:25 ml) and NaOH (15 ml). The resulting reaction misture was worked up as outlined in example 1 (step 7). Yield 2.11 g (71%), white solid: mp 159.2° C.; MS (ES): m/z 366.3 (M+H)+

Step 6

3-{[4-(2-butynyloxy)phenyl]sulfonyl}-1-ethyl-N-hydroxy-3-piperidinecarboxamide Starting from 3-{[4-(2-butynyloxy)phenyl]sulfonyl}-1-ethyl-3-piperidinecarboxylic acid (2.0 g, 5.5 mmol) and and following the procedure as outlined in example 1 (step 8), 0.193 g of 3-{[4-(2-butynyloxy)phenyl]sulfonyl}-1-ethyl-N-hydroxy-3-piperidinecarboxamide hydrogen chloride was isolated as a white solid. Yield 10%; mp 190.3° C.; MS (ES): m/z: 405.3 $(M+H)^+$; $^1H$ NMR (300 MHz, DMSO-$d_6$): δ1.18 (m, 3H), 1.97 (m, 2H), 2.55 (m, 2H), 3.21(m, 5H), 3.52 9S, 3H), 3.82 (d, 1H), 4.91 (m, 2H), 7.19 (d, 2H), 7.51 (s, 5H), 8.67 (s, 1H), 9.48 (s, 1H).

EXAMPLE 25

3-{[4-(2-butynyloxy)phenyl]sulfonyl}-1-(4-chlorobenzyl)-N-hydroxy-3-piperidinecarboxamide Step 1

Ethyl 3-{[4-(2-butynyloxy)phenyl]sulfonyl}-1-(4-chlorobenzyl)-3-piperidinecarboxylate Starting from ethyl 3-{[4-(2-butynyloxy)phenyl]sulfonyl}-3-piperidinecarboxylate hydrogen chloride (1 g, 2.7 mmol) and 4-chlorobenzyl chloride (0.485, 3.0 mmol) in dry acetone (50 ml) and following the procedure outlined in example 24, (step 4), Ethyl 3-{[4-(2-butynyloxy)phenyl]sulfonyl}-1-(4-chlorobenzyl)-3-piperidinecarboxylate was isolated as a brown oil. This product was taken to the next step without further purification. Yield 1.66 g (99%); MS (ES): m/z: 491.3 $(M+H)^+$ Step 2

3-{[4-(2-butynyloxy)phenyl]sulfonyl}-1-(4-chlorobenzyl)-3-piperidinecarboxylic acid 3-{[4-(2-butynyloxy)phenyl]sulfonyl}-1-(4-chlorobenzyl)-1-3-piperidinecarboxylic acid as prepared starting from ethyl 3-{[4-(2-butynyloxy)phenyl]sulfonyl}-1-(4-chlorobenzyl)-3-piperidinecarboxylate (1.64 g, 3.3 mmol) dissolved in THF:Methanol (15:50 ml) and NaOH (15 ml). The resulting reaction mixture was worked up as outlined in example 1 (step 7); Yield 1.11 g (75%), white solid: mp 115.2° C.; MS (ES): m/z 462.1 $(M+H)^+$ Step 3

3-{[4-(2-butynyloxy)phenyl]sulfonyl}-1-(4-chlorobenzyl)-N-hydroxy-3-piperidinecarboxamide Starting from 3-{[4-(2-butynyloxy)phenyl]sulfonyl}-1-(4-chlorobenzyl)-3-piperidinecarboxylic acid (1.1 g, 2.4 mmol) and and following the procedure as outlined in example 1, (step 8), 0.48 g of 3-{[4-(2-butynyloxy)phenyl]sulfonyl}-1-(4-chlorobenzyl)-3-N-hydroxy-3-piperidinecarboxamide hydrogen chloride was isolated as a white solid. Yield 43%; mp 124.4° C.; MS (ES): m/z: 477.1 $(M+H)^+$; $^1H$ NMR (300 MHz, DMSO-$d_6$): δ2.0 (m, 2H), 3.39 (m, 5H), 4.27 (d, 2H), 4.89 (m, 2H), 7.14 (d, 2H), 7.15 (m, 4H), 7,61 (d, 2H), 8.95 (s, 1H), 9.46 (s, 1H).

EXAMPLE 26

4-{[4-(2-Butynyloxy)phenyl]sulfonyl}-1-[4-(2-piperidin-1-yl-ethoxy)-benzyl]-piperidine-4-carboxylic acid hydroxyamide A mixture of diethanolamine (2.1 g, 20 mmol), 4-(2-piperidin-1-yl-ethoxy)-benzyl chloride (5.9 g, 20 mmol) and $KCO_3$ (10 g, excess) was refluxed in acetone (100 ml) for 24 hrs. At the end, reaction mixture was cooled to room temperature and filtered. It was concentrated to dryness and redissolved in touene (200 ml) and thionyl chloride (6.75 g, 50 mmol). It was heated to 80° C. for 1 hr and the separated brown solid, bis-(2-chloro-ethyl)-[4-(2-piperidin-1-yl-ethoxy)-benzyl]-amine was filtered and dried. The crude product was taken to next step with out purification. Yield: 7.0 g, (89%). 4-{[4-(2-Butynyloxy)phenyl]sulfonyl}-1-[4-(2-piperidin-1-yl-ethoxy)-benzyl]-piperidine-4-carboxylic acid ethylester was was prepared according to the general method as outlined in example 1 (step 6), starting from ethyl{[4-(2-butynyloxy)phenyl]sulfonyl}acetate (2.9 g, 10.0 mmol) and bis-(2-chloro-ethyl)-[4-(2-piperidin-1-yl-ethoxy)-benzyl]-amine dihydrochloride (4.3 g, 10 mmol), 2.8 g of product (brown oil) was isolated. Yield 48%; MS: 583 (M+H)$^+$ 4-{[4-(2-Butynyloxy)phenyl]sulfonyl}-1-[4-(2-piperidin-1-yl-ethoxy)-benzyl]-piperidine-4-carboxylic acid was prepared according to the general method as outlined in example 1 (step 7), starting from 4-{[4-(2-Butynyloxy)phenyl]sulfonyl}-1-[4-(2-piperidin-1-yl-ethoxy)-benzyl]-piperidine-4-carboxylic acid ethylester (3.0 g, 5.15 mmol); 2.2 g of white powder. mp: 172° C.; Yield 77%; MS: 555 (M+H)$^+$ Starting from 4-{[4-(2-Butynyloxy)phenyl]sulfonyl}-1-[4-(2-piperidin-1-yl-ethoxy)-benzyl]-piperidine-4-carboxylic acid (5.0 g, 9.0 mmol), and following the procedure as outlined in Example 1 (step 8), 1.8 g of 4-{[4-(2-Butynyloxy)phenyl]sulfonyl}-1-[4-(2-piperidin-1-yl-ethoxy)-benzyl]-piperidine-4-carboxylic acid hydroxyamide was isolated as an yellow spongy solid. The dihydrochloride salt was prepared by dissolving the free amine with methanolic hydrochloric acid. mp: 124° C.; Yield: 1.8 g (32%); MS: 570 (M+H)$^+$.

EXAMPLE 27

4-{[4-(2-Butynyloxy)phenyl]sulfonyl}-1-(3-pentanyl)-piperidine-4-carboxylic acid hydroxyamide 4-{[4-(2-Butynyloxy)phenyl]sulfonyl}-1-(3-pentanyl)-piperidine-4-carboxylic acid ethyl ester was was prepared according to the general method as outlined in example 1 (step 6), starting from ethyl{[4-(2-butynyloxy)phenyl]sulfonyl}acetate (8.8 g, 30.0 mmol) and bis-(2-chloro-ethyl)-(3-pentanyl)-amine dihydrochloride (7.4 g, 30 mmol), 3.5 g of product (brown oil) was isolated. Yield 26%; MS: 436 (M+H)$^+$ 4-{[4-(2-Butynyloxy)phenyl]sulfonyl}-1-(3-pentanyl)-piperidine-4-carboxylic acid was prepared according to the general method as outlined in example 1 (step 7), starting from 4-{[4-(2-Butynyloxy)phenyl]sulfonyl}-1-(3-pentanyl)-piperidine-4-carboxylic acid ethyl ester (3.0 g, 6.8 mmol); 2.5 g of spongy yellow solid. mp: 98° C.; Yield 90%; MS: 408 (M+H)$^+$ Starting from 4-{[4-(2-Butynyloxy)phenyl]sulfonyl}-1-(3-pentanyl)-piperidine-4-carboxylic acid (2.5 g, 6.1 mmol), and following the procedure as outlined in Example 1 (step 8), 1.8 g of 4-{[4-(2-Butynyloxy)phenyl]sulfonyl}-1-(3-pentanyl)-piperidine-4-carboxylic acid hydroxyamide was isolated as an yellow spongy solid. The hydrochloride salt was prepared by dissolving the free amine with methanolic hydrochloric acid. mp: 101–103° C.; Yield: 1.1 g (42%); MS: 460 (M+H)$^+$. $^1$H NMR (300 MHz, DMSO-d$_6$): δ1.8 (t, 6H), 1.5–1.7 (m, 6H), 1.9 (s, 3H), 2.3–2.7 (m, 8H), 3.0 (m, 2H), 3.4 (s, 3H), 3.6 (d, 2H), 4.9 (s, 2H), 7.21 (d, 2H), 7.8 (d, 2H), 9.3 (s, 1H), 9.8 (s, 1H), 11.2 (s, 1H).

EXAMPLE 28

1-(4-Methoxy-benzyl)-4-(4-prop-2-ynyloxy-benzenesulfonyl)-piperidine-4-carboxylic acid hydroxyamide 1-(4-Methoxy-benzyl)-4-(4-prop-2-ynyloxy-benzenesulfonyl)-piperidine-4-carboxylic acid ethyl ester was prepared according to the general method as outlined in example 1 (step 6), starting from (4-prop-2-ynyloxy-benzenesulfonyl)-acetic acid ethyl ester (prepared as described in example 11, step 1 and 2)(10.0 g, 35.0 mmol) and 4-methoxy-benzyl)-bis-(2-chloro-ethyl)-amine hydrochloride (10.5 g, 35 mmol), 6.0 g of product (brown oil) was isolated. Yield 36%; MS: 472 (M+H)$^+$ 1-(4-Methoxy-benzyl)-4-(4-prop-2-ynyloxy-benzenesulfonyl)-piperidine-4-carboxylic acid was prepared according to the general method as outlined in example 1 (step 7), starting from 1-(4-Methoxy-benzyl)-4-(4-prop-2-ynyloxy-benzenesulfonyl)-piperidine-4-carboxylic acid ethyl ester (6.0 g, 12.73 mmol); 5.0 g of spongy yellow solid. mp: 208° C.; Yield 92%; MS: 444 (M+H)$^+$ Starting from 1-(4-Methoxy-benzyl)-4-(4-prop-2-ynyloxy-benzenesulfonyl)-piperidine-4-carboxylic acid (6.0 g, 13.5 mmol), and following the procedure as outlined in Example 1 (step 8), 2.0 g of 1-(4-Methoxy-benzyl)-4-(4-prop-2-ynyloxy-benzenesulfonyl)-piperidine-4-carboxylic acid hydroxyamide was isolated as an yellow spongy solid. The hydrochloride salt was prepared by dissolving the free amine with methanolic hydrochloric acid. mp: 150° C.; Yield: 2.0 g (29%); MS: 459 (M+H)$^+$. $^1$H NMR (300 MHz, DMSO-d$_6$): δ2.3–2.8 (m, 6H), 3.3 (d, 2H), 3.5 (s, 3H), 4.2 (s, 2H), 5.0 (s, 2H), 7.3 (d, 2H), 7.5 (d, 2H), 7.6 (d, 2H), 7.7 (d, 2H),10.9 (s, 1H), 11.2 (s, 1H).

EXAMPLE 29

1-(4-Chloro-benzyl)-4-(4-prop-2-ynyloxy-benzenesulfonyl)-piperidine-4-carboxylic acid hydroxyamide 1-(4-Chloro-benzyl)-4-(4-prop-2-ynyloxy-benzenesulfonyl)-piperidine-4-carboxylic acid ethyl ester was prepared according to the general method as outlined in example 1 (step 6), starting from (4-prop-2-ynyloxy-benzenesulfonyl)-acetic acid ethyl ester (prepared as described in example 11, step 1 and 2)(10.0 g, 35.0 mmol) and 4-chloro-benzyl)-bis-(2-chloro-ethyl)-amine hydrochloride (10.5 g, 35 mmol), 8.0 g of product (brown oil) was isolated. Yield 48%; MS: 475 (M+H)$^+$ 1-(4-Chloro-benzyl)-4-(4-prop-2-ynyloxy-benzenesulfonyl)-piperidine-4-carboxylic acid was prepared according to the general method as outlined in example 1 (step 7), starting from 1-(4-chloro-benzyl)-4-(4-prop-2-ynyloxy-benzenesulfonyl)-piperidine-4-carboxylic acid ethyl ester (6.0 g, 12.63 mmol); 5.0 g of spongy yellow solid. mp: 205° C.; Yield 92%; MS: 448 (M+H)$^+$ Starting from 1-(4-Chloro-benzyl)-4-(4-prop-2-ynyloxy-benzenesulfonyl)-piperidine-4-carboxylic acid (6.0 g, 13.4 mmol), and following the procedure as outlined in Example 1 (step 8), 2.0 g of 1-(4-chloro-benzyl)-4-(4-prop-2-ynyloxy-benzenesulfonyl)-piperidin-4-carboxylic acid hydroxyamide was isolated as an yellow spongy solid. The hydrochloride salt was prepared by dissolving the free amine with methanolic hydrochloric. acid. mp: 146° C.; Yield: 4.0 g (59%); MS: 499 (M+H)$^+$. $^1$H NMR (300 MHz, DMSO-d$_6$): δ2.0–2.5 (m, 6H), 3.2 (d, 2H), 4.18 (s, 2H), 4.9 (s, 2H), 7.42 (d, 2H), 7.61 (d, 2H), 7.71 (d, 2H), 7.85 (d, 2H),11.0 (s, 1H), 11.2 (s, 1H).

EXAMPLE 30 tert-butyl-4-({[4-(2-butynyloxy)phenyl]sulfanyl}methyl)-4-[(hydroxyamino)carbonyl]-1-piperidinecarboxylate Step 1

Piperidine-1,4-dicarboxylic acid tert-butyl ester ethyl ester

To a solution of of ethyl isonipecotate (4.72 g, 0.03 mmol) in 30 mL of THF was added slowly di-tert-butyl dicarbonate (7.2 g, 0.03 mmol) at room temperature. The resulting mixture was stirred for two hours and diluted with EtOAc. The organics were washed with brine, dried over MgSO$_4$, filtered and concentrated in vacuo. The residue was chromatographed on silica gel eluting with ethyl acetate:hexanes (1:9) to provide 7.52 g (97%) of the desired product as a colorless oil. Electrospray Mass Spec: 258.3 (M+H)$^+$ Step 2

1-(tert-Butyl) 4-ethyl 4-(iodomethyl)piperidine-1,4-dicarboxylate

To a solution of piperidine-1,4-dicarboxylic acid tert-butyl ester ethyl ester (12.8 g, 49.74 mmol) in 73 mL of dry THF under N$_2$ atmosphere at −42° C. was added 24.87 mL (49.74 mmol) of 2M Lithium diisopropylamine in heptane/THF/ethylbenzene dropwise to not exceed −40° C. After one hour, 4.0 mL (49.74 mmol) of diiodomethane was added and the solution was warmed to ambient temperature overnight. The resulting solution was diluted with H$_2$O and extracted with ethyl acetate. The organics were washed with brine, dried over MgSO$_4$, filtered and concentrated in vacuo to provide 18.84 g (95%) of the desired product as a brown oil. Electrospray Mass Spec: 398.2 (M+H)$^+$ Step 3

4-But-2-ynyloxy-benzenesulfonic acid sodium salt

To a solution of 4-hydroxybenzenesulfonate sodium salt (52.35 g, 0.225) in 1 L of isopropanol and 225 mL of a 1.0N solution of sodium hydroxide was added 59.96 g (0.45 mol) of 1 bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 45.08 g (81%) of the desired product as a white solid.

Step 4

4-But-2-ynyloxy-benzenesulfonyl chloride

To a stirred solution of oxalyl chloride (47.8 ml, 0.545 mol) at 0° C. in 240 mL of CH$_2$Cl$_2$ was added a DMF (43.0 ml) solution of 4-but-2-ynyloxy-benzenesulfonic acid sodium salt in a drop wise manner. The reaction mixture was stirred at 0° C. for 30 min and then let warm to room temperature and stirred for 18 h. The reaction was then poured into ice and extracted with hexanes. The organics were washed with water and brine, dried over MgSO$_4$, filtered and concentrated in vacuo to provide 42.0 g (95%) of the desired product as yellow solid.

Step 5

4-But-2-ynyloxy-benzenethiol

To a solution of 11.8 g (0.045 mol) of triphenylphosphine in 10 mL of CH$_2$Cl$_2$ and 0.3 mL of DMF was added dropwise a solution of 4-but-2-ynyloxy-benzenesulfonyl chloride in 15 mL CH$_2$Cl$_2$. Stirred at room temperature for two hours, added 5 mL of 1N HCl, stirred for 30 min., and then added 15 mL of brine. The organics were separated and concentrated in vacuo. The residue was diluted with ether and filtered the insolubles. The filtrate was washed with 2.5N NaOH and the aqueous solution separated, acidified and extracted with ether. The organics were washed with H$_2$O, brine, dried over MgSO$_4$, filtered and concentrated in vacuo to give 1.54 g (58%) of the desired product as a pale yellow oil.

Step 6

1-(tert-butyl) 4-ethyl 4-({[4-(2-butynyloxy)phenyl]sulfanyl}methyl)-1,4-piperidinedicarboxylate A mixture of 0.294 g (0.74 mmol) of 1-(tert-Butyl) 4-ethyl 4-(iodomethyl)piperidine-1,4-dicarboxylate, 0.145 (0.814 mmol) of 4-but-2-ynyloxy-benzenethiol and 0.204 g (1.48 mmol) of K$_2$CO$_3$ in 2.0 mL of DMF was stirred at room temperature for 18 h. The resulting mixture was diluted with EtOAc, washed with H$_2$O, brine, dried over MgSO$_4$ and concentrated in vacuo. The residue was chromatographed on silica gel eluting with EtOAc:Hexanes (1:19) to provide 0.328 g (99%) of the desired product as a colorless oil. Electrospray Mass Spec: 448.3 (M+H)$^+$ Step 7

4-(4-But-2-ynyloxy-phenylsulfanylmethyl)-piperidine-1,4-dicarboxylic acid mono-tert-butyl ester A mixture of 0.288 g (0.0643 mmol) of 1-(tert-butyl)4-ethyl 4-({[4-(2-butynyloxy)phenyl]sulfanyl}methyl)-1,4-piperidinedicarboxylate, 3.25 mL of 1N NaOH 3.25 mL of THF and 3.25 mL of MeOH was heated to reflux for 3 h. The organics were removed and the residue was diluted with H$_2$O, acidified and extracted with EtOAC. The organics were washed with H$_2$O, brine, dried over mgSO$_4$, filtered and concentrated in vacuo to provide 0.241 g (89%) of the desired product as an off white gum. Electrospray Mass Spec: 464.3 (M+FA−H)$^−$ Step 8

WAY 173665 tert-butyl-4-({[4-(2-butynyloxy)phenyl]sulfanyl}methyl)-4-[(hydroxyamino)carbonyl]-1-piperidinecarboxylate To a solution of 0.204 g (0.49 mmol) of 4-(4-But-2-ynyloxy-phenylsulfanylmethyl)-piperidine-1,4-dicarboxylic acid mono-tert-butyl ester, 0.079 g (0.58 mmol) of 1-hydroxybenzotriazole in 2.5 mL of DMF was added 0.112 g (0.84 mmol) of 1-(3-dimethylaminopropyl)-3-ethylcarbodiimide hydrochloride, and stirred at room temperature for 1 h. Then added 0.3 mL of 50% aqueous hydroxylamine and stirred for 18 h. The resulting mixture was diluted with EtOAc, washed with H$_2$O, brine, dried over MgSO$_4$, filtered and concentrated in vacuo. The residue was chromatographed on silica gel eluting with 1.5% MeOH/

CH$_2$Cl$_2$ to provide 0.077 g (36%) of the desired product as a white solid. Electrospray Mass Spec: 435.2 (M+H)$^+$

EXAMPLE 31

4-({[4-(But-2-ynyloxy)phenyl]thio}methyl)-N-hydroxypiperidine-4-carboxamide To a solution of 0.143 g (0.033 mmol) of tert-butyl-4-({[4-(2-butynyloxy)phenyl]sulfanyl}methyl)-4-[(hydroxyamino)carbonyl]-1-piperidinecarboxylate in 5 mL of CH$_2$Cl$_2$ and 1 mL of MeOH was added 5 mL of 4M HCl in dioxane and stirred for 1 h. The reaction was concentrated in vacuo and the residue was triturated with ether and filtered to provide 0.093 g (76%) of the desired product as a pale orange solid. Electrospray Mass Spec: 335.3 (M+H)$^+$

EXAMPLE 32 tert-Butyl-4-({[4-(2-butynyloxy)phenyl]sulfinyl}methyl)-4-[(hydroxyamino)carbonyl]-1-piperidinecarboxylate To a slurry of tert-butyl-4-({[4-(2-butynyloxy)phenyl]sulfanyl}methyl)-4-[(hydroxyamino)carbonyl]-1-piperidinecarboxylate (0.24 g, 0.55 mmol) at 0° C. in 7 mL of MeOH was added dropwise 3.5 mL of 30% hydrogen peroxide. The reaction was allowed to warm to room temperature and stirred for 18 h. The reaction was cooled to 0° C. and quenched with 3.5 mL of a saturated solution of Na$_2$SO$_3$. The organics were removed and the aqueous solution was extracted with CH$_2$Cl$_2$. The organics were washed with H$_2$O, brine, dried over MgSO$_4$, filtered and concentrated in vacuo. The residue was triturated with ether to provide 0.166 g (67%) of the desired product as an off white solid. Electrospray Mass Spec: 451.3 (M+H)$^+$

EXAMPLE 33

4-[[[4-(2-Butynyloxy)phenyl]sulfinyl]methyl]-N-hydroxy-4-piperidinecarboxamide 4-({[4-(2-Butynyloxy)phenyl]sulfinyl}methyl)-N-hydroxy-4-piperidinecarboxamide was prepared according to the general method as outlined in Example 31. Starting from tert-butyl-4-({[4-(2-butynyloxy)phenyl]sulfinyl}methyl)-4-[(hydroxyamino)carbonyl]-1-piperidinecarboxylate (0.082 g, 0.18 mmol), 0.066 g (95%) of the desired product was isolated as a white solid. Electrospray Mass Spec: 351.2 (M+H)$^+$

EXAMPLE 34 tert-Butyl-4-({[4-(but-2-ynyloxy)phenyl]sulfonyl}methyl)-4-[(hydroxyamino)carbonyl]piperidine-1-carboxylate To a solution of tert-butyl-4-({[4-(2-butynyloxy)phenyl]sulfanyl}methyl)-4-[(hydroxyamino)carbonyl]-1-piperidinecarboxylate (0.422 g, 0.97 mmol) in 8 mL of MeOH, 4 mL of CH$_2$Cl$_2$ and 2 mL of THF was added a solution of 1.79 g (2.91 mmol) of OXONE in 8 mL of H$_2$O and stirred at room temperature for 18 h. The solid was filtered and the filtrate was concentrated in vacuo. The residue was diluted with EtOAc, washed with H$_2$O, brine, dried over MgSO$_4$, filtered, and concentrated to provide 0.351 g (77%) of the desired product as a white solid. Electrospray Mass Spec: 467.3 (M+H)$^+$

EXAMPLE 35 tert-butyl-4-({[4-(2-butynyloxy)phenyl]sulfonyl}methyl)-4-[(hydroxyamino)carbonyl]-1-piperidinecarboxylate tert-Butyl-4-({[4-(2-butynyloxy)phenyl]sulfonyl}methyl)-4-[(hydroxyamino)carbonyl]-1-piperidinecarboxylate was prepared according to the general method as outlined in Example 31. Starting from tert-Butyl-4-({[4-(but-2-ynyloxy)phenyl]sulfonyl}methyl)-4-[(hydroxyamino)carbonyl]piperidine-1-carboxylate (0.10 g,0.214 mmol) 0.074 g (86%) of the desired product was isolated as white solid. Electrospray Mass Spec: 367.3 (M+H)$^+$

EXAMPLE 36

1-Acetyl-4-[[[4-(2-butynyloxy)phenyl]sulfonyl]methyl]-N-hydroxy-4-piperidinecarboxamide Step 1

4-[[[4-(2-Butynyloxy)phenyl]sulfonyl]methyl]-1,4-piperidine dicarboxylic acid, 1-tert-butyl 4-ethyl ester To a solution of 1-(tert-butyl) 4-ethyl 4-({[4-(2-butynyloxy)phenyl]sulfanyl}methyl)-1,4-piperidinedicarboxylate (1.66 g, 3.7 mmol) (prepared in example 30, step 6) in 20 mL of CH$_2$Cl$_2$ was added tetrabutylammonium oxone (17.38 g, 14.7 mmol) and stirred at room temperature for 18 h. The reaction was concentrated in vacuo and the residue was diluted with EtOAc, washed with H$_2$O, 5% KHSO$_4$, brine, dried over MgSO$_4$, filtered and concentrated to provide 1.69 g (95%) of the desired product as a pale yellow gum. Electrospray Mass Spec: 480.3 (M+H)$^+$ Step 2

4-[[[4-(2-Butynyloxy)phenyl]sulfonyl]methyl]-4-piperidinecarboxylic acid, ethyl ester 4-[[[4-(2-Butynyloxy)phenyl]sulfonyl]methyl]-4-piperidinecarboxylic acid ethyl ester was prepared according to the general method as outlined in Example 31. Starting from 4-[[[4-(2-Butynyloxy)phenyl]sulfonyl]methyl]-1,4-piperidinedicarboxylic acid 1-tert-butyl 4-ethyl ester (1.62 g 3.4 mmol), 1.335 g (95%) of the desired product was isolated as a tan solid. Electrospray Mass Spec: 380.2 (M+H)$^+$ Step 3

1-Acetyl-4-[[[4-(2-butynyloxy)phenyl]sulfonyl]methyl]-4-piperidinecarboxylic acid, ethyl ester To a solution of 4-[[[4-(2-Butynyloxy)phenyl]sulfonyl]methyl]-4-piperidinecarboxylic acid ethyl ester (0.24 g, 0.576 mmol), triethylamine (0.32 ml) and catalytic amount of 4-Dimethylaminopyridine in 6.0 mL of CH$_2$Cl$_2$ was added a solution of acetyl chloride (0.068 ml, 0.864 mmol) in 1.0 mL of CH$_2$Cl$_2$. The reaction stirred at room temperature for 4 h and washed with H$_2$O, brine, dried over MgSO$_4$, filtered through a pad of silica gel and concentrated to provide 0.242 g (100%) of the desired product as a colorless gum. Electrospray Mass Spec: 422.2 (M+H)$^+$ Step 4

1-Acetyl-4-(4-but-2-ynyloxy-benzenesulfonylmethyl)-piperidine-4-carboxylic acid 1-Acetyl-4-(4-but-2-ynyloxy-benzenesulfonylmethyl)-piperidine-4-carboxylic acid was prepared according to the general method as outlined in Example 30, (step 7). Starting from 1-Acetyl-4-[[[4-(2-butynyloxy)phenyl]sulfonyl]methyl]-4-piperidinecarboxylic acid, ethyl ester (0.22 g, 0.524 mmol), 0.141 g of the desired product was isolated as a pale yellow solid. Electrospray Mass Spec: 438.2 (M+FA–H)$^-$ Step 5

1-Acetyl-4-[[[4-(2-butynyloxy)phenyl]sulfonyl]
methyl]-N-hydroxy-4-piperidinecarboxamide 1-Acetyl-4-[[[4-(2-butynyloxy)phenyl]sulfonyl]methyl]-N-hydroxy-4-piperidinecarboxamide was prepared according to the general method as outlined in Example 30 (step 8). Starting from 1-Acetyl-4-(4-but-2-ynyloxy-benzenesulfonylmethyl)-piperidine-4-carboxylic acid, (0.122 g, 0.31 mmol) 0.048 g (38%) of the desired product was isolated as a pale yellow solid. Electrospray Mass Spec: 409.2 $(M+H)^+$

EXAMPLE 37

1-(2-Butynyl)-4-({[4-(2-butynyloxy)phenyl]
sulfonyl}methyl)-N-hydroxy-4-
piperidinecarboxamide hydrochloride Step 1

1-(2-Butynyl)-4-[[[4-(2-butynyloxy)phenyl]sulfonyl]
methyl]-4-piperidinecarboxylic acid, ethyl ester A mixture of 4-[[[4-(2-Butynyloxy)phenyl]sulfonyl]methyl]-4-piperidinecarboxylic acid ethyl ester (0.208 g, 0.5 mmol), 1-bromo-2-butyne (0.044 ml, 0.53 mmol) and $K_2CO_3$ (0.138 g, 1.0 mmol) in 5.0 mL of DMF was stirred at room temperature for 6 h. The reaction was diluted with EtOAc and washed with $H_2O$, brine, dried over $MgSO_4$, filtered, and concentrated in vacuo. The residue was chromatographed on silica gel eluting with EtOAc:hexanes (1:1) to provide 0.183 g (85%) of the desired product as a pale yellow gum. Electrospray Mass Spec: 432.2 $(M+H)^+$ Step 2

1-(2-Butynyl)-4-[4-(2-butynyloxy)
benzenesulfonylmethyl]-piperidine-4-carboxylic
acid 1-(2-Butynyl)-4-[4-(2-butynyloxy)benzenesulfonylmethyl]-piperidine-4-carboxylic acid was prepared according to the general method as outlined in example 30 (step 7). Starting from 1-(2-Butynyl)-4-[[[4-(2-butynyloxy)phenyl]sulfonyl]methyl]-4-piperidinecarboxylic acid, ethyl ester, (0.153 g, 0.354 mmol), 0.12 g (84%) of the desired product was isolated as a white solid. Electrospray Mass Spec: 404.2 $(M+H)^+$ Step 3

1-(2-Butynyl)-4-({[4-(2-butynyloxy)phenyl]
sulfonyl}methyl)-N-hydroxy-4-
piperidinecarboxamide hydrochloride 1-(2-Butynyl)-4-({[4-(2-butynyloxy)phenyl]sulfonyl}methyl)-N-hydroxy-4-piperidinecarboxamide hydrochloride was prepared according to the general method as outlined in Example 30 (step 8). Starting from 1-(2-butynyl)-4-[4-(2-butynyloxy)benzenesulfonylmethyl]-piperidine-4-carboxylic acid, (0.15 g, 0.34 mmol), 0.05 g of the desired product, which was dissolved in 1.0 mL of $CH_2Cl_2$ and treated with 0.225 mL of 1M HCl in $CH_2Cl_2$. The solution was stirred for 1 h, and concentrated in vacuo. The residue was triturated with ether to provide 0.044 g (28%) of the hydrochloride of the desired product as a beige solid. Electrospray Mass Spec: 419.2 $(M+H)^+$

EXAMPLE 38

N~1~-(tert-Butyl)-4-({[4-(2-butynyloxy)phenyl]
sulfonyl}methyl)-N~4~-hydroxy-1,4-[4-(2-
butynyloxy)phenyl]sulfonyl}methyl)-N~4~-
hydroxy-1,4-1]sulfonyl}methyl)-N~4~-hydroxy-1,4-
piperidinedicarboxamide Step 1

1-tert-Butylcarbamoyl-4-(4-but-2-ynyloxy-
benzenesulfonylmethyl)-piperidine-4-carboxylic
acid ethyl ester To a solution of tert-butylisocyanate (0.097 ml, 0.85 mmol) in 8.0 mL of $CH_2Cl_2$, was added 4-[[[4-(2-Butynyloxy)phenyl]sulfonyl]methyl]-4-piperidinecarboxylic acid ethyl ester (prepared from example 36, step 2) (0.337 g, 0.81 mmol) and triethylamine (0.135 ml, 0.97 mmol) and stirred at room temperature for 2 h. The reaction was diluted with $CH_2Cl_2$ and washed with $H_2O$, brine, dried over $MgSO_4$, filtered, and concentrated in vacuo. The residue was triturated with ether:hexanes (1:1) to provide 0.284 g (73%) of the desired product as a white solid. Electrospray Mass Spec: 479.2 $(M+H)^+$ Step 2

1-[(tert-Butylamino)carbonyl]-4-({[4-(2-butynyloxy)
phenyl]sulfonyl}methyl)-4-onyl]-4-({[4-(2-
butynyloxy)phenyl]sulfonyl}methyl)-4-
piperidinecarboxylic acid 1-[(tert-Butylamino)carbonyl]-4-({[4-(2-butynyloxy)phenyl]sulfonyl}methyl)-4-onyl]-4-({[4-(2-butynyloxy)phenyl]sulfonyl}methyl)-4-piperidinecarboxylic acid was prepared according to the general method as outlined in Example 30 (step 7). Starting from 1-tert-butylcarbamoyl-4-(4-but-2-ynyloxy-benzenesulfonylmethyl)-piperidine-4-carboxylic acid ethyl ester (0.259 g, 0.54 mmol), 0.169 g, (69%) of the desired product was isolated as white solid. Electrospray Mass Spec: 451.4 $(M+H)^+$ Step 3

N~1~-(tert-Butyl)-4-({[4-(2-butynyloxy)phenyl]
sulfonyl}methyl)-N~4~-hydroxy-1,4-[4-(2-
butynyloxy)phenyl]sulfonyl}methyl)-N~4~-
hydroxy-1,4-1]sulfonyl}methyl)-N~4~-hydroxy-1,4-
piperidinedicarboxamide N~1~-(tert-Butyl)-4-({[4-(2-butynyloxy)phenyl]sulfonyl}methyl)-N~4~-hydroxy-1,4-[4-(2-butynyloxy)phenyl]sulfonyl}methyl)-N~4~-hydroxy-1,4-1]sulfonyl}methyl)-N~4~-hydroxy-1,4-piperidinedicarboxamide was prepared according to the general method as outlined in Example 30 (step 8). Starting from 1-[(tert-Butylamino)carbonyl]-4-({[4-(2-butynyloxy)phenyl]sulfonyl}methyl)-4-onyl]-4-({[4-(2-butynyloxy)phenyl]sulfonyl}methyl)-4-piperidinecarboxylic acid (0.149 g, 0.33 mmol), 0.077 g of the desired product was isolated as pale yellow solid. Electrospray Mass Spec: 466.3 $(M+H)^+$

EXAMPLE 39

Methyl 4-({[4-(2-butynyloxy)phenyl]
sulfonyl}methyl)-4-[(hydroxyamino)carbonyl]-1-
piperidinecarboxylate Step 1

4-(4-But-2-ynyloxy-benzenesulfonylmethyl)-
piperidine-1,4-dicarboxylic acid ethyl ester methyl
ester To a solution of 4-[[[4-(2-Butynyloxy)phenyl]sulfonyl]methyl]-4-piperidinecarboxylic acid ethyl ester (0.354 g, 0.85 mmol) in 1.0 mL of $CH_2Cl_2$ under $N_2$ atmosphere was added dropwise a solution of N,O-bis(trimethylsilyl) acetamide (0.462 ml, 1.87 mmol) in 0.5 mL of $CH_2Cl_2$ and stirred for 1 h. The reaction was cooled to 0° C. and added dropwise a solution of 0.079 mL (1.02 mmol) of methyl-chloroformate in 0.5 mL of $CH_2Cl_2$. The reaction was allowed to stir at room temperature for 1 h and cooled to 0° C., quenched with pH 7 buffer solution and extracted with EtOAc. The organics was washed with $H_2O$, brine, dried over $MgSO_4$, filtered, and concentrated in vacuo. The residue was chromatographed on silica gel eluting with EtOAc:hexanes (1:2) to provide 0.315 g (85%) of the desired product as a colorless oil. Electrospray Mass Spec: 438.3 $(M+H)^+$ Step 2

4-(4-But-2-ynyloxy-benzenesulfonylmethyl)-piperidine-1,4-dicarboxylic acid monomethyl ester 4-(4-But-2-ynyloxy-benzenesulfonylmethyl)-piperidine-1,4-dicarboxylic acid monomethyl ester was prepared according to the general method as outlined in Example 30 (step 7). Starting from 4-(4-But-2-ynyloxy-benzenesulfonylmethyl)-piperidine-1,4-dicarboxylic acid ethyl ester methyl ester (0.277 g, 0.633 mmol), 0.175 g (67%) of the desired product was isolated as white solid. Electrospray Mass Spec: 410.2 $(M+H)^+$ Step 3

Methyl 4-({[4-(2-butynyloxy)phenyl] sulfonyl}methyl)-4-[(hydroxyamino)carbonyl]-1-piperidinecarboxylate Methyl-4-({[4-(2-butynyloxy)phenyl]sulfonyl}methyl)-4-[(hydroxyamino)carbonyl]-1-piperidinecarboxylate was prepared according to the general method as outlined in Example 30 (step 8). Starting from 4-(4-But-2-ynyloxy-benzenesulfonylmethyl)-piperidine-1,4-dicarboxylic acid monomethyl ester (0.15 g, 0.366 mmol), 0.053 g (34%) of the desired product was isolated as a white solid. Electrospray Mass Spec: 425.3 $(M+H)^+$

EXAMPLE 40

Benzyl 4-({[4-(2-butynyloxy)phenyl] sulfonyl}methyl)-4-[(hydroxyamino)carbonyl]-1-piperidinecarboxylate Step 1

4-(4-But-2-ynyloxy-benzenesulfonylmethyl)-piperidine-1,4-dicarboxylic acid benzyl ester ethyl ester 4-(4-But-2-ynyloxy-benzenesulfonylmethyl)-piperidine-1,4-dicarboxylic acid benzyl ester ethyl ester was prepared according to the general method as outlined in Example 39 (step 1). Starting from 4-[[[4-(2-Butynyloxy)phenyl] sulfonyl]methyl]-4-piperidinecarboxylicacid ethyl ester (0.312 g, 0.75), 0.337 g (87%) of the desired product was isolated as colorless oil. Electrospray Mass Spec: 514.2 $(M+H)^+$ Step 2

4-(4-But-2-ynyloxy-benzenesulfonylmethyl)-piperidine-1,4-dicarboxylic acid monobenzyl ester 4-(4-But-2-ynyloxy-benzenesulfonylmethyl)-piperidine-1,4-dicarboxylic acid monobenzyl ester was prepared according to the general method as outlined in Example 30 (step 7). Starting from 4-(4-But-2-ynyloxy-benzenesulfonylmethyl)-piperidine-1,4-dicarboxylic acid benzyl ester ethyl ester (0.32 g, 0.623 mmol), 0.2 g of the desired product was isolated as white solid. Electrospray Mass Spec: 484.2 $(M-H)^-$ Step 3

Benzyl 4-({[4-(2-butynyloxy)phenyl] sulfonyl}methyl)-4-[(hydroxyamino)carbonyl]-1-piperidinecarboxylate Benzyl 4-({[4-(2-butynyloxy)phenyl]sulfonyl}methyl)-4-[(hydroxyamino)carbonyl]-1-piperidinecarboxylate was prepared according to the general method as outlined in Example 30, (step 8). Starting from 4-(4-But-2-ynyloxy-benzenesulfonylmethyl)-piperidine-1,4-dicarboxylic acid monobenzyl ester (0.18 g, 0.37 mmol), 0.106 g (57%) of the desored product was isolated as off-white solid. Electrospray Mass Spec: 501.3 $(M+H)^+$

EXAMPLE 41

1-Benzyl-4-({[4-(2-butynyloxy)phenyl] sulfonyl}methyl)-N-hydroxy-4-butynyloxy)phenyl] sulfonyl}methyl)-N-hydroxy-4-piperidinecarboxamide Step 1

Ethyl-1-benzyl-4-({[4-(2-butynyloxy)phenyl] sulfonyl}methyl)-4-4-(2-butynyloxy)phenyl] sulfonyl}methyl)-4-piperidinecarboxylate Ethyl-1-benzyl-4-({[4-(2-butynyloxy)phenyl] sulfonyl}methyl)-4-4-(2-butynyloxy)phenyl] sulfonyl}methyl)-4-piperidinecarboxylate was prepared according to the general method as outlined in Example 37 (step 1). Starting from 4-[[[4-(2-Butynyloxy)phenyl] sulfonyl]methyl]-4-piperidinecarboxylicacid ethyl ester (prepared in Example 36, step 2) (0.312 g,0.75 mmol), 0.265 g of the desired product was isolated as white solid. Electrospray Mass Spec: 470.2 $(M+H)^+$ Step 2

1-Benzyl-4-({[4-(2-butynyloxy)phenyl] sulfonyl}methyl)-4-piperidinecarboxylic-benzyl-4-({ [4-(2-butynyloxy)phenyl]sulfonyl}methyl)-4-piperidinecarboxylic acid 1-Benzyl-4-({[4-(2-butynyloxy)phenyl] sulfonyl}methyl)-4-piperidinecarboxylic benzyl-4-({[4-(2-butynyloxy)phenyl]sulfonyl}methyl)-4-piperidinecarboxylic acid was prepared according to the general method as outlined in Example 30 (step 7). Starting from Ethyl-1-benzyl-4-({[4-(2-butynyloxy)phenyl] sulfonyl}methyl)-4-4-(2-butynyloxy)phenyl] sulfonyl}methyl)-4-piperidinecarboxylate (0.25 g, 0.53 mmol), 0.227 g (90%) of the desired product was isolated as a white solid. Electrospray Mass Spec: 442.2 $(M+H)^+$ Step 3

1-Benzyl-4-({[4-(2-butynyloxy)phenyl] sulfonyl}methyl)-N-hydroxy-4-utynyloxy)phenyl] sulfonyl}methyl)-N-hydroxy-4-piperidinecarboxamide 1-Benzyl-4-({[4-(2-butynyloxy)phenyl] sulfonyl}methyl)-N-hydroxy-4-utynyloxy)phenyl] sulfonyl}methyl)-N-hydroxy-4-piperidinecarboxamide was prepared according to the general method as outlined in Example 30 (step 8). Starting from 1-Benzyl-4-({[4-(2-butynyloxy)phenyl]sulfonyl}methyl)-4- piperidinecarboxylic-enzyl-4-({[4-(2 butynyloxy)phenyl]sulfonyl}methyl)-4-piperidinecarboxylic acid (0.211 g, 0.44 mmol), 0.108 g of the desired product was isolated as white solid. Electrospray Mass Spec: 457.2 (M+H)$^+$

EXAMPLE 42

4-({[4-(2-Butynyloxy)phenyl]sulfonyl}methyl)-N-hydroxy-1-[(2,2,5-trimethyl-1,3-dioxan-5-yl)carbonyl]-4-piperidinecarboxamide Step 1

Ethyl 4-({[4-(2-butynyloxy)phenyl]sulfonyl}methyl)-1-[(2,2,5-trimethyl-1,3-dioxan-5-yl)carbonyl]-4-piperidinecarboxylate Ethyl 4-({[4-(2-butynyloxy)phenyl]sulfonyl}methyl)-1-[(2,2,5-trimethyl-1,3-dioxan 5-yl)carbonyl]-4-piperidinecarboxylate was prepared according to the general method as outlined in Example 30 (step 8). Starting from 4-[[[4-(2-Butynyloxy)phenyl]sulfonyl]methyl]-4-piperidinecarboxylicacid ethyl ester (0.333 g, 0.8 mmol) and 2,2,5-trimethyl-(1,3)dioxane-5-carboxylic acid (0.168 g, 0.96 mmol), 0.339 g (79%) of the desired product was isolated as a white solid. Electrospray Mass Spec: 536.1 (M+H)$^+$ Step 2

4-({[4-(2-Butynyloxy)phenyl]sulfonyl}methyl)-1-[(2,2,5-trimethyl-1,3-dioxan-5-yl)carbonyl]-4-piperidinecarboxylic acid 4-({[4-(2-Butynyloxy)phenyl]sulfonyl}methyl)-1-[(2,2,5-trimethyl-1,3-dioxan-5-yl)carbonyl]-4-piperidinecarboxylic acid was prepared according to the general method as outlined in Example 30 (step 7). Starting from ethyl 4-({[4-(2-butynyloxy)phenyl]sulfonyl}methyl)-1-[(2,2,5-trimethyl-1,3-dioxan-5-yl)carbonyl]-4-piperidinecarboxylate (0.299 g, 0.558 mmol), 0.235 g (83%) of the desired product was isolated as white solid. Electrospray Mass Spec: 506.2 (M−H)$^-$ Step 3

4-({[4-(2-Butynyloxy)phenyl]sulfonyl}methyl)-N-hydroxy-1-[(2,2,5-trimethyl-1,3-dioxan-5-yl)carbonyl]-4-piperidinecarboxamide 4-({[4-(2-Butynyloxy)phenyl]sulfonyl}methyl)-N-hydroxy-1-[(2,2,5-trimethyl-1,3-dioxan-5-yl)carbonyl]-4-piperidinecarboxamide was prepared according to the general method as outlined in Example 30 (step 8). Starting from 4-({[4-(2-Butynyloxy)phenyl]sulfonyl}methyl)-1-[(2,2,5-trimethyl-1,3-dioxan-5-yl)carbonyl]-4-piperidinecarboxylic acid (0.22 g, 0.433 mmol), 0.16 g of the desired product was isolated as white solid. Electrospray Mass Spec: 523.2 (M+H)$^+$

EXAMPLE 43

4-({[4-(2-Butynyloxy)phenyl]sulfonyl}methyl)-N-hydroxy-1-[3-hydroxy-2-(hydroxymethyl)-2-methylpropanoyl]-4-piperidinecarboxamide A mixture of 4-({[4-(2-Butynyloxy)phenyl]sulfonyl}methyl)-N-hydroxy-1-[(2,2,5-trimethyl-1,3-dioxan-5-yl)carbonyl]-4-piperidinecarboxamide (0.106 g, 0.2 mmol) and 2 mL of 1N HCl in 2 mL of THF was stirred at room temperature for 4 h. The reaction was diluted with EtOAc, washed with H$_2$O, saturated NaHCO$_3$, brine, dried over MgSO$_4$, filtered, and concentrated in vacuo. The residue was triturated with ether to provide 0.67 g (71%) of the desired product as an off white solid. Electrospray Mass Spec: 483.2 (M+H)$^+$

EXAMPLE 44

1-[Amino(imino)methyl]-4-({[4-(2-butynyloxy)phenyl]sulfonyl}methyl)-N-hydroxy-4-1]-4-({[4-(2-butynyloxy)phenyl]sulfonyl}methyl)-N-hydroxy-4-oxy)phenyl]sulfonyl}methyl)-N-hydroxy-4-piperidinecarboxamide Step 1

N,N'-t-Boc-protected thiourea

To a stirred solution of thiourea (0.57 g, 7.5 mmol) in 150 mL of THF under N$_2$ at 0° C. was added 60% NaH (1.35 g, 33.8 mmol) in mineral oil. After 5 minutes, the ice bath was removed and the reaction mixture was allowed to stir at room temperature for 10 minutes. The reaction mixture was cooled to 0° C. and 3.6 g (16.5 mmol) of di-tert-butyl dicarbonate was added. After 30 minutes, the ice bath was removed and the reaction was stirred for 2 h. The reaction was then quenched with saturated NaHCO$_3$ solution, poured into water and extracted with 3× EtOAc. The organics were washed with H$_2$O, brine, dried over MgSO$_4$, filtered, and concentrated in vacuo. The residue was triturated with hexane to provide 1.72 g (83%) of the desired product as a white solid.

Step 2 tert-Butyl4-[(tert-butoxyamino)carbonyl]-4-({[4-(2-yloxy)phenyl]sulfonyl}methyl)-1-piperidinecarboxylate tert-Butyl4-[(tert-butoxyamino)carbonyl]-4-({[4-(2-yloxy)phenyl]sulfonyl}methyl)-1-piperidinecarboxylate was prepared according to the general method as outlined in Example 30 (step 8). Starting from 4-(4-but-2-ynyloxy-benzenesulfonylmethyl)-piperidine-1,4-dicarboxylic acid mono-tert-butyl ester (2.53 g, 5.6 mmol) and O-tert-butylhydroxylamine hydrochloride (1.4 g, 11.2 mmol), 2.31 g (79%) of the desired product was isolated as a white solid. Electrospray Mass Spec: 523.2 (M+H)$^+$ Step 3

N-(tert-Butoxy)-4-({[4-(2-butynyloxy)phenyl]sulfonyl}methyl)-4-[4-(2-butynyloxy)phenyl]sulfonyl}methyl)-4-piperidinecarboxamide To a solution of tert-Butyl4-[(tert-butoxyamino)carbonyl]-4-({[4-(2-yloxy)phenyl]sulfonyl}methyl)-1-piperidinecarboxylate (3.0 g, 5.5 mmol) in 6 mL of CH$_2$Cl$_2$ was added of trimethylsilyltrifluoromethylsulfonate (1.1 ml, 6.05 mmol) followed by 0.7 mL of 2,6-lutidine. The reaction was stirred for 1 h and diluted with CH$_2$Cl$_2$. The organics were washed with H$_2$O, saturated NaHCO$_3$, brine, dried over MgSO$_4$, filtered, and concentrated in vacuo to provide 2.01 g (86%) of the desired product as an off white solid. Electrospray Mass Spec: 423.2 (M+H)$^+$ Step 4

[[4-[(tert-Butoxyamino)carbonyl]-4-[[[4-(2-[4-(2-butynyloxy)phenyl]sulfonyl}methyl)-4-piperidinecarboxamide butoxycarbonyl)amino]methylene]carbamic acid, tert-butyl ester To a mixture of N-(tert-Butoxy)-4-({[4-(2-butynyloxy)phenyl]sulfonyl}methyl)-4-[4-(2-butynyloxy)phenyl]sulfonyl}methyl)-4-piperidinecarboxamide (0.127 g, 0.3 mmol), the di-t-boc-protected thiourea (obtained from step 1) (0.091 g, 0.33 mmol) and triethylamine (0.092 ml) in 3 mL of DMF was added mercury(II) chloride (0.09 g, 0.33 mmol) and stirred for 1 h at 0° C. The reaction was diluted with EtOAc and filtered through a pad of celite. The organics were washed with $H_2O$, brine, dried over $MgSO_4$, filtered, and concentrated in vacuo. The residue was triturated with hexanes to provide the desired product as a white solid. Electrospray Mass Spec: 665.5 $(M+H)^+$ Step 5

1-[Amino(imino)methyl]-4-({[4-(2-butynyloxy)phenyl]sulfonyl}methyl)-N-hydroxy-4-1]-4-({[4-(2-butynyloxy)phenyl]sulfonyl}methyl)-N-hydroxy-4-oxy)phenyl]sulfonyl}methyl)-N-hydroxy-4-piperidinecarboxamide A mixture of [[4-[(tert-Butoxyamino)carbonyl]-4-[[[4-(2-[4-(2-butynyloxy)phenyl]sulfonyl}methyl)-4-piperidinecarboxamide butoxycarbonyl)amino]methylene] carbamic acid, tert-butyl ester (0.135 g, 0.2 mmol) and 3 mL of trifluoroacetic acid in 2 mL of $CH_2Cl_2$ was heated at 60° C. for 24 h. The reaction was concentrated in vacuo and was prep HPLC to provide 0.032 g (31%) of the desired product as a beige solid. Electrospray Mass Spec: 409.3 $(M+H)^+$

EXAMPLE 45

4-({[4-(2-Butynyloxy)phenyl]sulfonyl}methyl)-N-hydroxy-1-(4-hydroxy-2-butynyl)-henyl]sulfonyl}methyl)-N-hydroxy-1-(4-hydroxy-2-butynyl)-4-piperidinecarboxamide Step 1

Ethyl-4-({[4-(2-butynyloxy)phenyl]sulfonyl}methyl)-1-(4-{[(3-chloroanilino)carbonyl]oxy}-2-butynyl)-4-piperidinecarboxylate Ethyl-4-({[4-(2-butynyloxy)phenyl]sulfonyl}methyl)-1-(4-{[(3 chloroanilino)carbonyl]oxy}-2-butynyl)-4-piperidinecarboxylate was prepared according to the general method as outlined in Example 37 (step 1). Starting from 4-[[[4-(2-Butynyloxy)phenyl]sulfonyl]methyl]-4-piperidinecarboxylic acid ethyl ester (0.291 g,0.7 mmol) and 4-chloro-2-butynyl-(3-chlorophenyl)carbamate (0.19 g, 0.735), 0.27 g (64%) of the desired product was isolated as pale yellow oil. Electrospray Mass Spec: 601.3 $(M+H)^+$ Step 2

Ethyl-4-({[4-(2-butynyloxy)phenyl]sulfonyl}methyl)-1-(4-hydroxy-2-butynyl)-4-nyloxy)phenyl]sulfonyl}methyl)-1-(4-hydroxy-2-butynyl)-4-piperidine carboxylate A solution of ethyl-4-({[4-(2-butynyloxy)phenyl]sulfonyl}methyl)-1-(4-{[(3-chloroanilino)carbonyl]oxy}-2-butynyl)-4-piperidinecarboxylate (from step 1) 0.22 g, 0.366 mmol) and lithiumhydroxide hydrate (0.019 g, 0.44 mmol) in 4 mL MeOH was heated to reflux for 3 h. The reaction was concentrated, diluted with $H_2O$, acidified to pH 3 and extracted with $CH_2Cl_2$. The organics were washed with $H_2O$, brine, dried over $MgSO_4$, filtered, and concentrated in vacuo. The residue was chromatographed on silica gel eluting with 3% $MeOH/CH_2Cl_2$ to provide 0.12 g (73%) of the desired product as an yellow oil. Electrospray Mass Spec: 448.3 $(M+H)^+$ Step 3

4-({[4-(2-Butynyloxy)phenyl]sulfonyl}methyl)-1-(4-hydroxy-2-butynyl)-4-nyl]sulfonyl}methyl)-1-(4-hydroxy-2-butynyl)-4-piperidinecarboxylic acid 4-({[4-(2-Butynyloxy)phenyl]sulfonyl}methyl)-1-(4-hydroxy-2-butynyl)-4 nyl]sulfonyl}methyl)-1-(4-hydroxy-2-butynyl)-4-piperidinecarboxylic acid was prepared according to the general method as outlined in Example 30 (step 7). Starting from ethyl-4-({[4-(2-butynyloxy)phenyl]sulfonyl}methyl)-1-(4-hydroxy-2-butynyl)-4-piperidinecarboxylate (0.115 g, 0.257 mmol), 0.08 g (74%) of the desired product was isolated as white solid. Electrospray Mass Spec: 420.4 $(M+H)^+$ Step 4

4-({[4-(2-Butynyloxy)phenyl]sulfonyl}methyl)-N-hydroxy-1-(4-hydroxy-2-butynyl)-henyl]sulfonyl}methyl)-N-hydroxy-1-(4-hydroxy-2-butynyl)-4-piperidinecarboxamide 4-({[4-(2-Butynyloxy)phenyl]sulfonyl}methyl)-N-hydroxy-1-(4-hydroxy-2-butynyl)-henyl]sulfonyl}methyl)-N-hydroxy-1-(4-hydroxy-2-butynyl)-4-piperidinecarboxamide was prepared according to the general method as outlined in Example 30 (step 8). Starting from 4-({[4-(2-Butynyloxy)phenyl]sulfonyl}methyl)-1-(4-hydroxy-2-butynyl)-4-nyl]sulfonyl}methyl)-1-(4-hydroxy-2-butynyl)-4-piperidinecarboxylic acid (0.073 g, 0.174 mmol), 0.026 g (34%) of the desired product was isolated as white solid. Electrospray Mass Spec: 435.3 $(M+H)^+$ Methods for the solution phase synthesis of the compounds of the present invention is as shown in the following scheme.

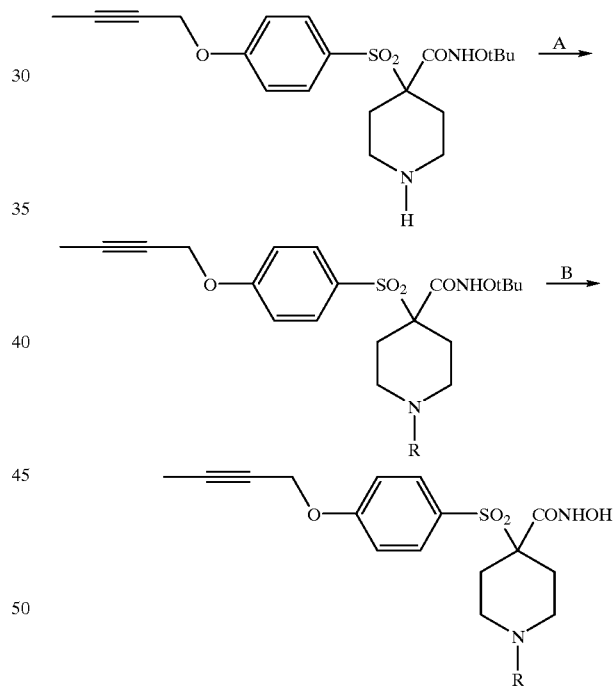

EXAMPLE 46

4-({[4-(But-2-ynyloxy)phenyl[sulfonyl}methyl)-1-ethyl-N-hydroxypiperidine-4-carboxamide trifluoroacetic acid salt Step A A solution of N-(tert-butoxy)-4-({[4-2-butynyloxy)phenyl]sulfonyl}methyl)-4-[4-(2-butynyloxy)phenyl]sulfonyl}methyl-4-piperidinecarboxyamide (0.097 g, 0.23 mmol), ethyl iodide (0.019 mL ,0.24 mmol)and triethylamine (0.096 mL, 0.69 mmol) in 2 mL of CH2Cl2 was shaken at room temperature for 18 h and then concentrated in vacuo.

Step B

A solution of the residue from Step A in 1 mL of CH2Cl2 and 1 mL of trifluoroacetic acid was heated at 50° C. for 2 h and then concentrated in vacuo to provide the desired product.

The following hydroxamic acids were synthesized according to the procedures of 4-({[4-(But-2-ynyloxy) phenyl]sulfonyl}methyl)-1-ethyl-N-hydroxypiperidine-4-carboxamide triflouroacetic acid salt using the appropriate reagents.

EXAMPLE 47

Reagent—0.029 mL (0.24 mmol) of 2-chloro-5-(chloromethyl)thiophene4-({[4-(But-2-ynyloxy) phenyl]sulfonyl}methyl)-1-[(5-chlorothien-2-yl) methyl]-N-hydroxypiperidine-4-carboxamide triflouroacetic acid salt

EXAMPLE 48

Reagent—0.0496 g (0.24 mmol) of 4-picolyl chloride hydrochloride 4-({[4-(But-2-ynyloxy) phenyl]sulfonyl}methyl)-N-hydroxy-1-(pyridin-4-ylmethyl)piperidine-4-carboxamide triflouroacetic acid salt

EXAMPLE 49

4-({[4-(But-2-ynyloxy)phenyl]sulfonyl}methyl)-N-hydroxy-1-(pyridin-3 ylcarbonyl)piperidine-4-carboxamide triflouroacetic acid salt Step A A solution of N-(tert-butoxy)-4-({[4-92-butynyloxy) phenyl]sulfonyl}methyl)-4-[4-(2-butynyloxy)phenyl] sulfonyl}methyl-4-piperidine carboxyamide (0.097 g, 0.23 mmol), triethylamine (0.064 mL, 0.64 mmol), nicotinoyl chloride hydrochloride (0.061 g ,0.34 mmol), and 4-dimethylaminopyridine (0.002 g) in 2 mL of CH2Cl2 was shaken at room temperature for 18 h and then concentrated in vacuo.

Step B

Same as Step B of Example 46.

The following hydroxamic acids were synthesized according to the procedures of 4 ({[4-(But-2-ynyloxy) phenyl]sulfonyl}methyl)-N-hydroxy-1-(pyridin-3-ylcarbonyl)piperidine-4-carboxamide triflouroacetic acid salt using the appropriate reagents.

EXAMPLE 50

Reagent—0.04 mL (0.276 mmol) of benzoyl chloride 1-Benzoyl-4-({[4-(but-2-ynyloxy)phenyl] sulfonyl}methyl)-N-hydroxypiperidine-4-carboxamide

EXAMPLE 51

Reagent—0.037 mL (0.276 mmol) of 2-thiophenecarbonyl chloride 4-({[4-(But-2-ynyloxy) phenyl]sulfonyl}methyl)-N-hydroxy-1-(thien-2-ylcarbonyl) piperidine-4-carboxamide

EXAMPLE 52

4-({[4-(But-2-ynyloxy)phenyl]sulfonyl}methyl)-N-1-ethyl-N-4-hydroxypiperidine-1,4-dicarboxamide Step A A solutiion of N-(tert-butoxy)-4-({[4-92-butynyloxy) phenyl]sulfonyl}methyl)-4-[4-(2-butynyloxy)phenyl] sulfonyl}methyl-4-piperidine carboxyamide (0.097 g, 0.23 mmol), triethylamine (0.064 mL, 0.64 mmol) and ethyl isocyanate (0.02 mL ,0.253 mmol) in 2 mL of CH2Cl2 was shaken at room temperature for 18 h and then concentrated in vacuo.

Step B

Same as Step B of Example 46.

The following hydroxamic acids were synthesized according to the procedures of Example 52 using the appropriate reagents.

EXAMPLE 53

Reagent—0.275 mL (0.253 mmol) of phenylisocyanate 4-({[4-(But-2-ynyloxy)phenyl] sulfonyl}methyl)-N-4-hydroxy-N-1-phenylpiperidine-1,4-dicarboxamide

EXAMPLE 54

Reagent—0.32 mL (0.253 mmol) of diethylcarbamyl chloride 4-({[4-(But-2-ynyloxy) phenyl]sulfonyl}methyl)-N-1-,N-1-diethyl-N-4-hydroxypiperidine-1,4-dicarboxamide

EXAMPLE 55

Reagent—0.0295 mL (0.253 mmol) of morpholine carbonyl chloride 4-({[4-(But-2-ynyloxy)phenyl] sulfonyl}methyl)-N-hydroxy-1-(morpholin-4-ylcarbonyl)piperidine-4-carboxamide

EXAMPLE 56

Reagent—0.043 g (0.253 mmol) of methylphenylcarbamoyl chloride 4-({[4-(But-2-ynyloxy)phenyl]sulfonyl}methyl)-N-4-hydroxy-N-1-methyl-N-1-phenylpiperidine-1,4-dicarboxamide

EXAMPLE 57

Octyl-4-({[4-(but-2-ynyloxy)phenyl] sulfonyl}methyl)-4-[(hydroxyamino)carbonyl] piperidine-1-carboxylate Step A A solution of 0.097 g (0.23 mmol) of N-(tert-butoxy)-4-({[4-92-butynyloxy)phenyl]sulfonyl}methyl)-4-[4-(2-butynyloxy)phenyl]sulfonyl}methyl-4-piperidinecarboxyamide (0.097 g, 0.23 mmol), octyl chloroformate (0.0495 ml, 0.253 mmol) and diisopropyl-ethylamine (0.08 ml, 0.46 mmol) in 2 mL of CH2Cl2 was shaken at room temperature for 18 h and then concentrated in vacuo.

Step B

Same as Step B of Example 46.

The following hydroxamic acids were synthesized according to the procedures of Example 57 using the appropriate reagents.

EXAMPLE 58

Reagent—0.038 mL (0.253 mmol) of 4-methoxyphenyl chloroformate 4-Methoxyphenyl4-({[4-(but-2-ynyloxy)phenyl]sulfonyl}methyl)-4-[(hydroxyamino)carbonyl]piperidine-1-carboxylate

EXAMPLE 59

Reagent—0.0323 mL (0.253 mmol) of benzenesulfonyl chloride 4-({[4-(But-2-ynyloxy)phenyl]sulfonyl}methyl)-N-hydroxy-1-(phenylsulfonyl)piperidine-4-carboxamide

EXAMPLE 60

Reagent—0.0457 g (0.253 mmol) of 1-methylimidazole-4-sulfonyl chloride 4-({[4-(But-2-ynyloxy)phenyl]sulfonyl}methyl)-N-hydroxy-1-[(1-methyl-1H-imidazol-4-yl)sulfonyl]piperidine-4-carboxamide

EXAMPLE 61

1-[2-(Benzylamino)acetyl]-4-({[4-(but-2-ynyloxy)phenyl]sulfonyl}methyl)-N-hydroxypiperidine-4-carboxamide Step A A solution of N-(tert-butoxy)-4-({[4-2-butynyloxy)phenyl]sulfonyl}methyl)-4-[4-(2-butynyloxy)phenyl]sulfonyl}methyl-4-piperidine carboxyamide (0.097 g, 0.23 mmol), triethylamine (0.064 mL, 0.64 mmol), chloroacetyl chloride (0.064 ml, 0.64 mmol), and 4-dimethylaminopyridine (0.002 g) in 2 mL of CH2Cl2 was shaken at room temperature for 18 h. The solution was then treated with benzyl amine (0.075 mL, 0.69 mmol) and was shaken for 18 h and then concentrated in vacuo.

Step B

Same as Step B of Example 46.

The following hydroxamic acids were synthesized according to the procedures Example 61 using the appropriate amine reagents.

EXAMPLE 62

Reagent—0.060 mL (0.69 mmol) of morpholine 4-({[4-(But-2-ynyloxy)phenyl]sulfonyl}methyl)-N-hydroxy-1-(2-morpholin-4-ylacetyl)piperidine-4-carboxamide

EXAMPLE 63

Reagent—0.076 mL (0.69 mmol) of N-methylpiperazine 4-({[4-(But-2-ynyloxy)phenyl]sulfonyl}methyl)-N-hydroxy-1-[2-(4-methylpiperazin-1-yl)acetyl]piperidine-4-carboxamide

| Eample # | HPLC retention time (min.)[1] | MS[2] (M + H)+ |
|---|---|---|
| 46 | 1.85 | 395 |
| 47 | 2.20 | 498 |
| 48 | 1.71 | 458 |
| 49 | 2.11 | 472 |
| 52 | 2.30 | 438 |
| 53 | 2.85 | 486 |
| 57 | 3.80 | 523 |

-continued

| Eample # | HPLC retention time (min.)[1] | MS[2] (M + H)+ |
|---|---|---|
| 58 | 2.98 | 517 |
| 54 | 2.87 | 466 |
| 55 | 2.33 | 480 |
| 56 | 2.84 | 500 |
| 59 | 2.92 | 507 |
| 60 | 2.40 | 511 |
| 50 | 2.67 | 471 |
| 51 | 2.64 | 477 |
| 61 | 2.14 | 514 |
| 62 | 1.86 | 494 |
| 63 | 1.84 | 507 |

[1]LC conditions: Hewlett Packard 1100; YMC ODS-A 4.6 mm × 50 mm 5 u column at 23° C.; 10 uL injection; Solvent A: 0.05% TFA/water; Solvent B: 0.05% TFA/acetonitrile; Gradient: Time 0: 98% A; 1 min: 98% A; 7 min: 10% A, 8 min: 98% A; Post time 1 mm. Flow rate 2.5 mL/min; Detection: 220 and 254 nm DAD
[2]Mass Spec conditions: API-electrospray

EXAMPLE 64

1-Acetyl-4-(4-but-2-ynyloxybenzenesulfonyl)piperidine-4-carboxylic acid hydroxamide Step 1

4-But-2-ynyloxybenzenesulfonyl fluoride

To a solution of 4-but-2-ynyloxybenzenesulfonyl chloride (prepared from Example 30, step 4) (2.0 g, 8.18 mmol) in acetonitrle (10 ml) was added KF-CaF$_2$ (2.85 g, 16.3 mmol) and the resulting mixture was stirred for 4 hours at room temperature. The reaction mixture was filtered and the filterate was concentrated. The crude product was dissolved in EtOAc and washed with water. The organic layer was dried over anhydrous Na$_2$SO$_4$ and the solvent was removed to obtain 1.5 g (80%) of the product as solid.

Step 2

4-(4-But-2-ynyloxybenzenesulfonyl)-piperidine-1,4-dicarboxylic acid tert-butyl ester methyl ester To a solution of diisopropylamine (1.58 mL, 11.3 mmol) in THF (25 mL) at 0° C. was added 2.5M n-BuLi(4.68 mL, 11.7 mmol) and the resulting mixture was stirred for 15 min at that temperature. The reaction mixture was cooled to –78° C. and a solution of 1-(tert-butyl)-4-methyl 1,4-piperidinecarboxylate (prepared from example 30, step 1) (2.67 g, 11.0 mmol) in THF (40 mL) was added. The resulting mixture was stirred for 1 h and a solution of 4-but-2-ynyloxy benzenesulfonyl fluoride (2.5 g, 11.0 mmol) in THF (25 mL) was added into it. After stirring for 4 h at rt, the reaction was quenched with satd. aqueous NH$_4$Cl solution and extracted with EtOAc, dried over anhydrous Na$_2$SO$_4$. The crude product was purified by silica gel chromatography to obtain 2.6 g(53%) of the product as a solid; $^1$H NMR(300 MHz, CDCl$_3$) δ1.44(s, 9H), 1.87(m, 3H), 1.98(m, 2H), 2.32(m, 2H), 2.62(m, 2H), 3.74(s, 3H), 4.17(m, 2H), 4.74(m, 2H), 7.09(d, 2H, J=7.2 Hz), 7.71(d, 2H, J=7.2 Hz).

Step 3

4-(4-but-2-ynyloxy-benzenesulfonyl)-piperidine-4-carboxylic acid methyl ester

To a solution of product from step 2 (500 mg, 1.11 mmol) in methylene chloride (10 ml) was added 4M HCl (2 ml) and the resulting mixture was stirred for 2 hours at room temperature. The solid was filtered, washed with ether to obtain 410 mg(95%) of the product as a solid. $^1$H NMR(300 MHz, CDCl$_3$): δ1.86(m, 3H), 2.52(m, 4H), 2.89(m, 2H), 3.52(m, 2H), 3.74(s, 3H), 4.74(m, 2H), 7.10(d, 2H, J=8.7 Hz), 7.69(d, 2H, J=8.7 Hz).
Step 4

1-Acetyl-4-(4-but-2-ynyloxybenzenesulfonyl) piperidine-4-carboxylic acid methyl ester To a solution of product from step 3 (105 mg, 0.23 mmol) in methylene chloride (1 ml) was added triethylamine (93 mg, 0.92 mmol), acetyl chloride (18 mg, 0.23 mmol) followed by a catalytic amount of dimethylaminopyridine. The resulting mixture was stirred for 8 hours at room temperature, quenched with water and extracted with methylene chloride. The organic layer was dried over anhydrous sodium sulfate and concentrated to give 75 mg (80%) of the product as a solid.
Step 5

1-Acetyl-4-(4-but-2-ynyloxybenzenesulfonyl) piperidine-4-carboxylic acid

A solution of the ester, from step 4 (240 mg, 0.61 mmol)) and lithium hydroxide (18 mg, 0.75 mmol)) in tetrahydrofuran/methano/water (3:3:2) mixture was stirred at room temperature for 15 hours. The mixture was concentrated, acidified to pH 3–5 with 1N aqueous hydrochloric acid, and extracted with ethyl acetate. The organic layer was washed with brine and dried over anhydrous sodium sulfate. Removal of the solvent under vacuuo gave the acid. Yield : 200 mg, (87%). $^1$H NMR(300 MHz, acetone-d$_6$): δ1.84(t, 3H, J=2.8 Hz), 1.90–2.05(m, 2H), 2.06(s, 3H), 2.25–2.51(m, 3H), 3.06(m, 1H), 4.04(m, 1H), 4.63(m, 1H), 4.86(q, 1H, J=2.0).
Step 6

1-Acetyl-4-(4-but-2-ynyloxybenzenesulfonyl) piperidine-4-carboxylic acid hydroxamide To a solution of 1-acetyl-4-(4-but-2-ynyloxybenzenesulfonyl)piperidine-4-carboxylic acid (180 mg, 0.48 mmol) in dimethylformamide was added hydroxybenzotriazol (77 mg, 0.57 mmol) followed by 1-(3-dimethylaminopropyl)-3-ethylcarbodiimide hydrochloride (127 mg, 0.66) and N-methylmorpholine (0.078 ml, 0.71 mmol). The resulting mixture was stirred for 1 h at room temperature when 50% aqueous hydroxylamine solution (0.145 ml, 2.37 mmol) was added and the mixture was stirred for 15 h at that temperature. The solvent was removed in vacuo and ethyl acetate/water was added to the crude product. The organic layer was separated and washed successively with 1N aqueous hydrochloric acid, water, saturated aqueous sodium bicarbonate, and water. The organic layer was dried over anhydrous sodium sulfate and the solvent was removed in vacuo to obtain 100 mg (53%) of the product as a solid. $^1$H NMR(300 MHz, CDCl$_3$): δ1.64(m, 1H), 1.85(m, 3H), 1.99(s, 3H), 2.31(m, 4H), 2.83(m, 1H), 3.88(m, 1H), 4.41(m, 1H), 4.88(m, 2H), 7.16(d, 2H, J=9.0 Hz), 7.66(d, 2H, J=9.0 Hz), 9.20(m, 1H), 11.00(m, 1H); MS-ES: m/z 395.2 (M+H)$^+$.

EXAMPLE 65

1-Benzoyl-4-(4-but-2-ynyloxybenzenesulfonyl) piperidine-4-carboxylic acid hydroxamide
Step 1

1-Benzoyl-4-(4-but-2-ynyloxybenzenesulfonyl) piperidine-4-carboxylic acid methyl ester To a solution of 4-(4-but-2-ynyloxy-benzenesulfonyl)-piperidine-4-carboxylic acid methyl ester, (400 mg, 1.03 mmol) in chloroform (10 ml) was added triethylamine (416 mg, 4.12 mmol), benzoyl chloride(144 μl, 1.24 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 375 mg (80%) of the product as a solid. MS-ES: m/z 456.1 (M+H)$^+$.
Step 2

1-Benzoyl-4-(4-but-2-ynyloxybenzenesulfonyl) piperidine-4-carboxylic acid

1-Benzoyl-4-(4-but-2-ynyloxybenzenesulfonyl) piperidine-4-carboxylic acid was prepared, starting from 1-benzoyl-4-(4-but-2-ynyloxybenzenesulfonyl)piperidine-4-carboxylic acid methyl ester (300 mg, 0.66 mmol) and lithium hydroxide (18 mg, 0.75 mmol). The resulting reaction mixture was worked up as outlined in Example 64, (step 5). Yield: 250 mg (86%) of the acid. HR-MS: m/z Calculated for C$_{23}$H$_{23}$NO$_6$S 442.1319; Found 442.1317.
Step 3

1-Benzoyl-4-(4-but-2-ynyloxybenzenesulfonyl) piperidine-4-carboxylic acid hydroxamide The general procedure for step 6 (Example 64) was followed using 1-benzoyl-4-(4-but-2-ynyloxybenzenesulfonyl)piperidine-4-carboxylic acid (100 mg, 0.23 mmol) in dimethylformamide (2 ml), 1-hydroxybenzotriazole (36 mg, 0.27 mmol), 1-[3-(dimethylamino)propyl]-3-ethylcarbodiimide hydrochloride (62 mg, 0.32 mmol), N-methylmorpholine (0.038 ml, 0.35 mmol), and hydroxylamine (0.083 ml, 1.15 mmol) to obtain 40 mg (38%) of the product as a solid. MS-ES: m/z 457.2 (M+H)$^+$.

EXAMPLE 66

1-(4-Methoxybenzoyl)-4-(4-but-2-ynyloxybenzenesulfonyl)piperidine-4-carboxylic acid hydroxamide
Step 1

1-(4-Methoxybenzoyl)-4-(4-but-2-ynyloxybenzenesulfonyl)piperidine-4-carboxylic acid methyl ester To a solution of 4-(4-but-2-ynyloxy-benzenesulfonyl)-piperidine-4-carboxylic acid methyl ester (260 mg, 0.77 mmol) in chloroform (7 ml) was added triethylamine (311 mg, 3.08 mmol), 4-methoxybenzoyl chloride (158 mg, 0.92 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 280 mg (75%) of the product as a solid. HR-MS: m/z Calculated for C$_{25}$H$_{27}$NO$_7$S 486.1581; Found 486.1576.
Step 2

1-(4-Methoxybenzoyl)-4-(4-but-2-ynyloxybenzenesulfonyl)piperidine-4-carboxylic acid 1-(4-Methoxybenzoyl)-4-(4-but-2-ynyloxybenzenesulfonyl)piperidine-4-carboxylic acid was prepared following the procedure of Example 64 (step 5). Starting from 1-(4-methoxybenzoyl)-4-(4-but-2-ynyloxybenzenesulfonyl)piperidine-4-carboxylic acid methyl ester 250 mg, 0.52 mmol) in 4 ml of tetrahydrofuran:methanol (1:1) and 1N sodium hydroxide (1.03 ml, 1.03 mmol) 150 mg of (62%) of the acid was isolated. HR-MS: m/z Calculated for $C_{24}H_{25}NO_7S$ 472.1425; Found 472.1426.

Step 3

1-(4-Methoxybenzoyl)-4-(4-but-2-ynyloxybenzenesulfonyl)piperidine-4-carboxylic acid hydroxamide 1-(4-Methoxybenzoyl)-4-(4-but-2-ynyloxybenzenesulfonyl)piperidine-4-carboxylic acid hydroxamide was prepared following the procedure Example 64 (step 6). Starting from 1-(4-methoxybenzoyl)-4-(4-but-2-ynyloxybenzenesulfonyl)piperidine-4-carboxylic acid (90 mg, 0.19 mmol) in dimethylformamide (2 ml), 1-hydroxybenzotriazole (31 mg, 0.23 mmol), 1-[3-(dimethylamino)propyl]-3-ethylcarbodiimide hydrochloride (51 mg, 0.27 mmol), N-methylmorpholine (0.031 ml, 0.28 mmol), and hydroxylamine (0.068 ml, 0.95 mmol), 70 mg (76%) of the product was isolated as solid. HR-MS: m/z Calculated for $C_{24}H_{26}N_2O_7S$ 487.1534; Found 487.1531.

EXAMPLE 67

4-(4-But-2-ynyloxybenzenesulfonyl)-N-hydroxy-1-(pyrrolidine-1-carbonyl)-4-piperidinecarboxamide Step 1

4-(4-but-2-ynyloxybenzenesulfonyl)-1-(pyrrolidine-1-carbonyl)-piperidine-4-carboxylic acid methyl ester To a solution of 4-(4-but-2-ynyloxy-benzenesulfonyl)-piperidine-4-carboxylic acid methyl ester (400 mg, 1.03 mmol) in chloroform (10 ml) was added triethylamine (208 mg, 2.06 mmol), pyrrolidinecarbonyl chloride (206 mg, 1.54 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 400 mg (87%) of the product as a solid; MS-ES: m/z 449.3 (M+H)$^+$.

Step 2

4-(4-but-2-ynyloxybenzenesulfonyl)-1-(pyrrolidine-1-carbonyl)-piperidine-4-carboxylic acid 4-(4-But-2-ynyloxybenzenesulfonyl)-1-(pyrrolidine-1-carbonyl)-piperidine-4-carboxylic acid was prepared following the procedure of Example 64 (step 5). Starting from 4-(4-but-2-ynyloxybenzenesulfonyl)-1-(pyrrolidine-1-carbonyl)-piperidine-4-carboxylic acid methyl ester (250 mg, 0.52 mmol) in 4 ml of tetrahydrofuran:methanol (1:1) and 1N sodium hydroxide (1.03 ml, 1.03 mmol), 150 mg of (62%) of the acid was isolated. HR-MS: m/z Calculated for $C_{24}H_{25}NO_7S$ 472.1425; Found 472.1426.

Step 3

4-(4-But-2-ynyloxybenzenesulfonyl)-N-hydroxy-1-(pyrrolidine-1-carbonyl)-4-piperidinecarboxamide 4-(4-But-2-ynyloxybenzenesulfonyl)-N-hydroxy-1-(pyrrolidine-1-carbonyl)-4-piperidinecarboxamide was prepared following the procedure Example 64 (step 6). Starting from 4-(4-But-2-ynyloxybenzenesulfonyl)-N-hydroxy-1-(pyrrolidine-1-carbonyl)-4-piperidinecarboxalic acid (255 mg, 0.23 mmol) in dimethylformamide (6 ml), 1-hydroxybenzotriazole (96 mg, 0.71 mmol), 1-[3-(dimethylamino)propyl]-3-ethylcarbodiimide hydrochloride (157 mg, 0.82 mmol), N-methylmorpholine (0.099 ml, 0.84 mmol), and hydroxylamine (0.181 ml, 2.8 mmol), 150 mg (60%) of the product was isolated as a solid. HR-MS: m/z Calculated for $C_{21}H_{27}N_3O_6S$ 450.1693; Found 450.1692.

EXAMPLE 68

Ethyl 4-(4-but-2-ynyloxybenzenesulfonyl)-4-[(hydroxyamino)carbonyl]-1-piperidinecarboxylate Step 1

1-Ethyl 4-methyl 4-(4-but-2-ynyloxybenzenesulfonyl)-1,4-piperidinedicarboxylate To a solution of 4-(4-but-2-ynyloxy-benzenesulfonyl)-piperidine-4-carboxylic acid methyl ester (400 mg, 1.03 mmol) in chloroform (10 ml) was added sodium bicarbonate (865 mg, 10.3 mmol), ethylchloroformate (0.147 ml, 1.54 mmol). The resulting mixture was stirred for 15 hours at room temperature, quenched with water and extracted with methylene chloride. The organic layer was dried over anhydrous sodium sulfate and concentrated to give 425 mg (98%) of the product as a solid. MS-ES: m/z 424.4 (M+H)$^+$.

Step 2

1-(Ethylcarbonyl)-4-(4-but-2-ynyloxybenzenesulfonyl)-1-piperidinecarboxylic acid 1-(Ethylcarbonyl)-4-(4-but-2-ynyloxybenzenesulfonyl)-1-piperidinecarboxylic acid was prepared following the procedure of Example 64 (step 5). Starting from 1-Ethyl 4-methyl 4-(4-but-2-ynyloxybenzenesulfonyl)-1,4-piperidinedicarboxylate (400 mg, 0.95 mmol) in 8 ml of tetrahydrofuran:methanol; water (1:1:0.5) and lithium hydroxide (50 mg, 2.04 mmol), 340 mg of (88%) of the acid was isolated. HR-MS: m/z Calculated for $C_{19}H_{23}NO_7S$ 408.1122; Found 408.1126.

Step 3

Ethyl 4-(4-but-2-ynyloxybenzenesulfonyl)-4-[(hydroxyamino)carbonyl]-1-piperidinecarboxylate Ethyl 4-(4-but-2-ynyloxybenzenesulfonyl)-4-[(hydroxyamino)carbonyl]-1-piperidinecarboxylate was prepared following the procedure Example 64 (step 6). Starting from 1-(Ethylcarbonyl)-4-(4-but-2-ynyloxybenzenesulfonyl)-1-piperidinecarboxylic acid (225 mg, 0.55 mmol) in dimethylformamide (6 ml), 1-hydroxybenzotriazole(89 mg, 0.66 mmol), 1-[3-(dimethylamino)propyl]-3-ethylcarbodiimide hydrochloride (148 mg, 0.77 mmol), N-methylmorpholine (0.091 ml, 0.86 mmol), and hydroxylamine (0.168 ml, 2.75 mmol), 150 mg (64%) of the product was isolated as a solid. HR-MS: m/z Calculated for $C_{19}H_{24}N_2O_7S$ 425.1377; Found 425.1375.

EXAMPLE 69

4-(4-But-2-ynyloxybenzenesulfonyl)-N-hydroxy-1-[(trifluoromethyl)sulfonyl]-4-piperidinecarboxamide Step 1

Methyl 4-(4-but-2-ynyloxybenzenesulfonyl)-1-[(trifluoromethyl)sulfonyl]-4-piperidinecarboxylate To a solution of 4-(4-but-2-ynyloxy-benzenesulfonyl)-piperidine-4-carboxylic acid methyl ester (350 mg, 0.90 mmol) in chloroform (10 ml) was added triethylamine (182 mg, 1.81 mmol), trifluoromethanesulfonyl chloride (0.125 ml, 1.17 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 245 mg (56%) of the product as a solid. HR-MS: m/z Calculated for $C_{18}H_{20}F_3NO_7S_2$ 484.0706; Found 484.0700.
Step 2

4-(4-but-2-ynyloxybenzenesulfonyl)-1-[(trifluoromethyl) sulfonyl]-4-piperidinecarboxylic acid 4-(4-but-2-ynyloxybenzenesulfonyl)-1-[(trifluoromethyl) sulfonyl]-4-piperidinecarboxylic acid was prepared following the procedure of Example 64 (step 5). Starting from Methyl 4-(4-but-2-ynyloxybenzenesulfonyl)-1-[(trifluoromethyl) sulfonyl]-4-piperidinecarboxylate (225 mg, 0.47 mmol) in 8 ml of tetrahydrofuran:methanol; water (1:1:0.5) and lithium hydroxide (24 mg, 0.98 mmol), 175 mg of (80%) of the acid was isolated. MS-ES: m/z 468.1 (M–H)⁻.
Step 3

4-(4-but-2-ynyloxybenzenesulfonyl)-N-hydroxy-1-[(trifluoromethyl)sulfonyl]-4-piperidinecarboxamide 4-(4-but-2-ynyloxy benzenesulfonyl)-N-hydroxy-1-[(trifluoromethyl)sulfonyl]-4-piperidinecarboxamide was prepared following the procedure Example 64 (step 6). Starting from 4-(4-but-2-ynyloxybenzenesulfonyl)-1-[(trifluoromethyl)sulfonyl]-4-piperidinecarboxylic acid (145 mg, 0.31 mmol) in dimethylformamide (3 ml), 1-hydroxybenzotriazole (50 mg, 0.37 mmol), 1-[3-(dimethylamino)propyl]-3-ethylcarbodiimide hydrochloride (83 mg, 0.47 mmol), N-methylmorpholine (0.051 ml, 0.47 mmol), and hydroxylamine (0.095 ml, 1.55 mmol), 90 mg (60%) of the product was isolated as a solid. HR-MS: m/z Calculated for $C_{17}H_{19}F_3N_2O_7S_2$ 485.0659; Found 485.0666.

EXAMPLE 70

4-(4-But-2-ynyloxybenzenesulfonyl)-N-hydroxy-1-(3-pyridinylcarbonyl)-4-piperidinecarboxamide
Step 1

Methyl 4-(4-but-2-ynyloxybenzenesulfonyl)-1-(3-pyridinylcarbonyl)-4-piperidinecarboxylate To a solution of 4-(4-but-2-ynyloxy-benzenesulfonyl)-piperidine-4-carboxylic acid methyl ester (500 mg, 1.29 mmol) in methylene chloride (10 ml) was added triethylamine (443 mg, 4.39 mmol), nicotinyl chloride (276 ml, 1.55 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 460 mg (78%) of the product as a solid. HR-MS: m/z Calculated for $C_{23}H_{24}N_2O_6S$ 457.1428; Found 457.1428.
Step 2

4-(4-But-2-ynyloxybenzenesulfonyl)-1-(3-pyridinylcarbonyl)-4-piperidinecarboxylic acid 4-(4-But-2-ynyloxybenzenesulfonyl)-1-(3-pyridinylcarbonyl)-4-piperidine carboxylic acid was prepared following the procedure of Example 64 (step 5). Starting from Methyl 4-(4-but-2-ynyloxybenzenesulfonyl)-1-(3-pyridinylcarbonyl)-4-piperidinecarboxylate (430 mg, 0.94 mmol) in 8 ml of tetrahydrofuran:methanol (1:1), and 1N sodium hydroxide (1.89 ml, 1.89 mmol) to obtain 235 mg (57%) of the acid. HR-MS: m/z Calculated for $C_{22}H_{22}N_2O_6S$ 443.1271; Found 443.1270.
Step 3

4-(4-But-2-ynyloxybenzenesulfonyl)-N-hydroxy-1-(3-pyridinylcarbonyl)-4-piperidinecarboxamide was prepared following the procedure Example 64 (step 6). Starting from 4-(4-But-2-ynyloxybenzenesulfonyl)-1-(3-pyridinylcarbonyl)-4-piperidinecarboxylic acid (195 mg, 0.44 mmol) in dimethylformamide (4 ml), 1-hydroxybenzotriazole (72 mg, 0.53 mmol), 1-[3-(dimethylamino)propyl]-3-ethylcarbodiimide hydrochloride (119 mg, 0.62 mmol), N-methylmorpholine (0.072 ml, 0.66 mmol), and hydroxylamine (0.135 ml, 2.2 mmol), 65 mg (32%) of the product was isolated as a solid. HR-MS: m/z Calculated for $C_{22}H_{23}N_3O_6S$ 458.1380; Found 458.1373.

EXAMPLE 71

4-(4-but-2-ynyloxybenzenesulfonyl)-N-hydroxy-1-(2-thienylcarbonyl)-4-piperidinecarboxamide
Step 1

Methyl 4-(4-but-2-ynyloxybenzenesulfonyl)-1-(2-thienylcarbonyl)-4-piperidinecarboxylate To a solution of 4-(4-but-2-ynyloxy-benzenesulfonyl)-piperidine-4-carboxylic acid methyl ester (500 mg, 1.29 mmol) in methylene chloride (10 ml) was added triethylamine (261 mg, 2.58 mmol), thiophenylcarbonyl chloride (227 mg, 1.55 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 480 mg (81%) of the product as a solid. HR-MS: m/z Calculated for $C_{22}H_{23}NO_6S_2$ 462.1040; Found 462.1039.
Step 2

4-(4-but-2-ynyloxybenzenesulfonyl)-1-(2-thienylcarbonyl)-4-piperidinecarboxylic acid 4-(4-but-2-ynyloxybenzenesulfonyl)-1-(2-thienylcarbonyl)-4-piperidinecarboxylic acid was prepared following the procedure of Example 64 (step 5). Starting from Methyl 4-(4-but-2-ynyloxybenzenesulfonyl)-1-(2-thienylcarbonyl)-4-piperidinecarboxylate (435 mg, 0.94 mmol) in 8 ml of tetrahydrofuran:methanol (1:1), and 1N sodium hydroxide (1.89 ml, 1.89 mmol) to obtain 360 mg (86%) of the acid. HR-MS: m/z Calculated for $C_{21}H_{21}NO_6S_2$ 448.0883; Found 448.0882.
Step 3

4-(4-but-2-ynyloxybenzenesulfonyl)-N-hydroxy-1-(2-thienylcarbonyl)-4-piperidinecarboxamide 4-(4-but-2-ynyloxybenzenesulfonyl)-N-hydroxy-1-(2-thienylcarbonyl)-4-piperidinecarboxamide was prepared following the procedure Example 64 (step 6). Starting from 4-(4-but-2-ynyloxybenzenesulfonyl)-1-(2-thienylcarbonyl)-4-piperidinecarboxylic acid (335 mg, 0.75 mmol) in dimethylformamide (7 ml), 1-hydroxybenzotriazole (121 mg, 0.90 mmol), 1-[3-(dimethylamino)propyl]-3-ethylcarbodiimide hydrochloride (201 mg, 1.05 mmol), N-methylmorpholine (0.124 ml, 1.13 mmol), and hydroxylamine (0.229 ml, 3.75 mmol), 216 mg (62%) of the product was isolated as a solid. HR-MS: m/z Calculated for $C_{21}H_{22}N_2O_6S_2$ 463.0992; Found 463.0988.

EXAMPLE 72

4-(4-but-2-ynyloxybenzenesulfonyl)-N-hydroxy-1-[(4-methoxyphenyl)sulfonyl]-4-piperidinecarboxaniide Step 1

Methyl 4-(4-but-2-ynyloxybenzenesulfonyl)-1-[(4-methoxyphenyl)sulfonyl]-4-piperidinecarboxylate To a solution of 4-(4-but-2-ynyloxy-benzenesulfonyl)-piperidine-4-carboxylic acid methyl ester (500 mg, 1.29 mmol) in methylene chloride (10 ml) was added triethylamine (261 mg, 2.58 mmol), 4-methoxyphenylsulfonyl chloride (320 mg, 1.55 mmol) followed by a catalytic amount of dimethylaminopyridine. The resulting mixture was stirred for 15 hours at room temperature, quenched with water and extracted with methylene chloride. The organic layer was dried over anhydrous sodium sulfate and concentrated to give 590 mg (88%) of the product as a solid. HR-MS: m/z Calculated for $C_{24}H_{72}NO_8S_2$ 522.1251; Found 522.1252.

Step 2

4-(4-But-2-ynyloxybenzenesulfonyl)-1-[(4-methoxyphenyl) sulfonyl]-4-piperidinecarboxylic acid 4-(4-But-2-ynyloxybenzenesulfonyl)-1-[(4-methoxyphenyl)sulfonyl]-4-piperidine carboxylic acid was prepared following the procedure of Example 64 (step 5). Starting from methyl 4-(4-but-2-ynyloxybenzenesulfonyl)-1-[(4-methoxyphenyl)sulfonyl]-4-piperidinecarboxylate (545 mg, 1.04 mmol) in 8 ml of tetrahydrofuran:methanol (1:1), and 1N sodium hydroxide (2.09 ml, 2.09 mmol) to obtain 446 mg (85%) of the acid. HR-MS: m/z Calculated for $C_{23}H_{25}NO_8S_2$ 508.1094; Found 508.1073.

Step 3

4-(4-but-2-ynyloxybenzenesulfonyl)-N-hydroxy-1-[(4-methoxyphenyl)sulfonyl]-4-piperidinecarboxamide 4-(4-But-2-ynyloxybenzenesulfonyl)-N-hydroxy-1-[(4-methoxyphenyl)sulfonyl]-4-piperidinecarboxamide was prepared following the procedure Example 64 (step 6). Starting from 4-(4-But-2-ynyloxybenzenesulfonyl)-1-[(4-methoxyphenyl)sulfonyl]-4-piperidinecarboxylic acid (402 mg, 0.79 mmol) in dimethylformamide (8 ml), 1-hydroxybenzotriazole (128 mg, 0.95 mmol), 1-[3-(dimethylamino)propyl]-3-ethylcarbodimide hydrochloride (212 mg, 1.11 mmol), N-methylmorpholine (0.130 ml, 1.19 mmol), and hydroxylamine (0.242 ml, 3.95 mmol), 396 mg (96%) of the product was isolated as a solid. HR-MS: m/z Calculated for $C_{23}H_{26}N_2O_8S_2$ 523.1203; Found 523.1198.

EXAMPLE 73

4-(4-but-2-ynyloxybenzenesulfonyl)-N-hydroxy-1-[(2,2,5-trimethyl-1,3-dioxan-5-yl)carbonyl]-4-piperidinecarboxamide Step 1

Methyl 4-(4-but-2-ynyloxybenzenesulfonyl)-1-[(2,2,5-trimethyl-1,3-dioxan-5-yl)carbonyl]-4-piperidinecarboxylate Methyl 4-(4-but-2-ynyloxybenzenesulfonyl)-1-[(2,2,5-trimethyl-1,3-dioxan-5-yl)carbonyl]-4-piperidinecarboxylate was prepared following the procedure Example 64 (step 6). Starting from 4-(4-but-2-ynyloxybenzenesulfonyl)-piperidine-4-carboxylic acid methyl ester (500 mg, 1.29 mmol) in dimethylformamide (10 ml), (2,2,5-trimethyl-1,3-dioxan-5-yl)carboxylic acid (224 mg, 1.29 mmol), 1-hydroxybenzotriazole (209 mg, 1.56 mmol), 1-[3-(dimethylamino)propyl]-3-ethylcarbodiimide hydrochloride (346 mg, 1.81 mmol), and N-methylmorpholine (0.212 ml, 1.94 mmol), to obtain 385 mg (59%) of the product as a solid. HR-MS: m/z Calculated for $C_{25}H_{33}NO_8S$ 508.2000; Found 508.1998.

Step 2

4-(4-but-2-ynyloxybenzenesulfonyl)-1-[(2,2,5-trimethyl-1,3-dioxan-5-yl)carbonyl]-4-piperidinecarboxylic acid 4-(4-But-2-ynyloxybenzenesulfonyl)-1-[(2,2,5-trimethyl-1,3-dioxan-5-yl)carbonyl]-4-piperidinecarboxylic acid was prepared following the procedure of Example 40 (step 5). Starting from Methyl 4-(4-but-2-ynyloxybenzenesulfonyl)-1-[(2,2,5-trimethyl-1,3-dioxan-5-yl)carbonyl]-4-piperidinecarboxylate (335 mg, 0.66 mmol) in 4 ml of tetrahydrofuran:methanol (1:1), and 1N sodium hydroxide (1.3 ml, 1.3 mmol) to obtain 315 mg (97%) of the acid. HR-MS: m/z Calculated for $C_{24}H_{31}NO_8S$ 494.1843; Found 494.1835.

Step 3

4-(4-But-2-ynyloxybenzenesulfonyl)-N-hydroxy-1-[(2,2,5-trimethyl-1,3-dioxan-5-yl)carbonyl]-4-piperidinecarboxamide 4-(4-But-2-ynyloxybenzenesulfonyl)-N-hydroxy-1-[(2,2,5-trimethyl-1,3-dioxan-5-yl)carbonyl]-4-piperidinecarboxamide was prepared following the procedure Example 64 (step 6). Starting from 4-(4-but-2-ynyloxybenzenesulfonyl)-1-[(2,2,5-trimethyl-1,3-dioxan-5-yl)carbonyl]-4-piperidinecarboxylic acid (280 mg, 0.57 mmol) in dimethylformamide (6 ml), 1-hydroxybenzotriazole (92 mg, 0.57 mmol), 1-[3-(dimethylamino)propyl]-3-ethylcarbodiimide hydrochloride (153 mg, 0.80 mmol), N-methylmorpholine (0.094 ml, 0.85 mmol), and hydroxylamine (0.174 ml, 2.85 mmol), 180 mg (62%) of the product was isolated as a solid. HR-MS: m/z Calculated for $C_{24}H_{32}N_{12}O_8S$ 531.1771; Found 531.1768.

EXAMPLE 74

4-(4-But-2-ynyloxybenzenesulfonyl)-N-hydroxy-1-[3-hydroxy-2-(hydroxymethyl)-2-methylpropanoyl]-4-piperidinecarboxamide To a solution of product from Example 73 (150 mg, 0.29 mmol) in tetrahydrofuran (2 ml) was added 1N aqueous hydrochloric acid (2 ml) and the resulting mixture was stirred for 4 hours. The organic layer was washed with sodium bicarbonate, brine and dried over anhydrous sodium sulfate. Solvent was removed to obtain 40 mg (29%) of the product. HR-MS: m/z Calculated for $C_{21}H_{28}N_2O_8S$ 469.1639; Found 469.1637.

EXAMPLE 75

Tert-butyl 4-{[4-(2-butynyloxy)phenyl]sulfonyl}-4-[(hydroxyaniino)carbonyl]-1-piperidinecarboxalate Step 1

1-(tert-butoxycarbonyl)-4-{[4-(2-butynyloxy)phenyl]sulfonyl}-4-piperidinecarboxylic acid A solution of 4-(4-but-2ynyloxybenzenesulfonyl)-piperidine-1,4-dicarboxylic acid tert-butyl ester methyl ester (from example 64, step 2) (15 g, 33.2 mmol) in water (100 mL), methanol (50 mL) and tetrahydrofuran (50 mL) was treated with lithium hydroxide hydrate (2.73 g, 66.4 mmol) and heated at reflux for 8 h. The reaction mixture was concentrated in vacuo and filtered through celite. To the filtrate was added aqueous 1N hydrochloric acid. A thick gum was obtained which was dissolved in dichloromethane and washed with water. Concentration of the organic phase gave a foam (14.9 g). Trituration with diethyl ether gave 1-(tert-butoxycarbonyl)-4-{[4-(2-butynyloxy)phenyl] sulfonyl}-4-piperidinecarboxylic acid as a white powder. Electrospray MS m/z 482 (M−H)$^-$ Step 2

Tert-butyl 4-{[4-(2-butynyloxy)phenyl]sulfonyl}-4-[(hydroxyamino) carbonyl]-1-piperidinecarboxalate Dimethylformamide (3.53 mL, 46 mmol) was added to a solution of oxalyl chloride (22.9 mL of a 2.0M solution in dichloromethane) in dichloromethane (25 mL) at 0° C. After 15 min a solution of 1-(tert-butoxycarbonyl)-4-{[4-(2-butynyloxy)phenyl]sulfonyl}-4-piperidinecarboxylic acid (1 g, 22.9 mmol) in dimethylformamide was added and the reaction mixture was allowed to warm to room temperature. After 1 h the reaction mixture was added to a mixture of hydroxylamine hydrochloride (16 g, 229 mmol), triethylamine (48 mL, 344 mmol), water (123 mL) and tetrahydrofuran (500 mL) that had been stirring at 0° C. for 15 min. The reaction was allowed to warm to room temperature. After 18 h it was then diluted with ethyl acetate and washed with saturated aqueous sodium bicarbonate (3×), then dried over potassium carbonate and concentrated in vacuo. Trituration with diethyl ether gave tert-butyl 4-{[4-(2-butynyloxy)phenyl]sulfonyl}-4-[(hydroxyamino)carbonyl]-1-piperidinecarboxalate as a white powder (6.3 g). $^1$H NMR (dmso d6, 300 MHz) δ1.38 (s, 9H, t-butyl), 1.6–1.7 (m, 2H, CHH), 1.85 (t, 3H, CH3, J=2.2 Hz), 2.2–2.3 (m, 2H, CHH), 2.5–2.7 (m, 2H, NCHH), 3.9–4.0 (m, 2H, NCHH), 4.87 (q, 2H), OCH2, J=2.2 Hz), 7.1–7.7 (m, 4H, ArH). Electrospray MS m/z 453 (M+H)$^+$

EXAMPLE 76

4-{[4-(2-butynyloxy)phenyl]sulfonyl}-N-hydroxy-4-piperidinecarboxamide hydrochloride To tert-butyl 4-{[4-(2-butynyloxy)phenyl]sulfonyl}-4-[(hydroxyamino)carbonyl]-1-piperidinecarboxalate (prepared from Example 75) (6.3 g, 13.9 mmol) was added 4N hydrochloric acid in dioxane. After 6 h the reaction mixture was comcentrated in vacuo. Methanol was added and the resulting mixture concentrated in vacuo. Dichloromethane was added and removed in vacuo (2×). Trituration with diethyl ether gave 4-{[4-(2-butynyloxy)phenyl] sulfonyl}-N-hydroxy-4-piperidinecarboxamide hydrochloride as a white powder (5.14 g). $^1$H NMR (dmso d6, 300 MHz) δ1.86 (t, 3H, CH3, J=2.2 Hz), 2.0–2.7 (m, 8H, CH2), 4.89 (q, 2H OCH2, J=2.2 Hz), 7.1–7.8 (m, 4H, ArH), 8.8–11.0 (m, 4H, NH2, NHOH). Electrospray MS m/z 353 (M+H)$^+$

EXAMPLE 77

Methyl ({4-{[4-(2-butynyloxy)phenyl]sulfonyl}-4-[(hydroxyamino)carbonyl]-1-piperidinyl}methyl) benzoate hydrochloride To 4-{[4-(2-butynyloxy)phenyl]sulfonyl}-N-hydroxy-4-piperidinecarboxamide hydrochloride (prepared from Example 76) (2.5 g, 6.43 mmol) and methyl 4-(bromomethyl)benzoate (1.62 g, 7.07 mmol) in methanol (100 mL) at 50° C. was added triethylamine (2.25 mL, 16.1 mmol). After 30 min additional methanol (50 mL) was added. After 18 h the reaction mixture was concentrated in vacuo and 1N aqueous hydrochloric acid (10 mL) and water was added. The resulting solid was isolated and to it was added methanol (20 mL) and 1N hydrochloric acid in diethylether (15 mL). To the resulting solution was added diethyl ether. Trituration of the precipitate gave methyl ({4-{[4-(2-butynyloxy)phenyl]sulfonyl}-4-[(hydroxyamino)carbonyl]-1-piperidinyl}methyl)benzoate hydrochloride as a white powder (2.4 g). $^1$H NMR (dmso d6, 300 MHz) δ1.85 (t, 3H, CH3, J=2.2 Hz), 2.1–3.5 (m, 8H, CH2), 3.87 (S, 3H, OCH3), 4.40 (bd s, 2H, NCH2Ar), 4.89 (q, 2H, OCH2, J=2.2 Hz), 7.1–8.1 (m, 8H, ArH), 9.3–11.2 (m, 3H, NH, NHOH). Electrospray MS m/z 501.5 (M+H)$^+$

EXAMPLE 78

4-({4-{[4-(2-butynyloxy)phenyl]sulfonyl}-4-[(hydroxyamino)carbonyl-1-piperidinyl}methyl) benzoic acid hydrochloride To methyl ({4-{[4-(2-butynyloxy)phenyl]sulfonyl}-4-[(hydroxyamino)-carbonyl]-1-piperidinyl}methyl)benzoate hydrochloride (Prepared from example 77) (0.072 g, 0.134 mmol) in methanol (1 mL) was added 1N aqueous sodium hydroxide (0.5 mL). After 18 h 1N aqueous hydrochloric acid (0.5 mL) was added and the reaction mixture concentrated in vacuo. Water was added and the precipitate triturated to give 4-({4-{[4-(2-butynyloxy)phenyl]sulfonyl}-4-[(hydroxyamino)-carbonyl]-1-piperidinyl}methyl)benzoic acid hydrochloride as an off-white solid (0.040 g). $^1$H NMR (dmso d6, 300 MHz) δ1.85 (t, 3H, CH3, J=2.2 Hz), 2.1–3.5 (m, 8H, CH2), 4.37 (bd s, 2H, NCH2Ar), 4.89 (q, 2H, OCH2, J=2.2 Hz), 7.0–8.1 (m, 2ArH), 9.3–11.2 (m, 3H, NH, NHOH), 13.1 (bd s, 1H, COOH). Electrospray MS m/z 487.1 (M+H)$^+$

EXAMPLE 79

1-[4-(Aminocarbonyl)benzyl]-4-{[4-(2-butynyloxy) phenyl]sulfonyl}-N-hydroxy-4-piperidinecarboxamide hydrochloride To methyl ({4-{[4-(2-butynyloxy)phenyl]sulfonyl}-4-[(hydroxyamino)carbonyl]-1-piperidinyl}methyl)benzoate hydrochloride (from example 77) (0.20 g) in methanol (10 mL) was added concentrated aqueous ammonium hydroxide (4 mL). After several weeks the reaction mixture was concentrated in vacuo and chromatographed on silica gel (methanol/dichloromethane) to give a white powder which was dissolved in dichloromethane and methanol. 1N Hydrochloric acid in diethylether was added followed by additional diethylether. Trituration gave 1-[4-(aminocarbonyl) benzyl]-4-{[4-(2-butynyloxy)phenyl]sulfonyl}-N-hydroxy-4-piperidinecarboxamide hydrochloride as a white powder (0.106 g). $^1$H NMR (Dmso d6, 300 MHz) δ1.85 (t, 3H, CH3, J=2.2 Hz), 2.2–3.5 (m, 8H, CH2), 4.33 (bd s, 2H, NCH2Ar), 4.89 (q, 2H, OCH2, J=2.2 Hz), 7.1–8.0 (m, 8H, ArH), 7.47 (s, CONH), 8.04 (s, 1H, CONH), 9.35 (bd s, 1H, NHOH), 10.44 (bd s, 1H, NHOH), 11.1 (s, 1H, NH). Electrospray MS m/z 486.3 (M+H)$^+$

EXAMPLE 80

Tert-butyl 4-{[4-(but-2-ynyloxy)phenyl]sulfinyl}-4-[(hydroxyamino)carbonyl]piperidine-1-carboxalate To tert-butyl 4-{[4-(but-2-ynyloxy)phenyl]sulfanyl}-4-[(hydroxyamino)carbonyl]piperidine-1-carboxalate (0.30 g)

(obtained from example 14) in methanol (10 mL) was added 30% aqueous hydrogen peroxide (3 mL). After 3 days water and dichloromethane were added and the organic phase washed with aqueous Na2SO3. Concentration of the organic phase gave material which was dissolved in methanol (8 mL) and treated with 30% aqueous hydrogen peroxide. After several days workup as above gave tert-butyl 4-{[4-(but-2-ynyloxy)phenyl]sulfinyl}-4-[(hydroxyamino)carbonyl] piperidine-1-carboxalate as a colorless foam (0.26 g). $^1$H NM (dmso d6, 300 MHz) $\delta$1.38 (s, 9H, t-butyl), 1.5–1.7 (m, 2H, CHH), 1.85 (t, 3H, CH3, J=2.2 Hz), 2.1–2.2 (m, 2H, CHH), 2.5–2.7 (m, 2H, NCHH), 3.8–4.0 (m, 2H, NCHH), 4.81 (q, 2H, OCH2, J=2.2 Hz), 7.1–7.4 (m, 4H, ArH), 9.1 (s, 1H, NHOH), 10.8 (s, 1H, NHOH). Electrospray MS m/z 437.2 (M+H)$^+$

EXAMPLE 81

4-(4-(But-2-ynyloxy-benzenesulfinyl)-piperidine-4-carboxylic acid hydroxamide hydrochloride To tert-butyl 4-{[4-(but-2-ynyloxy)phenyl]sulfinyl}-4-[(hydroxyamino) carbonyl]piperidine-1-carboxalate (prepared from example 80) (0.26 g) was added 4N hydrochloric acid in dioxane (4 mL). After 1 h the reaction mixture was concentrated in vacuo. Methanol was added and removed in vacuo. Dichloromethane was added and removed in vacuo 3× to give 4-(4-(But-2-ynyloxy-benzenesulfinyl)-piperidine-4-carboxylic acid hydroxamide hydrochloride as a yellow solid (0.19 g). $^1$H NMR (dmso d6, 300 MHz) $\delta$1.86 (t, 3H, CH3, J=2.2 Hz), 1.7–2.8 (m, 8H, CH2), 4.82 (q, 2H, OCH2, J=2.2 Hz), 7.1–7.5 (m, 4H, ArH), 8.4–11.0 (m, 4H, NH2, NHOH). Electrospray MS m/z 337.2 (M+H)$^+$

EXAMPLE 82

1-(4-Bromo-benzyl)-4-(4-But-2-ynyloxy-benzenesulfinyl)-piperidine-4-carboxylic acid hydroxamide hydrochloride To a solution of 4-(4-(But-2-ynyloxy-benzenesulfinyl)-piperidine-4-carboxylic acid hydroxamide hydrochloride (prepared from example 81) (0.162 g, 0.434 mmol) and 4-bromobenzylbromide (0.120 g, 0.478 mmol) in methanol was added triethylamine (0.13 mL, 0.91 mmol). After 4 h the reaction mixture was concentrated in vacuo and chromatographed on silica gel (methanol/dichloromethane) to give an oily solid which was dissolved in dichloromethane. To the solution was added 1N hydrochloric acid in ether (1 mL). Concentration in vacuo gave 1-(4-Bromo-benzyl)-4-(4-But-2-ynyloxy-benzenesulfinyl)-piperidine-4-carboxylic acid hydroxamide hydrochloride as a tan solid (0.102 g). $^1$H NMR (dmso d6, 300 MHz) $\delta$1.85 (t, 3H, CH3, J=2.2 Hz), 1.9–3.5 (m, 8H, CH2), 3.87 (S, 3H, OCH3), 4.3 (bd s, 2H, NCH2Ar), 4.82 (q, 2H, OCH2, J=2.2 Hz), 7.0–7.8 (m, 8H, ArH), 9.2–11.1 (m, 3H, NH, NHOH). Electrospray MS m/z 505.1/507.2 (M+H)$^+$

Pharmacology

Representative compounds of this invention were evaluated as inhibitors of the enzymes MMP-1, MMP-9, MMP-13 and TNF-a converting enzyme (TACE). The standard pharmacological test procedures used, and results obtained which establish this biological profile are shown below.

Test Procedures for Measuring MMP-1, MMP-9, and MMP-13 Inhibition

These standard pharmacological test procedures are based on the cleavage of a thiopeptide substrates such as Ac-Pro-Leu-Gly-(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 $\mu$l) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% CI are estimated using linear regression.

Test Procedure for Measuring TACE Inhibition

Using 96-well black microtiter plates, each well receives a solution composed of 10 $\mu$L TACE (final concentration 1 $\mu$g/mL), 70 $\mu$L Tris buffer, pH 7.4 containing 10% glycerol (final concentration 10 mM), and 10 $\mu$L of test compound solution in DMSO (final concentration 1 $\mu$M, DMSO concentration <1%) and incubated for 10 minutes at room temperature. The reaction is initiated by addition of a fluorescent peptidyl substrate (final concentration 100 $\mu$M) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generate using multiple doses of drug and $IC_{50}$ values with 95% CI are estimated using linear regression.

Human Monocytic THP-1 Cell Differentiation Assay for Soluble Proteins (THP-1 Soluble Protein Assay)

Mitogenic stimulation of THP-1 cells cause differentiation into macrophage like cells with concomitant secretion of tumor necrosis factor (TNF-a) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-a and possibly TNF-R p75/80 and TNF-R p55/60, but not IL-8, is mediated by an enzyme called TNF-a converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia. They can be grown in culture and differentiated into macrophage like cells by stimulation with mitogens.

For the assay, THP-1 cells are seeded from an ATCC stock which was previously grown and frozen back at $5\times10^6$ /ml/vial. One vial is seeded into a T25-flask with 16 mls of RPMI-1640 with glutamax (Gibco) media containing 10% fetal bovine serum, 100 units/ml penicillin, 100 μg/ml streptomycin, and $5\times10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of $1\times10^5$ /ml.

To perform an assay, the THP-1 cells are co-incubated in a 24 well plate with 50 ml/well of a 24 mg/ml stock of Lipopolysacharide (LPS) (Calbiochem Lot#B13189) at 37° C. in 5% $CO_2$ at a concentration of $1.091\times10^6$ cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1% final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-a ELISA. Following 24 hours of incubation, 700 ml/well of TCS is removed and used for analysis in TNF-R p75/80, TNF-R p55/60 and IL-8 ELISAs.

In addition, at the 24 hours timepoint, and the cells for each treatment group are collected by resuspension in 500 μl/well of THP-1 media and transferred into a FACS tube. Two ml/tube of a 0.5 mg/ml stock of propidium iodide (PI) (Boerhinger Mannheim cat. # 1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-a, TNF-R p75/80 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration. Percent change in each soluble protein evaluated from the "vehicle positive control" was calculated for each compound concentration with the following formula:

$$\% \text{ Change} = \frac{\text{pg/ml (compound)} - \text{pg/ml (veh pos control)}}{\text{pg/ml (veh pos control)} - \text{pg/ml (veh neg control)}} \times 100$$

For the soluble protein (TNF-a, p75/80, p55/60, IL-8) studies under stimulated conditions, the mean pg/ml of duplicate wells were determined and the results expressed as percent change from "vehicle positive control". For the soluble protein (p75/80 and p55/60 receptors) studies under non-stimulated conditions, the mean pg/ml of duplicate wells were determined and the results expressed as percent change from "vehicle positive control" utilizing the following formula:

$$\% \text{ Change} = \frac{\text{pg/ml (compound neg control)} - \text{pg/ml (veh neg control)}}{\text{pg/ml (veh neg control)}} \times 100$$

IC50 values for each compound are calculated by non-linear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

References

Bjornberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-1 cells in vitro. Cellular Immun. 138:1–10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:1711–176, 1980.

Results of the above in vitro matrix metalloproteinase inhibition, TACE inhibition and THP standard pharmacological test procedures are given in Table 1

TABLE 1

| Example # | TACE $IC_{50}{}^a$ | THP @3 $\mu M^b$ | MMP1 $IC_{50}{}^c$ | MMP9 $IC_{50}{}^a$ | MMP13 $IC_{50}{}^a$ |
|---|---|---|---|---|---|
| 1 | 65 | 46% | 3.3 | 385 | 155 |
| 2 | 82 | 68% | 2.57 | 164 | 39.6 |
| 3 | 55 | 34% | 9 | 280 | 90 |
| 4 | 90 | 25% | 2.6 | 148 | 47.3 |
| 5 | 188 | 30% | .3 | 400 | 180 |
| 6 | 393 | NT | 32.9% | 58.9% | 60% |
| 7 | 123 | 21% | 2.5 | 225 | 59.4 |
| 8 | 195 | 21% | 4.7 | 218 | 72 |
| 9 | 166 | 12% | 2.1 | 96.2 | 35.2 |
| 10 | | | | | |
| 11 | 98 | 7% | 0.143 | 5.8 | 3.1 |
| 12 | 41.8% | +58 | 15 | 1000 | 1500 |
| 13 | 882 | +69% | 10 | 2000 | 800 |
| 14 | 67% | NT | 26% | 21% | 32% |
| 15 | 38% | NT | 24% | 25% | 24% |
| 16 | 46% | NT | 10 | 2056 | 1465 |
| 17 | 139 | 0 | 10 | 2296 | 946 |
| 18 | 11.4 | 45% | 10 | 1276 | 98 |
| 19 | 74 | 4% | 10 | 10000 | 1321 |
| 20 | 30.1 | 47% | 2643 nM | 568 | 121 |
| 21 | 509 | 6% | >10 | 3504 | 858 |
| 22 | 48.4% | 5% | >10 | 1814 | 1076 |
| 23 | 86.2 | 62% | 3206 nM | 160 | 64.4 |
| 24 | 180 | 41% | 5671 nM | 2078 | 463 |
| 25 | 695 | 3% | >10 | 2740 | 1177 |
| 26 | 136 | 63% | 1994 nM | 25.1 | 22.1 |
| 27 | 168 | 13% | >10 | 1542 | 426 |
| 28 | 150 | 13% | 106 nM | 15.4 | 5.3 |
| 29 | 127 | 13% | 91 nM | 16 | 4.7 |
| 30 | 102 | 0 | >10 | 5899 | 2911 |
| 31 | 314 | 8 | >10 | >10000 | >10000 |
| 32 | 100 | 0 | >10 | >10000 | 2752 |
| 33 | 327 | 8 | >10 | ~5000 | ~10000 |
| 34 | 33 | 68 | ~10 | 1393 | 102 |
| 35 | 57 | 14 | >10 | >10000 | ~10000 |
| 36 | 4.8 | 58 | 3.9 | 2828 | 380 |
| 37 | 18 | NT | 8.6 | 8575 | 1024 |
| 38 | 19 | 53 | ~10 | 1443 | 279 |
| 39 | 11 | NT | 3.77 | 4275 | 809 |
| 40 | 63 | 41 | 0.707 | 425 | 36 |
| 41 | 37 | 60 | 2.677 | 1121 | 254 |
| 42 | 12 | 78% | ~10 | >10000 | 1627 |
| 43 | 13 | 66 | ~10 | >10000 | 1640 |
| 44 | 56 | 49 | 35% | 50.6% | 2381 |
| 45 | 25 | 48 | 3.8 | 3584 | 423 |
| 46 | 105 | NT | NT | NT | 55.6% |
| 47 | 227 | NT | NT | NT | 275 |
| 48 | 66 | NT | NT | NT | 1035 |
| 49 | 32.6 | NT | NT | NT | 1727 |
| 50 | 18.3 | NT | NT | NT | 352 |
| 51 | 211.5 | NT | NT | NT | 403 |
| 52 | 41.8 | NT | NT | NT | 3710 |
| 53 | 20.8 | NT | NT | NT | 1165 |
| 54 | 32.2 | NT | NT | NT | 104 |
| 55 | 70.7 | NT | NT | NT | 600 |
| 56 | 31.1 | NT | NT | NT | 3.2 |
| 57 | 694 | NT | NT | NT | 458 |
| 58 | 21.1 | NT | NT | NT | 179 |
| 59 | 53.3 | NT | NT | NT | 11.2 |
| 60 | 38.4 | NT | NT | NT | 8.0 |
| 61 | 56.4 | NT | NT | NT | 575 |
| 62 | 64.6 | NT | NT | NT | 64.6 |
| 63 | 66.6 | NT | NT | NT | 2229 |
| 64 | 47 | 30 | 4.076 | 560 | 136 |
| 65 | 73 | 3 | 3.532 | 448 | 105 |
| 66 | 106 | 73 | 2.768 | 430 | 81 |
| 67 | 72 | 18 | 2.028 | 853 | 345 |
| 68 | 77 | 10 | 2.249 | 1333 | 503 |
| 69 | 115 | 14 | 3.999 | 1246 | 499 |
| 70 | 87 | 62 | 2.963 | 639 | 113 |
| 71 | 113 | 14 | 3.117 | 811 | 183 |
| 72 | 221 | 56 | 4.157 | 1211 | 369 |
| 73 | NT | NT | NT | NT | NT |
| 74 | 132 | 39 | 4.338 | 963 | 287 |
| 75 | 134 | −4 | 2.588 | 1951 | 284 |
| 76 | 201 | 26 | 4.503 | 7886 | 4019 |
| 77 | 114 | 52 | 2.187 | 149 | 349 |
| 78 | 64.5 | 64 | 1.051 | 364 | 73.7 |
| 79 | 70 | 83 | 2.420 | 129 | 50.6 |
| 80 | 90 | −7 | 186 | 122 | 40 |
| 81 | 277 | 25 | 1.877 | 1035 | 593 |
| 82 | 135 | 16 | 257 | 125 | 62 |

$^a$ = nM or % inhibition
$^b$ = % inhibition
$^c$ = $\mu M$ or % inhibition, unless otherwise indicated Based on the results obtained in the standard pharmacological test procedures described, above, the compounds of this invention were shown to be inhibitors of the enzymes MMP-1, MMP-9, MMP-13 and TNF-a converting enzyme (TACE) and are therefore useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. A compound of formula

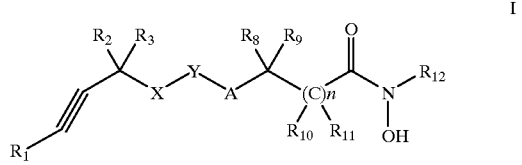

wherein:

$R_1$ is hydrogen, aryl, heteroaryl, alkyl of 1–8 carbon atoms, alkenyl of 2–6 carbon atoms, alkynyl of 2–6 carbon atoms, cycloalkyl of 3–6 carbon atoms, or —$C_4$–$C_8$-cycloheteroalkyl;

$R_2$ and $R_3$ are each, independently, hydrogen, alkyl of 1–6 carbon atoms, —CN, or —CCH;

$R_7$ is hydrogen, aryl, aralkyl, heteroaryl, heteroaralkyl, alkyl of 1–6 carbon atoms, alkenyl of 2–6 carbon atoms, alkynyl of 1–6 carbon atoms, cycloalkyl of 3–6 carbon atoms, —C(O)—$R_1$, —$SO_2$—$R_1$, —C(O)—$NHR_1$, —C(O)$NR_5R_6$, —C(O)$R_1NR_5R_6$, —C(O)—$OR_1$, —C(NH)—$NH_2$;

$R_8$ and $R_9$ together with the carbon atom to which they are attached form a piperidinyl or tetrahydropyranyl ring;

$R_{10}$, and $R_{11}$ are each, independently, hydrogen, aryl, heteroaryl, cycloalkyl of 3–6 carbon atoms, —$C_4$–$C_8$-cycloheteroalkyl, alkyl of 1–18 carbon atoms, alkenyl of 2–18 carbon atoms, or alkynyl of 2–18 carbon atoms;

$R_{12}$ is hydrogen, aryl or heteroaryl, cycloalkyl of 3–6 carbon atoms, —$C_4$–$C_8$-cycloheteroalkyl, or alkyl of 1–6 carbon atoms;

A is O, S, SO, $SO_2$, $NR_7$, or $CH_2$;

X is O, S, SO, $SO_2$, $NR_7$, or $CH_2$;

Y is phenyl, with the proviso that A and X are not bonded to adjacent atoms of Y; and n is 0–2; or a pharmaceutically acceptable salt thereof.

2. A compound of claim 1 selected from the group consisting of:

1-(4-Bromo-benzyl)-4-(4-but-2-ynyxoy-benzenesulfonyl)-piperdine-4-carboxylic acid hydroxyamide;

4-(4-But-2-ynyloxy-benzenesulfonyl)-1-(4-methoxybenzyl)-piperdine-4-carboxylic acid hydroxyamide;

4-(4-But-2-ynyloxy-benzenesulfonyl)-1-(4-chloro-benzyl)-piperdine-4-carboxylic acid hydroxyamide;

1-Benzyl-4-(4-but-2-ynyloxy-benzenesulfonyl)-piperdine-4-carboxylic acid hydroxamide;

1-(4-Bromo-benzyl)-4-(4-pent-2-ynyloxy-benzenesulfonyl)-piperdine-4-carboxylic acid hydroxyamide;

1-(4-Bromo-benzyl)-4-(4-oct-2-ynyloxy-benzenesulfonyl)-piperdine-4-carboxylic acid hydroxyamide;

4-(4-But-2-ynyloxy-benzenesulfonyl)-1-(4-fluoro-benzyl)-piperdine-4-carboxylic acid hydroxyamide;

4-(4-But-2-ynyloxy-benzenesulfonyl)-1-(4-cyano-benzyl)-piperidine-4-carboxylic acid hydroxamide;

4-(4-But-2-ynyloxy-benzenesulfonyl)-1-(4-methyl-benzyl)-piperidine-4-carboxylic acid hydroxamide;

4-(4-But-2-ynyloxy-benzenesulfonyl)-1-(3,4-dichloro-benzyl)-piperidine-4-carboxylic acid hydroxamide;

1-(4-Bromo-benzyl)-4-(4-prop-2-ynyloxy-benzenesulfonyl)-piperdine-4-carboxylic acid hydroxamide;

1-(4-Bromo-benzyl)-4-[4-(4-piperdin-4-yl-but-2-ynyloxy)-benzenesulfonyl]-piperdine-4-carboxylic acid hydroxamide;

1-(4-Bromo-benzyl)-4-[4-(4-morpholin-4-yl-but-2-ynyloxy)-benzene-sulfonyl]-piperdine-4-carboxylic acid hydroxyamide;

4-(4-But-2-ynyloxy-phenylsulfanyl)-4-hydroxycarbamoyl-piperidine-1-carboxylic acid tert-butyl ester;

4-(4-But-2-ynyloxy-phenylsulfanyl)-piperidine-4-carboxylic acid hydroxyamide;

1-(4-Bromo-benzyl)-4-(4-but-2-ynyloxy-phenylsulfanyl)-piperidine-4-carboxylic acid hydroxyamide;

4-(4-But-2-ynyloxy-phenylsulfanylmethyl)-tetrahydro-pyran-4-carboxylic acid hydroxyamide;

4-(4-But-2-ynyloxy-benzenesulfonylmethyl)-tetrahydro-pyran-4-carboxylic acid hydroxyamide;

4-(4-But-2-ynyloxy-benzenesulfinylmethyl)-tetrahydro-pyran-4-carboxylic acid hydroxyamide;

4-{[4-(2-butynyloxy)phenyl]sulfonyl}-N-hydroxytetrahydro-2H-pyran-4-carboxamide;

1-benzyl-4-{[3-(2-butynyloxy)phenyl]sulfonyl}-N-hydroxy-4-piperdine carboxamide;

4-{[4-(2-butynyloxy)phenyl]sulfonyl}-N-hydroxy-1-isopropyl-4-piperidine carboxamide;

4-{[4-(2-butynyloxy)phenyl]sulfonyl}-N-hydroxy-1-(3-pyridinylmethyl)-4-piperidine carboxamide;

3-{[4-(2-Butynyloxy)phenyl]sulfonyl}-1-ethyl-N-hydroxy-3-piperidinecarboxamide;

3-{[4-(2-butynyloxy)phenyl]sulfonyl}-1-(4-chlorobenzyl)-N-hydroxy-3-piperidinecarboxamide;

4-{[4-(2-Butynyloxy)phenyl]sulfonyl}-1-[4-(2-piperidin-1-yl-ethoxy)-benzyl]-piperidine-4-carboxylic acid hydroxyamide;

4-{[4-(2-Butynyloxy)phenyl]sulfonyl}-1-(3-pentanyl)-piperidine-4-carboxylic acid hydroxyamide;

1-(4-Methoxy-benzyl)-4-(4-prop-2-ynyloxy-benzenesulfonyl)-piperidine-4-carboxylic acid hydroxyamide;

1-(4-Chloro-benzyl)-4-(4-prop-2-ynyloxy-benzenesulfonyl)-piperidine-4-carboxylic acid hydroxyamide;

tert-butyl-4-({[4-(2-butynyloxy)phenyl]sulfanyl}methyl)-4-[(hydroxyamino)carbonyl]-1-piperidinecarboxylate;

4-({[4-(But-2-ynyloxy)phenyl]thio}methyl)-N-hydroxypiperidine-4-carboxamide;

tert-Butyl-4-({[4-(2-butynyloxy)phenyl]sulfinyl}methyl)-4-[(hydroxyamino)carbonyl]-1-piperidinecarboxylate;

4-[[[4-(2-Butynyloxy)phenyl]sulfinyl]methyl]-N-hydroxy-4-piperidinecarboxamide;

tert-Butyl-4-({[4-(but-2-ynyloxy)phenyl]sulfonyl}methyl)-4-[(hydroxyamino)carbonyl]piperidine-1-carboxylate;

tert-butyl-4-({[4-(2-butynyloxy)phenyl]sulfonyl}methyl)-4-[(hydroxyamino)carbonyl]-1-piperidinecarboxyla;

1-Acetyl-4-[[[4-(2-butynyloxy)phenyl]sulfonyl]methyl]-N-hydroxy-4-piperidinecarboxamide;

1-(2-Butynyl)-4-({[4-(2-butynyloxy)phenyl]sulfonyl}methyl)-N-hydroxy-4-piperidinecarboxamide hydrochloride;

N-1-(tert-Butyl)-4-({[4-(2-butynyloxy)phenyl]sulfonyl}methyl)-N-4-hydroxy-1,4-[4-(2-butynyloxy)phenyl]sulfonyl}methyl)-N-4-hydroxy-1,4-1]sulfonyl}methyl)-N~4~-hydroxy-1,4-piperidinedicarboxamide;

Methyl 4-({[4-(2-butynyloxy)phenyl]sulfonyl}methyl)-4-[(hydroxyamino)carbonyl]-1-piperidinecarboxylate;

Benzyl 4-({[4-(2-butynyloxy)phenyl]sulfonyl}methyl)-4-[(hydroxyamino)carbonyl]-1-piperidinecarboxylate, 1-Benzyl-4-({[4-(2-butynyloxy)phenyl]sulfonyl}methyl)-N-hydroxy-4-butynyloxy)phenyl]sulfonyl}methyl)-N-hydroxy-4-piperidinecarboxamide;

4-({[4-(2-Butynyloxy)phenyl]sulfonyl}methyl)-N-hydroxy-1-[(2,2,5-trimethyl-1,3-dioxan-5-yl)carbonyl]-4-piperidinecarboxamide;

4-({[4-(2-Butynyloxy)phenyl]sulfonyl}methyl)-N-hydroxy-1-[3-hydroxy-2-(hydroxymethyl)-2-methylpropanoyl]-4-piperidinecarboxamide;

1-[Amino(imino)methyl]-4-({[4-(2-butynyloxy)phenyl]sulfonyl}methyl)-N-hydroxy-4-1]-4-({[4-(2-butynyloxy)phenyl]sulfonyl}methyl)-N-hydroxy-4-oxy)phenyl]sulfonyl}methyl)-N-hydroxy-4-piperidinecarboxamide;

4-({[4-(2-Butynyloxy)phenyl]sulfonyl}methyl)-N-hydroxy-1-(4-hydroxy-2-butynyl)-henyl]sulfonyl}methyl)-N-hydroxy-1-(4-hydroxy-2-butynyl)-4-piperidinecarboxamide;

4-({[4-(But-2-ynyloxy)phenyl]sulfonyl}methyl)-1-ethyl-N-hydroxypiperidine-4-carboxamide triflouroacetic acid salt;

2-chloro-5-(chloromethyl)thiophene4-({[4-(But-2-ynyloxy)phenyl]-sulfonyl}methyl)-1-[(5-chlorothien-2-yl)methyl]-N-hydroxypiperidine-4-carboxamide triflouroacetic acid salt;

4-({[4-(But-2-ynyloxy)phenyl]sulfonyl}methyl)-N-hydroxy-1-(pyridin-4-ylmethyl)piperidine-4-carboxamide triflouroacetic acid salt;

4-({[4-(But-2-ynyloxy)phenyl]sulfonyl}methyl)-N-hydroxy-1-(pyridin-3 ylcarbonyl)piperidine-4-carboxamide triflouroacetic acid salt;

1-Benzoyl-4-({[4-(but-2-ynyloxy)phenyl]sulfonyl}methyl)-N-hydroxypiperidine-4-carboxamide;

4-({[4-(But-2-ynyloxy)phenyl]sulfonyl}methyl)-N-hydroxy-1-(thien-2-ylcarbonyl)piperidine-4-carboxamide;

4-({[4-(But-2-ynyloxy)phenyl]sulfonyl}methyl)-N-1-ethyl-N-4-hydroxypiperidine-1,4-dicarboxamide;

4-({[4-(But-2-ynyloxy)phenyl]sulfonyl}methyl)-N-4-hydroxy-N-1-phenylpiperidine-1,4-dicarboxamide;

4-({[4-(But-2-ynyloxy)phenyl]sulfonyl}methyl)-N-1-,N-1-diethyl-N-4-hydroxypiperidine-1,4-dicarboxamide;

4-({[4-(But-2-ynyloxy)phenyl]sulfonyl}methyl)-N-hydroxy-1-(morpholin-4-ylcarbonyl)piperidine-4-carboxamide;

4-({[4-(But-2-ynyloxy)phenyl]sulfonyl}methyl)-N-4-hydroxy-N-1-methyl-N-1-phenylpiperidine-1,4-dicarboxamide;

Octyl-4-({[4-(but-2-ynyloxy)phenyl]sulfonyl}methyl)-4-[(hydroxyamino)carbonyl]piperidine-1-carboxylate;

4-Methoxyphenyl4-({[4-(but-2-ynyloxy)phenyl]sulfonyl}methyl)-4-[(hydroxyamino)carbonyl]piperidine-1-carboxylate;

4-({[4-(But-2-ynyloxy)phenyl]sulfonyl}methyl)-N-hydroxy-1-(phenylsulfonyl)piperidine-4-carboxamide;

4-({[4-(But-2-ynyloxy)phenyl]sulfonyl}methyl)-N-hydroxy-1-[(1-methyl-1H-imidazol-4-yl)sulfonyl]piperidine-4-carboxamide;

1-[2-(Benzylamino)acetyl]-4-({[4-(but-2-ynyloxy)phenyl]-sulfonyl}methyl)-N-hydroxypiperidine-4-carboxamide;

4-({[4-(But-2-ynyloxy)phenyl]sulfonyl}methyl)-N-hydroxy-1-(2-morpholin-4-ylacetyl)piperidine-4-carboxamide;

4-({[4-(But-2-ynyloxy)phenyl]sulfonyl}methyl)-N-hydroxy-1-[2-(4-methylpiperazin-1-yl)acetyl]piperidine-4-carboxamide;

1-Acetyl-4-(4-but-2-ynyloxybenzenesulfonyl)piperidine-4-carboxylic acid hydroxamide;

1-Benzoyl-4-(4-but-2-ynyloxybenzenesulfonyl)piperidine-4-carboxylic acid hydroxamide;

1-(4-Methoxybenzoyl)-4-(4-but-2-ynyloxybenzenesulfonyl)piperidine-4-carboxylic acid hydroxamide;

4-(4-But-2-ynyloxybenzenesulfonyl)-N-hydroxy-1-(pyrrolidine-1-carbonyl)-4-piperidinecarboxamide;

Ethyl 4-(4-but-2-ynyloxybenzenesulfonyl)-4-[(hydroxyamino)carbonyl]-1-piperidinecarboxylate;

4-(4-But-2-ynyloxybenzenesulfonyl)-N-hydroxy-1-[(trifluoromethyl)sulfonyl]-4-piperidinecarboxamide;

4-(4-But-2-ynyloxybenzenesulfonyl)-N-hydroxy-1-(3-pyridinylcarbonyl)-4-piperidinecarboxamide;

4-(4-but-2-ynyloxybenzenesulfonyl)-N-hydroxy-1-(2-thienylcarbonyl)-4-piperidinecarboxamide;

4-(4-but-2-ynyloxybenzenesulfonyl)-N-hydroxy-1-[(4-methoxyphenyl)sulfonyl]-4-piperidinecarboxamide;

4-(4-but-2-ynyloxybenzenesulfonyl)-N-hydroxy-1-[(2,2,5-trimethyl-1,3-dioxan-5-yl)carbonyl]-4-piperidinecarboxamide;

Tert-butyl-4-{[4-(2-butynyloxy)phenyl]sulfonyl)-4-[(hydroxyamino)carbonyl]-1-piperidinecarboxalate;

4-{[4-(2-butynyloxy)phenyl]sulfonyl}-N-hydroxy-4-piperidinecarboxamide hydrochloride;

Methyl ({4-{[4-(2-butynyloxy)phenyl]sulfonyl}-4-[(hydroxyamino)carbonyl]-1-piperidinyl}methyl)benzoate hydrochloride;

4-({4-{[4-(2-butynyloxy)phenyl]sulfonyl}-4-[(hydroxyamino)carbonyl]-1-piperidinyl}methyl)benzoic acid hydrochloride;

1-[4-(Aminocarbonyl)benzyl]-4-{[4-(2-butynyloxy)phenyl]sulfonyl)-N-hydroxy-4-piperidinecarboxamide hydrochloride;

Tert-butyl 4-{[4-(but-2-ynyloxy)phenyl]sulfinyl}-4-[(hydroxyamino)carbonyl]piperidine-1-carboxalate;

4-(4-(But-2-ynyloxy-benzenesulfinyl)-piperidine-4-carboxylic acid hydroxamide hydrochloride; and 1-(4-Bromo-benzyl)-4-(4-But-2-ynyloxy-benzenesulfinyl)-piperidine-4-carboxylic acid hydroxamide hydrochloride;

and pharmaceutical salts thereof.

3. A method of treating a pathological condition or disorder which requires inhibition of TNF-α converting enzyme (TACE) in a mammal in need thereof which comprises administering to said mammal a therapeutically effective amount of a compound having the formula

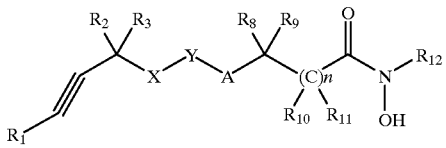

I wherein:

R$_1$ is hydrogen, aryl, heteroaryl, alkyl of 1–8 carbon atoms, alkenyl of 2–6 carbon atoms, alkynyl of 2–6 carbon atoms, cycloalkyl of 3–6 carbon atoms, or —C$_4$–C$_8$-cycloheteroalkyl;

R$_2$ and R$_3$ are each, independently, hydrogen, alkyl of 1–6 carbon atoms, —CN, or —CCH;

R$_7$ is hydrogen, aryl, aralkyl, heteroaryl, heteroaralkyl, alkyl of 1–6 carbon atoms, alkenyl of 2–6 carbon atoms, alkynyl of 1–6 carbon atoms, cycloalkyl of 3–6 carbon atoms, —C(O)—R$_1$, —SO$_2$—R$_1$, —C(O)—NHR$_1$, —C(O)NR$_5$R$_6$, —C(O)R$_1$NR$_5$R$_6$, —C(O)—OR$_1$, —C(NH)—NH$_2$;

R$_8$ and R$_9$ together with the carbon atom to which they are attached form a piperidinyl or tetrahydropyranyl ring;

R$_{10}$, and R$_{11}$ are each, independently, hydrogen, aryl, heteroaryl, cycloalkyl of 3–6 carbon atoms, —C$_4$–C$_8$-cycloheteroalkyl, alkyl of 1–18 carbon atoms, alkenyl of 2–18 carbon atoms, or alkynyl of 2–18 carbon atoms;

R$_{12}$ is hydrogen, aryl or heteroaryl, cycloalkyl of 3–6 carbon atoms, —C$_4$–C$_8$-cycloheteroalkyl, or alkyl of 1–6 carbon atoms;

A is O, S, SO, SO$_2$, NR$_7$, or CH$_2$;

X is O, S, SO, SO$_2$, NR$_7$, or CH$_2$;

Y is phenyl, with the proviso that A and X are not bonded to adjacent atoms of Y; and n is 0–2; or a pharmaceutically acceptable salt thereof.

4. The method of claim 3 wherein the condition treated is rheumatoid arthritis, graft rejection, cachexia, inflammation, fever, insulin resistance, septic shock, congestive heart failure, inflammatory disease of the central nervous system, inflammatory bowel disease or HIV infection.

5. A pharmaceutical composition comprising a therapeutically effective amount of a compound having the formula

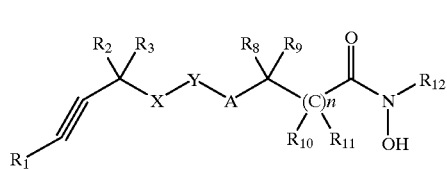

I wherein:

R$_1$ is hydrogen, aryl, heteroaryl, alkyl of 1–8 carbon atoms, alkenyl of 2–6 carbon atoms, alkynyl of 2–6 carbon atoms, cycloalkyl of 3–6 carbon atoms, or —C$_4$–C$_8$-cycloheteroalkyl;

R$_2$ and R$_3$ are each, independently, hydrogen, alkyl of 1–6 carbon atoms, —CN, or —CCH;

R$_7$ is hydrogen, aryl, aralkyl, heteroaryl, heteroaralkyl, alkyl of 1–6 carbon atoms, alkenyl of 2–6 carbon atoms, alkynyl of 1–6 carbon atoms, cycloalkyl of 3–6 carbon atoms, —C(O)—R$_1$, —SO$_2$—R$_1$, —C(O)—NHR$_1$, —C(O)NR$_5$R$_6$, —C(O)R$_1$NR$_5$R$_6$, —C(O)—OR$_1$, —C(NH)—NH$_2$;

R$_8$ and R$_9$ together with the carbon atom to which they are attached form a piperidinyl or tetrahydropyranyl ring;

R$_{10}$, and R$_{11}$ are each, independently, hydrogen, aryl, heteroaryl, cycloalkyl of 3–6 carbon atoms, —C$_4$–C$_8$-cycloheteroalkyl, alkyl of 1–18 carbon atoms, alkenyl of 2–18 carbon atoms, or alkynyl of 2–18 carbon atoms;

R$_{12}$ is hydrogen, aryl or heteroaryl, cycloalkyl of 3–6 carbon atoms, —C$_4$–C$_8$-cycloheteroalkyl, or alkyl of 1–6 carbon atoms;

A is O, S, SO, SO$_2$, NR$_7$, or CH$_2$;

X is O, S, SO, SO$_2$, NR$_7$, or CH$_2$;

Y is phenyl, with the proviso that A and X are not bonded to adjacent atoms of Y; and n is 0–2; or a pharmaceutically acceptable salt thereof.

* * * * *